(12) United States Patent
Amir et al.

(10) Patent No.: US 10,869,939 B2
(45) Date of Patent: Dec. 22, 2020

(54) DELIVERY SYSTEM IN MICELLAR FORM HAVING MODULAR SPECTRAL RESPONSE BASED ON ENZYME-RESPONSIVE AMPHIPHILIC PEG-DENDRON HYBRID POLYMERS

(71) Applicant: Ramot at Tel-Aviv University Ltd., Tel Aviv (IL)

(72) Inventors: Roey Jacob Amir, Tel-Aviv (IL); Marina Buzhor, Petach-Tikva (IL); Assaf Josef Harnoy, Tel Aviv (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 202 days.

(21) Appl. No.: 15/227,305

(22) Filed: Aug. 3, 2016

(65) Prior Publication Data
US 2017/0035916 A1 Feb. 9, 2017

Related U.S. Application Data

(60) Provisional application No. 62/200,153, filed on Aug. 3, 2015.

(51) Int. Cl.
| | | |
|---|---|---|
| A61K 49/00 | (2006.01) |
| A61K 49/18 | (2006.01) |
| A61K 49/12 | (2006.01) |
| A61K 45/00 | (2006.01) |
| C08G 83/00 | (2006.01) |

(52) U.S. Cl.
CPC .......... *A61K 49/1809* (2013.01); *A61K 45/00* (2013.01); *A61K 49/0021* (2013.01); *A61K 49/0039* (2013.01); *A61K 49/0043* (2013.01); *A61K 49/0054* (2013.01); *A61K 49/0082* (2013.01); *A61K 49/124* (2013.01); *C08G 83/003* (2013.01); *C08G 2650/32* (2013.01); *C08G 2650/40* (2013.01); *C08G 2650/48* (2013.01); *C08G 2650/50* (2013.01); *C08G 2650/58* (2013.01)

(58) Field of Classification Search
CPC ............ A61K 49/0013; A61K 49/0017; A61K 49/0019; A61K 49/0021; A61K 49/0045; A61K 49/0063; A61K 49/0065
See application file for complete search history.

(56) References Cited

U.S. PATENT DOCUMENTS

| | | |
|---|---|---|
| 4,534,891 A | 8/1985 | Boden |
| 5,112,688 A | 5/1992 | Michael |
| 5,145,842 A | 9/1992 | Driedger |
| 5,714,166 A | 2/1998 | Tomalia |
| 7,081,495 B1 * | 7/2006 | Florence ............... C08G 83/003 424/192.1 |
| 7,985,424 B2 | 7/2011 | Tomalia |
| 2002/0123609 A1 * | 9/2002 | Frechet ............... C08G 83/003 528/403 |
| 2005/0226934 A1 | 10/2005 | Goldshtein |
| 2005/0271615 A1 | 12/2005 | Shabat |

(Continued)

FOREIGN PATENT DOCUMENTS

| | | |
|---|---|---|
| CN | 103687624 A | 3/2014 |
| WO | 02/077037 | 10/2002 |

(Continued)

OTHER PUBLICATIONS

Rodríguez-Hernández and Lecommandoux (2005) Reversible inside-out micellization of pH-responsive and water-soluble vesicles based on polypeptide diblock copolymers. J Am Chem Soc 127(7): 2026-7.
Rosenbaum et al., (2015) Encapsulation and covalent binding of molecular payload in enzymatically activated micellar nanocarriers. J Am Chem Soc 137(6): 2276-84.
Roy et al., (2010) Future perspectives and recent advances in stimuli-responsive materials. Prog Polym Sci 35: 278-301.
Schmaljohann (2006) Thermo- and pH-responsive polymers in drug delivery. Adv Drug Deliv Rev 58(15): 1655-70.
Thornton and Heise (2011) Bio-functionalisation to enzymatically control the solution properties of a self-supporting polymeric material. Chem Commun (Camb) 47(11): 3108-10.
Walter and Malkoch (2012) Simplifying the synthesis of dendrimers: accelerated approaches. Chem Soc Rev 41(13): 4593-609.

(Continued)

*Primary Examiner* — Micah Paul Young
(74) *Attorney, Agent, or Firm* — Browdy and Neimark, PLLC

(57) ABSTRACT

The present invention relates to new molecular design that allows micelles to report their activation and disassembly by an enzymatic trigger. The molecular design is based on introduction of a labeling moiety selected from a fluorescent dye, a dark quencher, combinations of dyes or dyes/quenchers, and a fluorinated moiety (a $^{19}$F-magenetic resonance (MR) probe for turn ON/OFF of a $^{19}$F-MR signal) through covalent binding to the focal point of amphiphilic polymer-dendron hybrids with the labeling moiety. At the assembled micellar state, the dyes are closely packed and hence the probability for intermolecular interactions increases significantly, leading to alteration of the fluorescent properties (signal quench or shift) or the $^{19}$F-MR signal (OFF state) of the micelles. Upon enzymatic cleavage of the hydrophobic end-groups from enzyme-responsive dendron, the polymers become hydrophilic and disassemble. This structural change is then translated into a spectral change as dye-dye interactions are halted and the dyes regain their intrinsic fluorescent properties, or alternatively by turn ON the $^{19}$F-MR signal. The high modularity of the design allows the introduction of various types of dyes and thus enables rational adjustment of the spectral response. Two major types of responses are described: Turn-On/Off and spectral shift, depending on the type of labeling dye. The present invention further provides methods of use of the hybrid delivery system and to a kit comprising the same.

46 Claims, 25 Drawing Sheets

(56) References Cited

U.S. PATENT DOCUMENTS

| | | | |
|---|---|---|---|
| 2006/0269480 A1 | 11/2006 | Amir | |
| 2008/0294089 A1* | 11/2008 | Hardy | A61K 9/0009 604/22 |
| 2010/0010103 A1 | 1/2010 | Schmidt | |
| 2011/0230348 A1 | 9/2011 | Hayes | |
| 2012/0101041 A1 | 4/2012 | Mynar | |
| 2012/0183578 A1 | 7/2012 | Sinko | |
| 2013/0123461 A1 | 5/2013 | Ashley | |
| 2014/0037747 A1 | 2/2014 | Hong | |

FOREIGN PATENT DOCUMENTS

| | | | |
|---|---|---|---|
| WO | 2012/153297 | | 11/2012 |
| WO | 2012/153297 A1 | | 11/2012 |
| WO | WO-2012153297 A1 * | | 11/2012 ... A61K 47/24 |
| WO | 2013/096388 | | 6/2013 |
| WO | 2016/038595 | | 3/2016 |
| WO | 2016/038596 | | 3/2016 |

OTHER PUBLICATIONS

Wang et al., (2011) Temperature sensitivity trends and multi-stimuli sensitive behavior in amphiphilic oligomers. J Am Chem Soc 133(34): 13496-503.

Wang et al., (2015) Activatable Dendritic 19F Probes for Enzyme Detection. ACS Macro Lett 4(4): 422-425.

Yesilyurt et al., (2011) Photoregulated release of noncovalent guests from dendritic amphiphilic nanocontainers. Angew Chem Int Ed Engl 50(13): 3038-42.

Yu (2013) Fluorinated dendrimers as imaging agents for $^{19}$F MRI. Wiley Interdiscip Rev Nanomed Nanobiotechnol 5(6): 646-61.

Zhou et al., (2012) Multicolored pH-tunable and activatable fluorescence nanoplatform responsive to physiologic pH stimuli. J Am Chem Soc 134(18): 7803-11.

Zhou et al., (2013) Linear-dendritic drug conjugates forming long-circulating nanorods for cancer-drug delivery. Biomaterials 34: 5722-5735.

Larson & Weber, "Hydrolysis; in: Reaction mechanisms in environmental organic chemistry." CRC press (1994).

Akelah et al., (1992) Agricultural polymers with a combined herbicide/fertilizer function—I. Tartrate-based systems. European polymer journal 28(5): 453-463.

Akelah et al., (1993) Agricultural polymers with herbicide/fertilizer function—III. Polyureas and poly (Schiff base) s based systems. European polymer journal 29(8): 1041-1045.

Amir (2015) Enzyme-Responsive PEG-Dendron Hybrids as a Platform for Smart Nanocarriers. Synlett 26(19): 2617-2622.

Amir et al., (2003) Self-Immolative Dendrimers. Angew Chem Int Ed 42: 4494-4499.

Amir et al., (2005) Prodrug activation gated by a molecular "OR" logic trigger. Angew Chem Int Ed Engl 44(28): 4378-81.

Amir et al., (2009) Enzymatically Triggered Self-Assembly of Block Copolymers. J Am Chem Soc 131(39): 13949-13951.

Azagarsamy et al., (2009) Enzyme-Triggered Disassembly of Dendrimer-Based Amphiphilic Nanocontainers. J Am Chem Soc 131(40): 14184-14185.

Balamuralidhara et al., (2011) pH Sensitive Drug Delivery Systems: A Review. American Journal of Drug Discovery and Development 1(1): 24-48.

Bema et al., (2006) Novel monodisperse PEG-dendrons as new tools for targeted drug delivery: synthesis, characterization and cellular uptake. Biomacromolecules 7(1): 146-53.

Blum et al., (2015) Stimuli-responsive nanomaterials for biomedical applications. J Am Chem Soc 137(6): 2140-54.

Bruchard et al., (2013) Chemotherapy-triggered cathepsin B release in myeloid-derived suppressor cells activates the Nlrp3 inflammasome and promotes tumor growth. Nat Med 19(1): 57-64.

Buzhor and Amir (2015) Self-reporting enzyme-responsive micellar nanocarriers as drug delivery platform. Poster presented at the Third Conference of the Israel Society for Biotechnology Engineering, Dec. 13, 2015, Tel-Aviv.

Buzhor and Amir (2016) Spectrally active micellar nanocarriers. Poster presented at the 81st Annual Meeting of the Israel Chemical Society, Feb. 9-10, 2016, Tel-Aviv.

Buzhor et al., (2015) Smart Fluorescent Labeling of Enzyme Responsive Micellar Nanocarriers. Poster presented at the 80th Annual Meeting of the Israel Chemical Society, Feb. 17-18, 2015, Tel-Aviv.

Buzhor et al., (2015) Supramolecular Translation of Enzymatically Triggered Disassembly of Micelles into Tunable Fluorescent Responses. Chemistry—A European Journal 21(44): 15633-15638.

Buzhor et al., (2016) Fluorinated smart micelles as enzyme-responsive probes for 19F-magnetic resonance. J Mater Chem B 4: 3037-3042.

De et al., (2008) Folate-conjugated thermoresponsive block copolymers: highly efficient conjugation and solution self-assembly. Biomacromolecules 9(3): 1064-70.

de Groot et al., (2003) "Cascade-Release Dendrimers" Liberate All End Groups upon a Single Triggering Event in the Dendritic Core. Angew Chem Int Ed 42: 4490-4494.

Ding et al., (2015) Enzyme-responsive polymer assemblies constructed through covalent synthesis and supramolecular strategy. Chem Commun (Camb) 51(6): 996-1003.

Fréchet et al., (1999) Modification of Surfaces and Interfaces by Non-covalent Assembly of Hybrid Linear-Dendritic Block Copolymers: Poly(benzyl ether) Dendrons as Anchors for Poly(ethylene glycol) Chains on Cellulose or Polyester. Chem Mater 11(5): 1267-1274.

Ganta et al., (2008) A review of stimuli-responsive nanocarriers for drug and gene delivery. Journal of Controlled Release 126: 187-204.

Gillies et al., (2004) Stimuli-Responsive Supramolecular Assemblies of Linear-Dendritic Copolymers. J Am Chem Soc 126(38): 11936-11943.

Gillies et al., (2005) pH-Responsive Copolymer Assemblies for Controlled Release of Doxorubicin. Bioconjug Chem 16 (2): 361-368.

Gitsov (2008) Hybrid linear dendritic macromolecules: From synthesis to applications. Journal of Polymer Science Part A: Polymer Chemistry 46(16): 5295-5314.

Guo et al., (2014) Protein and enzyme gated supramolecular disassembly. J Am Chem Soc 136(6): 2220-3.

Harnoy et al., (2014) Enzyme-responsive amphiphilic PEG-dendron hybrids and their assembly into smart micellar nanocarriers. J Am Chem Soc 136(21): 7531-4.

Harnoy et al., (2016) TThe Effect of Photoisomerization on the Enzymatic Hydrolysis of Polymeric Micelles Bearing Photo-Responsive Azobenzene Groups at Their Cores. Org Biomol Chem 14(24): 5813-5819.

Hoogenboom (2010) Thiol-yne chemistry: a powerful tool for creating highly functional materials. Angew Chem Int Ed Engl 49(20): 3415-7.

Hu et al., (2012) Enzyme-responsive polymeric assemblies, nanoparticles and hydrogels. Chem Soc Rev 41(18): 5933-49.

Hu et al., (2014) Enzyme-responsive nanomaterials for controlled drug delivery. Nanoscale 6: 12273-12286.

Huang et al., (2013) Multi-chromatic pH-activatable 19F-MRI nanoprobes with binary ON/OFF pH transitions and chemical-shift barcodes. Angew Chem Int Ed Engl 52(31): 8074-8.

Jiang et al., (2008) Multiple Micellization and Dissociation Transitions of Thermo- and Light-Sensitive Poly(ethylene oxide)-b-poly(ethoxytri(ethylene glycol) acrylate-co-o-nitrobenzyl acrylate) in Water Macromolecules 41(7): 2632-2643.

Jiang et al., (2011) Reactive fluorescence turn-on probes for fluoride ions in purely aqueous media fabricated from functionalized responsive block copolymers. Macromolecules 44(22): 8780-8790.

Ku et al., (2011) Controlling and Switching the Morphology of Micellar Nanoparticles with Enzymes. J Am Chem Soc 133(22): 8392-8395.

Langer and Tirrell (2004) Designing materials for biology and medicine. Nature 428(6982): 487-92.

(56) References Cited

OTHER PUBLICATIONS

Lee et al., (2007) Colorimetric Detection of Mercuric Ion (Hg2+) in Aqueous Media using DNA-Functionalized Gold Nanoparticles. Angew Chem Int Ed 46(22): 4093-4096.
Lee et al., (2007) Light-induced reversible formation of polymeric micelles. Angew Chem Int Ed Engl 46(14): 2453-7.
Li and Liu (2012) Polymeric assemblies and nanoparticles with stimuli-responsive fluorescence emission characteristics. Chem Commun (Camb) 48(27): 3262-78.
Louie et al., (2000) In vivo visualization of gene expression using magnetic resonance imaging. Nat Biotechnol 18(3): 321-5.
Lowe (2014) Thiol-yne 'click'/coupling chemistry and recent applications in polymer and materials synthesis and moditication. Polymer 55(22): 5517-5549.
Lundberg et al., (2013) pH-triggered self-assembly of biocompatible histamine-functionalized triblock copolymers. Soft Matter 9(1): 82-89.
Mai and Eisenberg (2012) Self-assembly of block copolymers. Chem Soc Rev 41(18): 5969-85.
Naahidi et al., (2013) Biocompatibility of engineered nanoparticles for drug delivery. Journal of Controlled Release 166: 182-194.
Napolitano et al., (2013) Synthesis and relaxometric characterization of a MRI Gd-based probe responsive to glutamic acid decarboxylase enzymatic activity. J Med Chem 56(6): 2466-77.
Pearson et al., (2012) Dendritic nanoparticles: the next generation of nanocarriers? Ther Deliv 3(8): 941-59.
Prof. Roey Amir "Designing enzyme-responsive polymeric micelles with diverse supramolecular spectral responses". Spring 2016 Seminar Series, Jun. 20, 2016. Massachusetts Institute of Technology Cambridge, MA. 91 pages.
Qiao et al., (2012) Thermal responsive fluorescent block copolymer for intracellular temperature sensing. J Mater Chem 22: 11543-11549.
Raghupathi et al., (2011) Guest-release control in enzyme-sensitive, amphiphilic-dendrimer-based nanoparticles through photochemical crosslinking. Chemistry 17(42): 11752-60.
Rao et al., (2013) Enzyme Sensitive Synthetic Polymer Micelles Based on the Azobenzene Motif J Am Chem Soc 135 (38): 14056-14059.
Rao et al., (2014) Enzyme-Triggered Cascade Reactions and Assembly of Abiotic Block Copolymers into Micellar Nanostructures. J Am Chem Soc 136(16): 5872-5875.
Chang et al., Synthesis and micellar characteristics of dendron-PEG conjugates. Langmuir 21(10): 4334-4339 (2005).
Fleige et al., (2012) Stimuli-responsive polymeric nanocarriers for the controlled transport of active compounds: concepts and applications. Adv Drug Deliv Rev 64(9): 866-884.
Nlajlah et al., (2006) Synthesis, characterization and stability of dendrimer prodrugs. Int J Pharm 308(1-2): 175-182.
Sharma et al., (2014) "Onion peel" dendrimers: a straightforward synthetic approach towards highly diversified architectures. Polym Chem 5: 4321-4331.
Li et al., (2009) Novel polymeric micelles of AB2 type alpha-methoxy-poly(ethylene glycol)-b-Poly(gamma-benzyl-L-glutamate), copolymers as tamoxifen carriers. J Nanosci Nanotechnol 9(8): 4805-4811.
Sui et al., (2014) Self-assembled micelles composed of doxorubicin conjugated Y-shaped PEG-poly(glutamic acid)2 copolymers via hydrazone linkers. Molecules 19(8): 11915-11932.

\* cited by examiner

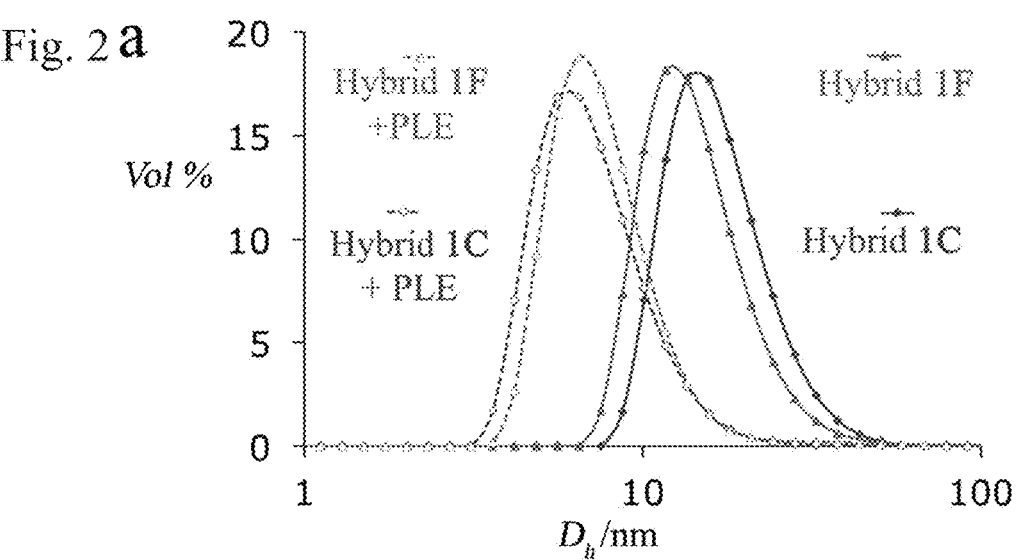
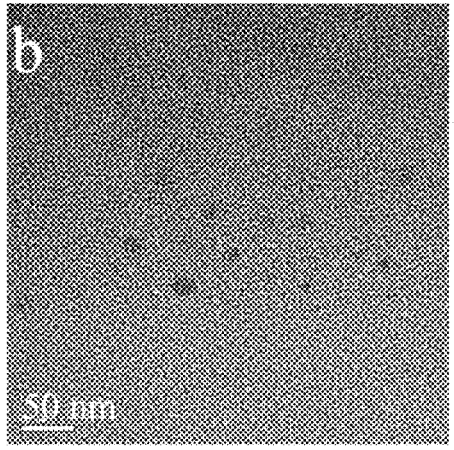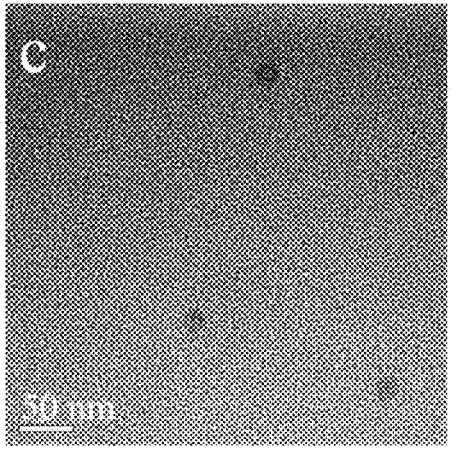

DELIVERY SYSTEM IN MICELLAR FORM HAVING MODULAR SPECTRAL RESPONSE BASED ON ENZYME-RESPONSIVE AMPHIPHILIC PEG-DENDRON HYBRID POLYMERS

FIELD OF THE INVENTION

The present invention relates to an enzymatic stimuli-responsive amphiphilic delivery system in micellar form, comprising at least one hybrid polymer or a mixture of polymers. Each polymer is based on a hydrophilic polyethylene glycol (PEG) polymer conjugated to a hydrophobic dendron and a labeling moiety selected from a fluorescent dye, a dark quencher and a fluorinated moiety that acts as a magnetic probe for turn on/off of $^{19}$F-magnetic resonance (MR) signal. The delivery system disassembles upon enzymatic stimuli/cleavage, leading to a change in the fluorescence of the dye or turn-on of a $^{19}$F-MR signal. The hybrid delivery systems of the invention can be self-assembled into therapeutic drug delivery platforms that can self-report their location and degree of activation.

BACKGROUND OF THE INVENTION

Stimuli-responsive micelles based on smart amphiphilic block copolymers are gaining increasing interest due to their potential application as drug delivery systems. Many research groups have designed and prepared micelles that can encapsulate hydrophobic molecular cargo and release it in response to various types of stimuli. In recent years, efforts have been devoted to use smart polymers and their assemblies to create advanced materials with responsive fluorescence. Such assemblies alter both their amphiphilicity and fluorescence in response to irradiated light, changes in temperature, pH and combinations of stimuli. A fluorescent response to the disassembly of micellar nanocarriers would be extremely beneficial, as it would allow simple monitoring of the release of encapsulated cargo. Responsive fluorescence would be useful in designing advanced imaging probes and drug delivery platforms that report their activation by altering their fluorescence.

Among the various types of stimuli, enzymes are extremely attractive for selectively triggering the release of hydrophobic drug molecules from smart micellar nanocarriers due to often observed over-expression of specific disease associated enzymes. To date, however, there are only limited reports on synthetic amphiphilic block copolymers that can disassemble and change their fluorescence in response to enzymatic stimuli.[1,2] These changes in fluorescence are often achieved by utilizing the fluorescent dyes as cleavable hydrophobic groups that are linked through their electron donating group to the polymeric platform. This type of linkage blocks or decreases the fluorescence of the attached dyes. Upon their enzymatic hydrolysis and release from the polymeric backbone, the electron donation into the conjugated system is regained and the fluorescence is turned on.

Recently a different spectral mechanism was reported to achieve enzyme-responsive fluorescent response. This approach was based on utilizing the formation of coumarin-derived excimers within the dendritic structures in order to achieve a red-shift of the emitted fluorescence spectra before the enzymatic stimuli.[3] The polymeric platform was based on amphiphilic block copolymers of a linear polyethylene glycol (PEG) chain as the hydrophilic block and a dendron with lipophilic coumarin dyes as enzymatically cleavable end-groups, serving as the hydrophobic block. In aqueous solution, such amphiphilic hybrids self-assemble into micelles with a PEG shell and a hydrophobic core consisted of the lipophilic dendrons. Enzymatic cleavage of the end-groups increases the hydrophilicity of the dendrons, resulting in destabilization of the micelles and consequent release of the encapsulated molecular cargo.[4] Using coumarin derivatives as covalently bound hydrophobic end-groups, it was demonstrated that the micelles can report their disassembly by changing their fluorescence spectra upon enzymatic hydrolysis of the dyes, which diminished the ability of the dyes to form excimers after they were released from the polymeric platfrom.[3] Although the covalent binding of the dye though an enzymatically cleavable bond and its incorporation as part of the enzyme responsive moiety, either by modification of the electronic conjugation of the dyes or their ability to form excimers, allow the generation of spectral changes in response to the enzymatic activation, these approaches might also be highly limited. It is clear that the requirement that the dye will serve as the enzymatic substrate may hamper the generality of these approaches in cases that the structural properties of the dye are substantially different than those of the natural substrate of the target enzyme and hence the dye might not be recognized or manipulated by the activating enzyme. Furthermore, it can be expected that functionalization with different dyes will result in extremely different release rates and stabilities, which will need to be studied thoroughly and adjusted for each type of dye.

The development of biomedical imaging techniques including positron emission tomography (PET), computed tomography (CT), ultrasound, optical imaging and magnetic resonance imaging (MRI) has enabled acquisition of highly valuable anatomical information, which allows the diagnosis of diseases and monitoring of the progress of their medical treatment. Among the various imaging tools, MRI serves as a highly important non-invasive tomographic imaging technique due to its high spatial resolution, deep tissue penetration and safety. In recent years major efforts have focused on the development of responsive MRI probes that possess sensitivity to the specific microenvironments of diseased tissues compared to healthy ones. These can be differences in pH values, over- or sub-expression of proteins or other molecular species, which if can be monitored, can provide important information about the status of the diseased tissues, organs and tumors.

Potentially, the most appealing approach to design MRI probes is to design imaging probes that can respond to pathologically relevant enzymes that are over-expressed in the target tissue. A low molecular weight smart MRI contrast agent that was designed to respond to the enzyme β-galactosidase (an important marker for monitoring gene expression) has previously been reported.[5] The enzymatic cleavage of a (β-galactose moiety that was blocking the H$_2$O ligation site on a gadolinium atom, led to an irreversible 20% increase in relaxation rate. Since then, several similar approaches have been reported to modulate MRI contrast through the control of water access to a chelated paramagnetic center.[6] However, reliance on inner sphere hydration as the response mechanism of smart MRI probes is not ideal due to potential anion interactions with the cleaved (more solvated/accessible) paramagnetic center, which has been identified to be a considerable interfering factor, particularly in vivo, where water-competing anions are abundant.

An alternative approach for the design of stimuli-responsive magnetic resonance (MR) probes would be to use fluorinated stimuli-responsive amphiphilic block-copolymers as smart platforms that allow the supramolecular translation of the stimuli-induced disassembly into the turn-ON of the $^{19}$F-MR signal. Compared to $^1$H-MRI, $^{19}$F-MRI has almost no biological background due to the absence of fluorine in the body. Furthermore, $^{19}$F has 100% natural abundance and its gyromagnetic ratio (40.06 MHz/T), which is second only to $^1$H, makes it more sensitive for detection over other nuclei. Stimuli-responsive polymers have gained increasing interest due to their potential applications ranging from drug delivery to tissue engineering.[7-9] In recent years smart polymers were further exploited to transform non-responsive fluorescent dyes into responsive dyes by utilizing the ability of these polymers to change their structure in response to stimuli, such as changes in pH,[10] temperature[11] and chemical analytes.[12] These structural changes were shown to alter the microenvironments of the dyes, which responded by spectral changes.[13]

For MR probes, the supramolecular translation mechanism may rely on the expected changes in spin-spin relaxation ($T_2$) when going from micellar or aggregated states into a monomeric non-assembled form. In the assembled form, the $T_2$ relaxation time should be extremely short and hence the fluorinated responsive block is expected to be in its OFF state and show almost no signal due to its extremely low mobility. Upon stimuli, the increase in hydrophilicity should result in increase in the mobility of the responsive fluorinated-block and its $T_2$ relaxation time, leading to turning ON of the MR signal. Gao and Sherryl[14] utilized fluorine containing pH responsive block copolymers in order to prepare $^{19}$F-NMR/MRI nanoprobes that can be turned ON at different pH levels based on the pKa values of the pH-responsive amine moieties. Thayumanavan and coworkers reported the use of fluorine-containing groups that were linked through cleavable ester bonds to amphiphilic dendrons.[15] These fluorinated dendrons formed sub-micron assemblies that showed a broad peak in the absence of the esterase. The addition of the activating enzyme resulted in the formation of a new sharp peak at slightly higher chemical shift, due to the release of the low molecular weight fluorinated end-groups that were cleaved by the enzyme.

Modular amphiphilic hybrids based on hydrophilic PEG block and a hydrophobic enzyme-responsive dendrons, which could assemble into smart micellar nanocarriers, have been reported.[3, 4]

PCT International Patent Publication No. WO2016/038595 to some of the inventors of the present application describes an enzymatic stimuli-responsive amphiphilic hybrid delivery system in micellar form, based on a hydrophilic polyethylene glycol (PEG) polymer conjugated to a hydrophobic dendron. The delivery system disassembles upon enzymatic stimuli/cleavage.

PCT International Patent Publication No. WO2016/038596 to some of the inventors of the present application describes an enzyme- or pH-responsive amphiphilic hybrid delivery system in micellar form for delivery of agrochemicals, based on a hydrophilic polyethylene glycol (PEG) polymer conjugated to a hydrophobic dendron. The delivery system disassembles upon enzymatic trigger or pH-based stimuli.

There is an ongoing need in the art to generate more advanced fluorescent imaging and delivery platforms, e.g., systems that allow translation of stimuli-triggered disassembly of polymeric micelles into fluorescent or magnetic resonance responses.

SUMMARY OF THE INVENTION

To address the aforementioned challenges and enable the design of generic smart delivery or diagnostic platforms, the present invention provides a new molecular design that allows the direct supramolecular translation of enzymatically-triggered disassembly of polymeric micelles into tailor-made fluorescent responses or $^{19}$F probes for turn-on/off of $^{19}$F-magnetic resonance signal ($^{19}$F-MR probes). This molecular design uncouples the need to use the dyes as part of the enzyme-responsive functionalities and hence circumvent the challenges that are associated with designing enzyme-responsive dyes or $^{19}$F-MR probes.

The present invention relates to a new molecular design that enables supramolecular translation of the enzymatically-triggered disassembly of micelles or other types of self-assembled structures into tailor-made fluorescence responses. This modular design is based on labeling enzyme responsive PEG-dendron hybrid polymers by a fluorescent dye, preferably at the focal point between the PEG and the dendron. In the micellar form, the dyes are closely packed at the interface between the PEG shell and the hydrophobic core. This spatial proximity leads to increased supramolecular dye-dye interactions and hence the self-assembled structures (i.e., micelles) are hypothesized to have different fluorescent spectrum (e.g., quenching or shifting of fluorescence) compared with the intrinsic properties of the dye. For example, upon enzymatic cleavage of the hydrophobic end-groups, the micelles disassemble into hydrophilic hybrids, which can diffuse away from each other. As the distances between the labeled hybrids increase, the non-assembled dyes are expected to regain their intrinsic fluorescence. To demonstrate this new molecular design, two types of fluorescence responses were developed: turn-on/off or spectral shift, depending on the type of the labeling dye (FIGS. 1A and 1B). Enzymatically triggered turn-on of fluorescence can be expected for dyes with small stock shift, which are more prone for self-quenching at the assembled state of the micelle (designated herein "self-quenching dyes"). In addition, combinations of fluorescent dyes and dark quenchers result in quenching of the fluorescent signal at the assembled state of the micelle. Enzymatic activation of the disassembly mechanism and the separation of the dyes (or the dyes and dark quenchers) would halt the self-quenching and restore their strong fluorescence. On the other hand, dyes that can form excimers are expected to show spectral shift when two approximate dyes in the assembled state are separated upon enzymatic disassembly of the micelles. In addition, dye-dye interactions formed from a mixture of two fluorescent dyes (FRET pairs) is expected to show spectral shift in the assembled state vs. unassembled micelles.

In another aspect of the present invention, labeling of smart PEG-dendron hybrids with fluorinated groups transformed their assemblies into enzyme-responsive micellar probes that can be used for $^{19}$F-magnetic resonance (MR). As demonstrated herein, these smart hybrids are turned OFF at the assembled micellar state and turned ON their $^{19}$F-MR signal upon enzymatic activation.

Thus, in some embodiments of the present invention, it was discovered that smart hybrid polymers can be transformed into enzyme-responsive $^{19}$F-MR probes by incorporating fluorinated labeling moieties. These probes have been shown to turn ON their magnetic resonance signal upon enzymatic activation, as the fluorinated derivatives become more hydrophilic and their mobility and $T_2$ relaxation increase. According to the principles of the present invention, the fluorinated groups are incorporated as a non-cleavable label into the dendrons of the present invention, for example between the PEG and dendron (FIG. 19), were used in order to test the postulated translation mechanism. A significant change in $T_2$ relaxation can be expected, due to increase in hydrophilicity and disassembly of the fluorinated hydrophilic hybrids.

The new molecular designs described herein possess the following advantages:

1. The labeling moieties are not a direct part of the enzymatic activation mechanism and don't need to be cleaved from the polymers. Instead the fluorescence or $^{19}$F-MR signal respond to the supramolecular structural change of the polymeric platform.
2. The modular synthesis allows very high versatility and minimal synthetic efforts as the enzymatic substrate and labeling moiety are conjugated only in the two last steps.
3. The molecular approach can be applied to nearly any labeling dye and the type of spectral response can be rationally tuned by choosing the proper dye or combination of dyes or combination of dyes with dark quenchers. Also nearly any fluorinated molecule can serve as a $^{19}$F probe for turn-on of the MR signal.
4. This system allows very modular adjustment of the enzymatic activity by simple introduction of the proper enzymatic substrate and enzymatically cleavable end group.
5. This molecular design opens the way to a delivery platform that can report the degree and location of their activation.

Applications of the hybrid delivery systems of the invention include but are not limited to:

1. Diagnostic probes for monitoring specific enzymatic activity.
2. Thernsotic probes capable of reporting the degree and location of activation.
3. $^{19}$F-magnetic resonance probes for turn on/off of magnetic resonance signal.

Thus, according to one aspect, the present invention provides a hybrid polymer comprising: (i) a hydrophilic polyethylene glycol (PEG) polymer; (ii) a hydrophobic dendron, the dendron comprising at least one enzymatically cleavable hydrophobic end group that is covalently attached to the dendron; and (iii) at least one labeling moiety elected from a fluorescent dye, a dark quencher, and a fluorinated labeling moiety; wherein the PEG polymer, hydrophobic dendron and labeling moiety are covalently attached, directly or through a multi-functional moiety. In one embodiment, the labeling moiety is a fluorescent dye. In another embodiment, the labeling moiety is a dark quencher. In another embodiment, the labeling moiety is a fluorinated moiety.

In another aspect, the present invention provides a self-assembled amphiphilic delivery system in micellar form, comprising at least one hybrid polymer as described above, or a combination of such hybrids. According to the principles of the present invention, the micelle disassembles upon enzymatic cleavage of the hydrophobic end group, wherein the labeling moiety provides a different signal (fluorescence or $^{19}$F-MR signal) in the assembled vs. unassembled state of the micelle.

In some embodiments, the delivery system comprises a multiplicity of hybrid polymers, each containing the same type of labeling moiety (i.e., a fluorescent dye, a dark quencher or a fluorinated labeling moiety). In other embodiments, the delivery system comprising a multiplicity of hybrid polymers which is a mixtures of polymers comprising different types of labeling moieties. According to the principles of the present invention, there are alternative embodiments for self-assembly that lead to altered supramolecular spectral properties (FIGS. 1A and 1B):

(a) A self-assembled delivery system comprising a hybrid polymer labeled with self-quenching fluorescent dye (FRET). In this case the fluorescent signal is wholly or partially quenched (or turned off) when the micelle is in the assembled state. Upon enzymatic cleavage and micelle disassembly, the fluorescent dye regains its intrinsic fluorescent properties (FIG. 1B-1).

(b) A self-assembled delivery system based on a mixture of hybrid polymer labeled with a fluorescent dye and a hybrid polymer labeled with a dark quencher. In this case the fluorescence of the dye is wholly or partially quenched (or turned off) when the micelle is in the assembled state. Upon enzymatic cleavage and micelle disassembly, the dark quencher and the fluorescent dye are separated, and the fluorescent dye regains its intrinsic fluorescent properties (FIG. 1B-2).

(c) A self-assembled delivery system based on a mixture of hybrid polymers labeled by two or more different fluorescent dyes (FRET pairs). In this case, the fluorescence of the dyes is shifted upon micelle assembly and disassembly due to altered dye-dye interactions upon micelle assembly (FRET) and disassembly (spectral shift) (FIG. 1B-3).

(d) A hybrid delivery system comprising a hybrid polymer labeled with an excimer forming fluorescent dye, In this case the fluorescent signal of the dye is shifted upon micelle assembly and disassembly due to altered dye-dye interactions upon micelle assembly and disassembly (spectral shift) (FIG. 1B-4).

As contemplated herein, the fluorescence of the dye changes upon micelle assembly or disassembly to display different properties of the dye in the assembled vs. unassembled state. In one embodiment, the fluorescence of the dye is wholly or partially quenched upon micelle assembly, and the dye regains its intrinsic fluorescence upon micelle disassembly. In another embodiment, the fluorescence of the dye is shifted upon micelle assembly, and the dye regains its intrinsic fluorescence upon micelle disassembly. The alteration of the spectral properties will depend on the nature of the hybrid delivery system (i.e., whether it comprises a self-quenching dye, an excimer-forming dye, a combination of dyes or a combination of a dye and a dark quencher).

In some embodiments, the labelling moiety is a fluorescent dye or a dark quencher, selected from the group consisting of a coumarin, a cyanine dye, an azo dye, an acridine, a fluorone, an oxazine, a phenanthridine, a naphthalimide, a rhodamine, a benzopyrone, a perylene, a benzanthrone, and a benzoxanthrone. In particular non-limiting embodiments, the fluorescent dye is or is the residue of a compound selected from the group consisting of Coumarin, Fluorescein, Cyanine 3 (Cy3), Cyanine 5 (Cy5), Cyanine 7 (Cy7), Alexa dyes, bodipy derivatives, (E)-2-(4-phenyldiazenyl)phenoxy)acetic acid, 3-(3',3'-dimethyl-6-nitrospiro[chromene-2,'-indolin]-1'-yl)propanoate (Spiropyran), 3,5-dihydroxybenzoate and (E)-2-(4-(phenyldiazenyl)phenoxy) acetic acid, or combinations thereof. Each possibility represents a separate embodiment of the present invention.

In another embodiment, the labeling moiety is a fluorinated labeling moiety, which functions as a magnetic resonance (MR) probe capable of turning on a $^{19}$F-MR signal. As contemplated herein, the signal generated by the probe changes upon micelle assembly or disassembly to display different properties of the fluorinated labeling group in the assembled vs. unassembled state. In one embodiment, the $^{19}$F-MR signal is turned OFF upon micelle assembly, and turned ON upon enzymatic activation and micelle disassembly.

In one embodiment, the multi-functional moiety in the hybrid polymer comprises a trifunctional moiety that is capable of attaching to the hydrophobic dendron, the PEG polymer, and the labeling moiety. In a currently preferred embodiment, the trifunctional group is covalently attached to the labeling moiety and is present at a focal point between the PEG polymer and the dendron. In some embodiments, the trifunctional moiety is selected from the group consisting of an amino acid, a C1-C20 alkylene, a C2-C20 alkenylene, a C2-C20 alkynylene and an arylene, each comprising at least three functional groups selected from the group consisting of —C(=O)—O—, —NH—, —O—, —S—, —C(=O)—, —O—C(=O)—O—, —C(=O)—NH—, —NH—C(=O)—NH—, —NH—C(=O)—O—, —S(=O)—, —S(=O)—O—, —PO(=O)—O—, and any combination thereof. Each possibility represents a separate embodiment of the present invention.

In some currently preferred embodiments, the trifunctional moiety is an amino acid capable of attaching to the hydrophobic dendron, the PEG polymer, and the fluorescent dye through its carboxyl group, amino group, and side chain. In a currently preferred embodiment, the trifunctional moiety is an alpha-amino acid selected from the group consisting of lysine, aspartic acid, glutamic acid, tyrosine, asparagine, serine, homoserine, cysteine, homocysteine, glutamine, threonine, ornithine, citrulline and arginine. In another currently preferred embodiment, the trifunctional moiety is lysine.

According to some embodiments, the enzymatically cleavable hydrophobic end group is conjugated to the dendron through an enzymatically cleavable functional group selected from the group consisting of an ester, an amide, a carbamate, a carbonate, a urea, a sulfate, an amidine, an ether, a phosphate, a phosphoamide, sulfamates, and a trithionate. Each possibility represents as separate embodiment of the present invention.

According to some embodiments, the enzymatically cleavable hydrophobic end group is conjugated to the dendron through an amide which is cleavable by an amidase. In one embodiment, the amidase is selected from the group consisting of aryl-acylamidase, aminoacylase, alkylamidase, and phthalyl amidase. Each possibility represents as separate embodiment of the present invention.

According to some embodiments, the enzymatically cleavable hydrophobic end group is conjugated to the dendron through an ester which is cleavable by an esterase. In one embodiment, the esterase is selected from the group consisting of carboxylesterase, arylesterase, and acetylesterase. Each possibility represents as separate embodiment of the present invention.

According to some embodiments, the enzymatically cleavable hydrophobic end group is represented by the structure —O—C(O)—R', —C(O)—OR'—NH—C(O)—R' or —C(O)—NHR' wherein R' is C1-C12 alkyl or an aryl.

In some embodiments, the micelle has an average particle size of less than about 100 nm, preferably about 50 nm or lower, more preferably about 10 nm to 50 nm, and most preferably about 10 nm to 20 nm. Each possibility represents as separate embodiment of the present invention.

According to some embodiments, the dendron comprises a plurality of enzymatically cleavable hydrophobic end groups.

According to some embodiments, the enzymatically cleavable hydrophobic end group is present at one or more of the terminal repeating units (i.e., terminal generations) of the hydrophobic dendron, and/or in intermediary generations of the dendron. In other embodiments, the enzymatically cleavable hydrophobic end group is present only at the terminal repeating units of the hydrophobic dendron (i.e., the enzymatically cleavable hydrophobic end group is not present in intermediary generations of the dendron).

According to some embodiments, the PEG has an average molecular weight between about 0.5 and 70 kDa, e.g., 2 kDa, 5 kDa and 10 kDa, 20 or 30 kDa, etc. Preferably, the PEG has at least 10 repeating units of ethylene glycol monomers.

According to various embodiments, the PEG is functionalized at its terminus and linked to the dendron or the multi-functional moiety through a PEG terminal functional group. For example, the PEG may be linked to the trifunctional moiety by a group selected from the group consisting of —(CH$_2$)$_t$—X—(CH$_2$)X—, —X—(CH$_2$)$_t$—X—, —(CH$_2$)$_t$— wherein X is independently at each occurrence selected from O, S and NH, and t is independently at each occurrence 1-10; —O—, —S—, —NH—, —C(=O)—, —C(=O)—O—, —O—C(=O)—O—, —C(=O)—NH—, —NH—C(=O)—NH—, —NH—C(=O)—O—, —S(=O)—, —S(=O)—O—, —PO(=O)—O—, —C=C—, —C≡C—, triazolyl, and any combination thereof. The PEG functional group is advantageously chosen to be compatible with the corresponding functional group in the trifunctional moiety or the dendron. A currently preferred PEG functional group is —(CH$_2$)$_3$—S—(CH$_2$)$_2$—NH—, which is introduced by allylation of PEG-OH with allyl bromide (or like reagent) following by coupling with cystamine, as described herein. Further examples of PEG terminal functional groups are described in the detailed description herein below.

According to some embodiments, the hydrophobic dendron comprises a trifunctional moiety having a first bond to a PEG polymer, a second bond to a labeling moiety selected from a fluorescent dye, a dark quencher and a fluorinated labeling moiety, and a third bond, directly or through a linker and/or branching unit, to a first generation dendron which comprises at least one functional group capable of binding to a further generation or to the enzymatically cleavable hydrophobic end group; and optionally, at least one additional generation which is covalently bound to the first generation or preceding generation, and optionally to a further generation, wherein each of the optional generations comprises at least one functional group capable of binding to the first generation, to a preceding generation, to a further generation, and/or to the enzymatically cleavable hydrophobic end group, each of the bonds being formed directly or through a linker or branching unit.

According to some embodiments, the hybrid polymer further comprises a linker moiety and/or a branching unit, which connects the PEG polymer/labeling moiety to the first generation dendron, and/or forms a part of the first generation, and/or connects between dendron generations. In some embodiments, the linker moiety and/or the branching unit is selected from a group consisting of a substituted or unsubstituted acyclic, cyclic or aromatic hydrocarbon moiety, a heterocyclic moiety, a heteroaromatic moiety or any combination thereof. Each possibility represents as separate embodiment of the present invention.

In some particular embodiments, the linker moiety/branching unit is selected from the group consisting of a substituted arylene, C1-C20 alkylene, C2-C20 alkenylene and C2-C20 alkynylene, each comprising at least one functional group selected from the group consisting of —O—, —S—, —NH—, —C(=O)—, —O—C(=O)—O—, —C(=O)—O—, —C(=O)—NH—, —NH—C(=O)—

—NH—, —NH—C(=O)—O—, —S(=O)—, —S(=O)—O—, —PO(=O)—O—, —C=C—, —C≡C—, —(CH$_2$)$_t$— wherein t is an integer of 1-10, and any combination thereof. In one currently preferred embodiment, the linker moiety/branching unit is a substituted arylene. The linker moiety/branching unit may be positioned between the labeling moiety and the first generation dendron, or between the PEG and the first generation dendron, or may form a part of the first generation dendron, or alternatively may be positioned at one or more intermediary generations of the dendron. In one currently preferred embodiment, the linker moiety/branching unit is a substituted arylene which is positioned between the labeling moiety and the first generation dendron. The branching unit may in some cases impart functionality (e.g., UV absorbance or other desired properties). Each possibility represents a separate embodiment of the present invention.

According to certain embodiments, each generation of the hydrophobic dendron comprises a linear or branched C1-C20 alkylene, C2-C20 alkenylene, C2-C20 alkynylene or arylene moiety which is substituted at each end with a group selected from the group consisting of —O—, —S—, —NH—, —C(=O)—, —C(=O)—O—, —O—C(=O)—O—, —C(=O)—NH—, —NH—C(=O)—NH—, —NH—C(=O)—O—, —S(=O)—, —S(=O)—O—, —PO(=O)—O—, and any combination thereof. Each possibility represents as separate embodiment of the present invention.

According to other embodiments, each generation of the dendron is derived from a compound selected from the group consisting of HX—CH$_2$—CH$_2$—XH, HX—(CH$_2$)$_{1-1}$—CO$_2$H, and HX—CH$_2$—CH(XH)—CH$_2$—XH wherein X is independently at each occurrence NH, S or O. In one currently preferred embodiment, the dendron is derived from a compound selected from the group consisting of HS—CH$_2$—CH$_2$—OH, HS—(CH$_2$)$_{1-3}$—CO$_2$H and HS—CH$_2$—CH(OH)—CH$_2$—OH. Each possibility represents as separate embodiment of the present invention.

The hydrophobic dendron of the present invention comprises a preferred number of generations in the range of 0 to 5, more preferably 0 to 3. In one embodiment, the hydrophobic dendron is a generation 0 (G0) dendron. In another embodiment, the hydrophobic dendron is a generation 1 (G1) dendron. In another embodiment, the hydrophobic dendron is a generation 2 (G2) dendron. In yet another embodiment, the hydrophobic dendron is a generation 3 (G3) dendron.

Preferred hybrid polymers in accordance with the principles of the present invention are represented by the structure of formula (I). One embodiment of formula (I) is a compound of formula (II). Another embodiment of formula (I) is a compound of formula (IIa). Other examples of hybrids encompassed by formula (I) are hybrids of formula (G0), (G1), (G1'), (G2), (G2') and (G3). Each possibility represents as separate embodiment of the present invention.

Preferred hybrid polymers in accordance with the principles of the present invention are represented by the structure of any of compounds 1C, 1F, 8C, 8F, 12a, 12b, 13a, 13b, 14a, 14b, 15a, 15b, 16a, 16b, 18 or 20. Each possibility represents a separate embodiment of the present invention.

The structures of all of these derivatives and their components are depicted in the detailed description.

In another aspect, the present invention provides a method of delivering the amphiphilic hybrid system of the present invention, comprising the step of contacting the amphiphilic hybrid delivery system with an enzyme to induce cleavage of the enzymatically cleavable hydrophobic end group, thereby disassembling the micelle.

In another aspect, the present invention provides a kit for delivering the amphiphilic delivery system comprising in one compartment the amphiphilic delivery system and in a second compartment an enzyme capable of cleaving the enzymatically cleavable hydrophobic end group so as to disassemble the micelle.

In another embodiment, the present invention provides a method of monitoring enzymatic activity in a biological system, the method comprising the step of contacting the biological system with the delivery system according to the present invention, and monitoring said enzymatic activity by fluorescence or $^{19}$F-magnetic resonance (MR).

In yet another embodiment, the present invention relates to the use of the hybrid delivery system as described herein, wherein the labeling moiety is a fluorinated labeling moiety, as $^{19}$F-magnetic resonance (MR) probe for $^{19}$F-MR imaging.

The present invention will be more fully understood from the following figures and detailed description of the preferred embodiments thereof.

BRIEF DESCRIPTION OF THE DRAWINGS

FIG. 2: (a) DLS data for hybrids 1F and 1C (160 μM) indicate the formation of micelles with diameters of ~17 nm that decreased to ~6 nm after enzymatic activation by PLE. TEM images of micelles of (b) hybrid 1F and (c) hybrid 1C.

FIG. 19: Schematic illustration of labeled enzyme-responsive hybrids as $^{19}$F magnetic probes and their assembly into micelles. The hybrids contain non-cleavable fluorine containing probes on the polymer. At the assembled state, aggregation of the hydrophobic fluorinated groups at the core of the micelles results in extremely short T$_2$ relaxation time, leading to an OFF state. Upon enzymatic activation, the mobility of the fluorinated hydrophilic polymer increases and its magnetic resonance signal is turned ON.

DETAILED DESCRIPTION OF THE PRESENT INVENTION

Figure 1A:
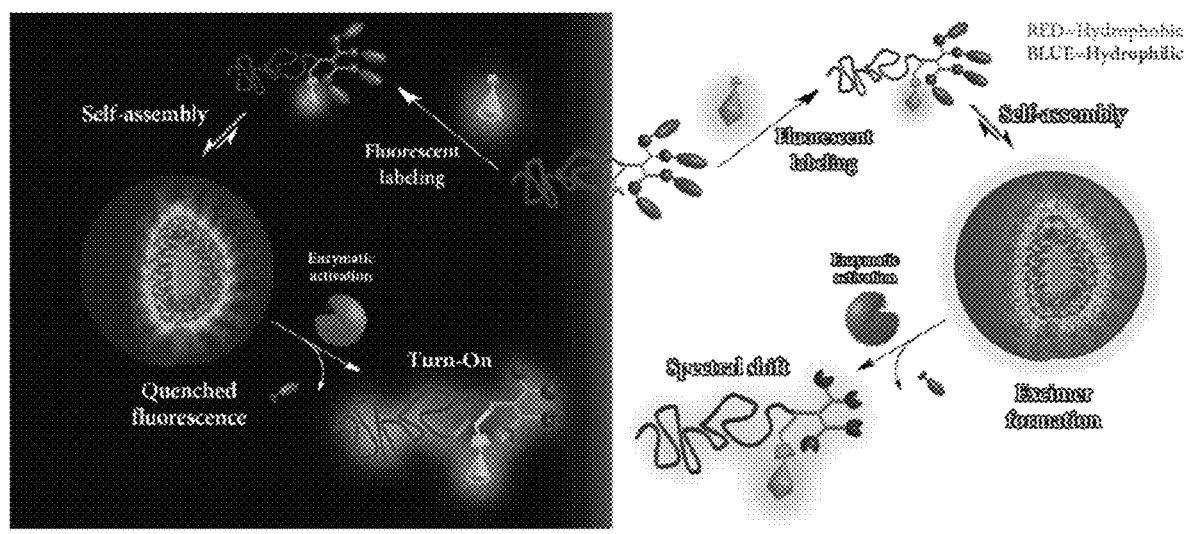
FIG. 1A: Schematic illustration of labeled enzyme-responsive hybrids and their assembly into micelles with quenched (left) or shifted (right) fluorescence emissions. Upon enzymatic activation, the polymeric hybrids become hydrophilic and the structural changes are translated into spectral responses as the labeling dyes regain their intrinsic fluorescence.
Figure 1B:
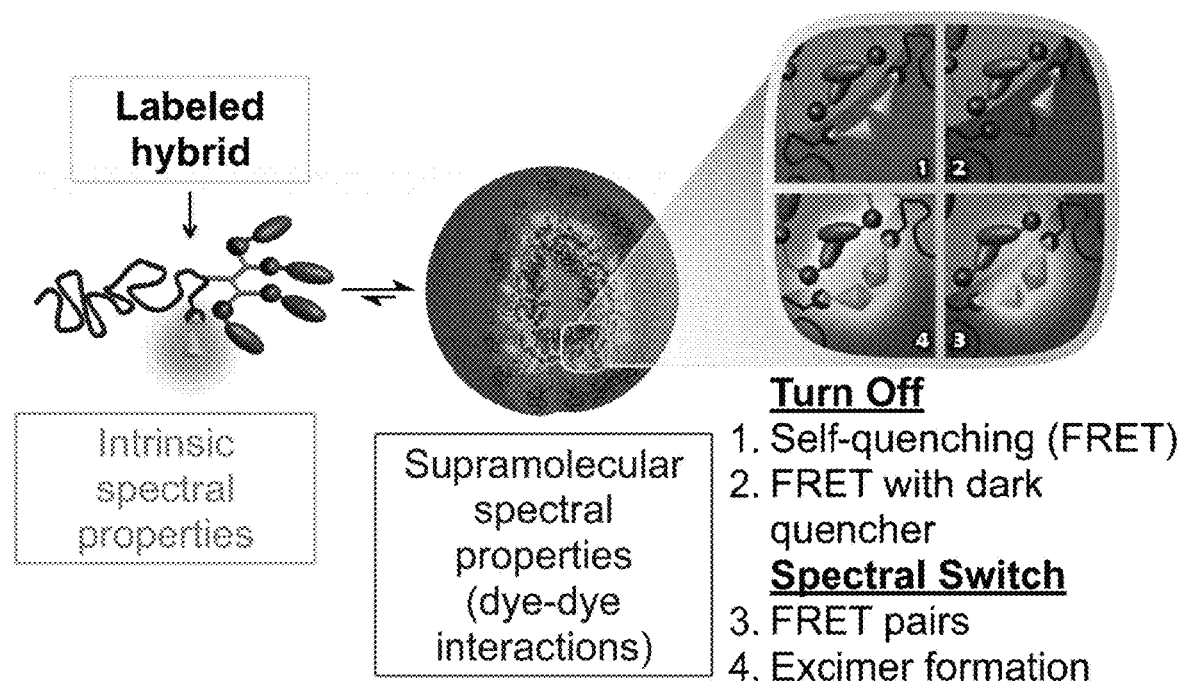
FIG. 1B: Schematic illustration of several embodiments of self-assembly leading to altered supramolecular fluorescent properties.

PEG-dendron Hybrids:

The present invention provides hybrid polymers comprising: (i) a hydrophilic polyethylene glycol (PEG) polymer; (ii) a hydrophobic dendron, the dendron comprising at least one enzymatically cleavable hydrophobic end group that is covalently attached to the dendron; and (ii) at least one labeling moiety selected from a fluorescent dye (or combinations of fluorescent dyes), a dark quencher, combinations of a fluorescent dye and a dark quencher, and a fluorinated labeling moiety. The PEG polymer, hydrophobic dendron and labeling moiety are covalently attached, directly or through a multi-functional moiety.

The present invention further provides an amphiphilic delivery system in micellar form, comprising at least one hybrid polymer, as described above. According to the principles of the present invention, the micelle disassembles upon enzymatic cleavage of the hydrophobic end group to elicit a change in the signal afforded by the labeling moiety (either fluorescence or $^{19}$F-magnetic resonance). Monitoring of the differentials signals in the assembled vs. unassembled state of the micelle by fluorescence imaging or magnetic resonance (MR) provides useful diagnostic information about the location of the hybrid delivery system (e.g., in a biological sample such as a human subject), as well as about the enzymatic activity that is responsible for the micellar disassembly. The hybrids of the present invention thus provide powerful tools, especially in the medical field as diagnostic/prognostic tools as well as in imaging technology. Furthermore, these hybrids can be self-assembled into therapeutic drug delivery platforms that can self-report their location and degree of activation.

In one aspect of the present invention, the modular design of the conjugates of the present invention is based on labeling enzyme responsive PEG-dendron hybrids with a labeling moiety which can either be a fluorescent labeling moiety or a fluorinated labeling moiety. In one embodiment, the labeling moiety is a fluorescent labeling moiety based on a single fluorescent dye (either self-quenching or excimer-forming), a combination of fluorescent dyes (FRET pairs), or a combination of a fluorescent dye and a dark quencher. In one embodiment, the labeling moiety is present at the focal point between the PEG and the dendron. It was hypothesized that in the micellar form the dyes will be closely packed at the interface between the PEG shell and the hydrophobic core. This spatial proximity should lead to supramolecular dye-dye interactions and hence the micelles are expected to have different fluorescence spectrum compared with the intrinsic properties of the dyes. Upon enzymatic cleavage of the hydrophobic end-groups, the micelles disassemble into hydrophilic hybrids that diffuse away from each other. As the distances between the labeled hybrids increase, the non-assembled dyes are expected to regain their intrinsic fluorescence, thus generating a spectral response.

Any fluorescent dyes/dark quenchers and combinations thereof may be used in the context of the present invention. For example, the fluorescent dye and/or dark quencher may be selected from the group consisting of a coumarin, a cyanine dye, an azo dye, an acridine, a fluorone, an oxazine, a phenanthridine, a naphthalimide, a rhodamine, a benzo-pyrone, a perylene, a benzanthrone, and a benzoxanthrone. Each possibility represents a separate embodiment of the present invention. In some representative embodiments, the fluorescent dye is or is the residue of a compound selected from the group consisting of Coumarin, Fluorescein, Cyanine 3 (Cy3), Cyanine 5 (Cy5), Cyanine 7 (Cy7), Alexa dyes, bodipy derivatives, (E)-2-(4-(phenyldiazenyl)phenoxy)acetic acid, 3-(3',3'-dimethyl-6-nitrospiro [chromene-2,2'-indolin]-1'-yl)propanoate (Spiropyran), 3,5-dihydroxy-benzoate and (E)-2-(4-(phenyldiazenyl)phenoxy)acetic acid.

A dark quencher is a substance that absorbs excitation energy from a fluorophore and dissipates the energy as heat.

Dark quenchers are used in molecular biology in conjunction with fluorophores. When the two are close together, such as in an assembled micelle as described herein, the fluorophore's emission is suppressed.

Specific hybrids comprising fluorescent dyes or dark quenchers are represented by the structure of any of compounds 1C, 1F, 8C, 8F, 12a, 12b, 13a, 13b, 14a, 14b, 15a, 15b, 16a, 16b and 18, the structures of which are depicted in the Experimental Section hereinbelow. In another aspect, the labeling moiety is a fluorinated labeling moiety, which functions as a magnetic resonance (MR) probe capable of turning on a $^{19}$F-MR signal. According to the principles of the present invention, the hybrids are designed such that the $^{19}$F-MR signal is turned ON upon enzymatic activation and micelle disassembly, as the fluorinated derivatives become more hydrophilic and their mobility and $T_2$ relaxation increase. Conversely, the hybrids are expected to be turned OFF or quenched upon micelle assembly. A specific hybrid comprising a $^{19}$F-MR probe is a compound of formula 20, the structure of which is depicted in the Experimental Section hereinbelow.

A "dendron" is a hyper-branched monodisperse organic molecule defined by a tree-like or generational structure. In general, dendrons possess three distinguishing architectural features: a linker moiety; an interior area containing generations with radial connectivity to the linker moiety; and a surface region (peripheral region) of terminal moieties. According to certain embodiments, each generation of the hydrophobic dendron comprises a linear or branched C1-C20 alkylene, C2-C20 alkenylene, C2-C20 alkynylene or arylene moiety which is substituted at each end with a group selected from the group consisting of —O—, —S—, —NH—, —C(=O)—, —C(=O)—O—, —O—C(=O)—O—, —C(=O)—NH—, —NH—C(=O)—NH—, —NH—C(=O)—O—, —S(=O)—, —S(=O)—O—, —PO(=O)—O—, and any combination thereof. Each possibility represents as separate embodiment of the present invention.

According to other embodiments, each generation of the dendron is derived from a compound selected from the group consisting of HX—CH$_2$—CH$_2$—XH, HX—(CH$_2$)$_{1-3}$—CO$_2$H, and HX—CH$_2$—CH(XH)—CH$_2$—XH wherein X is independently at each occurrence NH, S or O. In one currently preferred embodiment, the dendron is derived from a compound selected from the group consisting of HS—CH$_2$—CH$_2$—OH, HS—(CH$_2$)$_{1-3}$—CO$_2$H and HS—CH$_2$—CH(OH)—CH$_2$—OH. Each possibility represents as separate embodiment of the present invention.

The hydrophobic dendron of the present invention comprises a preferred number of generations in the range of 0 to 5, more preferably 0 to 3. In one embodiment, the hydrophobic dendron is a generation 0 (G0) dendron. In another embodiment, the hydrophobic dendron is a generation 1 (G1) dendron. In another embodiment, the hydrophobic dendron is a generation 2 (G2) dendron. In yet another embodiment, the hydrophobic dendron is a generation 3 (G3) dendron.

According to some embodiments, the hybrid polymers further comprises a linker moiety and/or a branching unit which connects the PEG polymer/labeling moiety to the first generation dendron, and/or forms a part of the first generation, and/or connects between dendron generations. In one embodiment, the linker moiety and/or the branching unit is selected from a group consisting of a substituted or unsubstituted acyclic, cyclic or aromatic hydrocarbon moiety, heterocyclic moiety, a heteroaromatic moiety or any combination thereof. Each possibility represents as separate embodiment of the present invention. In one currently preferred embodiment, the linker moiety/branching unit is a substituted arylene which may be positioned between the PEG and the first generation or may form a part of the first generation, or alternatively may be positioned at one or more intermediary generations of the dendron, or alternatively may be positioned between the moiety comprising the fluorescent dye and the first generation dendron. The branching unit may in some cases impart functionality (e.g., UV absorbance or other desired properties). Each possibility represents a separate embodiment of the present invention.

According to various embodiments, each of the linker moiety/branching unit may be connected through a functional group selected from the group consisting of —O—, —S—, —NH—, —C(=O)—, —C(=O)—O—, —OC(=O)—O—, —C(=O)—NH—, —NH—C(=O)—NH—, —NH—C(=O)—O—, —S(=O)—, —S(=O)—O—, —PO(=O)—O—, —C=C—, —C≡C—, —(CH$_2$)$_t$— wherein t is an integer of 1-10, and any combination thereof. One representative example of a functional group linking the PEG to the dendron is —S(CH$_2$)$_t$—NH—. Each possibility represents as separate embodiment of the present invention.

The modular design of the hybrid delivery systems of the present invention provides control over the disassembly of the micelle and release rate of the hydrophobic end groups and/or encapsulated cargo. This can be achieved by adjusting the structural features of the nanocarriers (such as length of PEG polymer, dendron generation, number of enzymatically cleavable moieties, linkage chemistry and polymer/dendron weight ratio) as well as enzymatic-tuning parameters (e.g., enzyme specificity, amount of enzyme and incubation time.

The architecture of the hybrids of the present invention requires three orthogonal functional groups to allow conjugation of the PEG, dendron, and labeling moiety. Thus, in some embodiments, the multi-functional moiety is a trifunctional moiety that is capable of attaching to the hydrophobic dendron, the PEG polymer, and the labeling moiety. According to some embodiments of the present invention, the trifunctional group comprises one functional group capable of bonding to the PEG moiety (directly or through a linker), a second functional moiety capable of bonding to the dendron (directly or through a linker), and a third functional group capable of bonding to the labeling moiety. In a currently preferred embodiment, the trifunctional group is advantageously situated at a focal group, between the PEG moiety and the dendron. As such, the hybrid of the invention, may generally be represented by the structure:

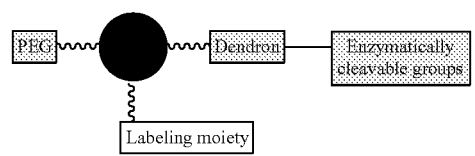

wherein

represents the core of the trifunctional moiety, and each ⁓⁓⁓ independently represents a functional group on the trifunctional moiety linking the PEG, dendron and labeling moiety, each directly or through functional groups/linkers as described herein. The dendron comprises a multiplicity of enzymatically cleavable groups at its terminus, as described herein.

The hybrid polymer of the present invention may generally be represented by the structure of formula (I):

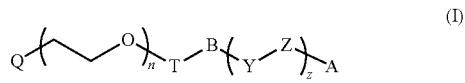

wherein

Q is selected from the group consisting of OR wherein is H or a C1-C4 alkyl (e.g., methyl); $NH_2$, SH and COOH;

T is absent or is a functional group selected from the group consisting of —$(CH_2)_t$—X—$(CH_2)_t$—X—, —X—$(CH_2)_t$—X—, —$(CH_2)_t$— wherein X is independently at each occurrence selected from O, S and NH, and t is independently at each occurrence 1-10; —O—, —S—, —NH—, —C(=O)—, —C(=O)—O—, —O—C(=O)—O—, —C(=O)—NH—, —NH—C(=O)—NH—, —NH—C(=O)—O—, —S(=O)—, —S(=O)—O—, —PO(=O)—O—, —C=C—, —C≡C—, any combination thereof.

B is a trifunctional moiety comprising a labeling moiety covalently attached thereto;

Y is independently at each occurrence absent or is a linker moiety/branching unit;

Z is independently at each occurrence a dendron repeating unit selected from the group consisting of:

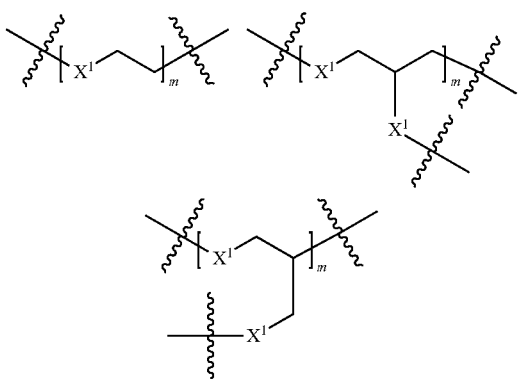

and any combination of the foregoing;

wherein $X^1$ is independently, at each occurrence, selected from the group consisting of O, S and NH;

A represents a multiplicity of hydrophobic end groups conjugated to terminal units of the dendron (as defined hereinbelow) through at least one enzymatically cleavable functional group selected from the group consisting of an ester, an amide, a carbamate, a carbonate, a urea, a sulfate, an amidine, an ether, a phosphate, a phosphoamide, sulfamates, and a trithionate;

n is an integer in the range of 1 to 1,500; and m and z are each an integer of 1 to 15.

In some embodiments, n is an integer in the range of 1 to 1,000.

It is understood that the number of groups (A) will depend on the number of dendron terminal units and the number of functional groups on each dendron terminal group available to form an enzymatically cleavable functional group.

Trifunctional Moiety B

According to some embodiments, the hybrid polymer comprises a trifunctional moiety having a first bond to a PEG polymer, a second bond to a labeling moiety, and a third bond, directly or through a linker or branching unit, to a first generation dendron which comprises at least one functional group capable of binding to a further generation or to said enzymatically cleavable hydrophobic end group; and optionally, at least one additional generation which is covalently bound to said first generation or preceding generation, and optionally to a further generation, wherein each of said optional generations comprises at least one functional group capable of binding to said first generation, to a preceding generation, to a further generation, and/or to said enzymatically cleavable hydrophobic end group, each of said bonds being formed directly or through a linker or branching unit.

The nature of the functional groups on the trifunctional moiety B may vary, depending on the particular hybrid being constructed. According to non-limiting embodiments, the bifunctional moiety may comprise three functional groups selected from the group consisting of —O—, —S—, —NH—, —C(=O)—, —C(=O)—O—, —O—C(=O)—O—, —C(=O)—NH—, —NH—C(=O)—NH—, —NH—C(=O)—O—, —S(=O)—, —S(=O)—O—, —PO(=O)—O—, and any combination thereof. Those functional groups may be linked to a core structure which can be, e.g., an amino acid, a C1-C20 alkylene, a C2-C20 alkenylene, a C2-C20 alkynylene an arylene, etc.

In one currently preferred embodiment, the trifunctional moiety B is an amino acid capable of attaching to the hydrophobic dendron, the PEG polymer, and the labeling moiety through its carboxyl group, amino group, and side chain. Suitable amino acids are those that contain, in addition to the amino and carboxy functionalities, an additional functional group (e.g., on the side chain), together defining a trifunctional moiety. The amino acid may be an alpha-amino acid, a beta-amino acid, a gamma-amino acid, a delta-amino acid, etc. In some embodiments, the the bifunctional moiety is an alpha-amino acid selected from the group consisting of lysine, aspartic acid, glutamic acid, tyrosine, asparagine, serine, homoserine, cysteine, homocysteine, glutamine, threonine, ornithine, citrulline, and arginine.

In one embodiment, the amino acid is an alpha amino acid represented by the structure:

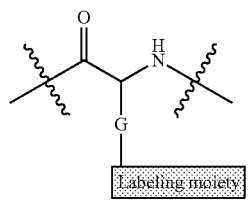

wherein G is the amino acid side chain, which comprises a functional group enabling its attachment to the labeling moiety.

In one currently preferred embodiment, the amino acid is lysine, and the trifunctional group may generally be represented by the structure:

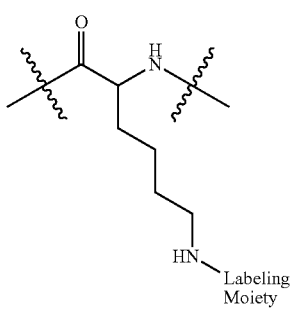

Labeling Moiety

Linkers/Branching Moiety

The linking group T, when present, connects the PEG polymer to the functional group B. In one embodiment, T is absent and the PEG is bound directly to the trifunctional moiety B. In other embodiments, T is present and may be any functional moiety selected from the group consisting of —(CH$_2$)$_t$—X—(CH$_2$)$_t$—X—, —X—(CH$_2$)$_t$—X—, —(CH$_2$)$_t$— wherein X is independently at each occurrence selected from O, S and NH, and t is independently at each occurrence 1-10; —O—, —S—, —NH—, —C(=O)—, —C(=O)—O—, —O—C(=O)—O—, —C(=O)—NH—, —NH—C(=O)—NH—, —NH—C(=O)—O—, —S(=O)—, —S(=O)—O—, —PO(=O)—O—, —C=C—, —C≡C—, any combination thereof.

In currently preferred embodiment, T is —(CH$_2$)$_3$—S—(CH$_2$)$_2$—NH—. This group may be introduced by functionalizing OR-PEG-OH with an allyl derivative (e.g., allyl halide) followed by coupling with cystamine hydrochloride. In accordance with this embodiment, PEG-T is represented by the structure:

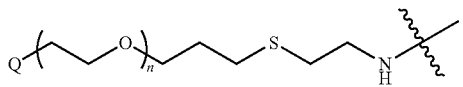

wherein Q, R and n are as defined above. In one embodiment, OR is methoxy. This functional is sometimes abbreviated as: MeO-PEG-NH—.

According to some embodiments, the hybrid delivery system further comprises a linker moiety and/or a branching unit (designated herein "Y"), or a multiplicity of such units, each of which connect(s) the trifunctional moiety B to the first generation dendron, and/or forms a part of the first generation, and/or connects between dendron generations. In one embodiment, the linker moiety and/or the branching unit is selected from a group consisting of a substituted or unsubstituted acyclic, cyclic or aromatic hydrocarbon moiety, heterocyclic moiety, a heteroaromatic moiety or any combination thereof. Each possibility represents as separate embodiment of the present invention. Specific examples of linker moieties/branching units, useful for this invention include but are not limited to, arylenes, which may be substituted with one or more hydroxyls (e.g., phenols), trimethylolpropane, glycerine, pentaerythritol, polyhydroxy phenols such as phloroglucinol, propylene glycol, tri-substituted alkylamines, diethylenetriamine, triethylenetetramine, diethanolamine, triethanolamine, amino carboxylic acids, such as ethylenediaminetetraacetic (EDTA) and porphyrin, ethylene glycol, ethylenediamine di-substituted alkylamines, diethylenetriamine, triethylenetetramine, diethanolamine, fumaric, maleic, phthalic, malic acid, 6-aminohexanol, 6-mercaptohexanol, 10-hydroxydecanoic acid, 1,6-hexanediol, beta-alanine, 2-aminoethanol, 2-aminoethanethiol, 5-aminopentanoic acid, and 6-aminohexanoic acid among others. Each possibility represents as separate embodiment of the present invention. In one currently preferred embodiment, the linker moiety/branching is an unsubstituted or substituted arylene or phenol which may be positioned between the PEG and the first generation or may form a part of the first generation, or alternatively may be positioned at one or more intermediary generations of the dendron. The linker/branching unit may further provide additional functionality to the hybrid delivery system (e.g., UV absorption). According to various embodiments, each of the linker moiety/branching unit may be connected to the PEG or to other dendron generations through a functional group selected from the group consisting of —O—, —S—, —NH—, —C(=O)—, —C(=O)—O—, —OC(=O)—O—, —C(=O)—NH—, —NH—C(=O)—NH—, —NH—C(=O)—O—, —S(=O)—, —S(=O)—O—, —PO(=O)—O—, —C=C—, —C≡C—, —(CH$_2$)$_t$— wherein t is an integer of 1-10, and any combination thereof. Each possibility represents as separate embodiment of the present invention.

The group Y may be present once at the focal point of the dendron, or may be present multiple times as branching units. In one embodiment, the branching group Y is an arylene which serves as a branching group for the dendron arms. One particular embodiment uses a linker moiety/branching unit derived from 3,5-dihydroxybenzoic acid.

Dendron Repeating Units:

According to other embodiments, the terminal repeating unit of said dendron is represented by any of the following structures:

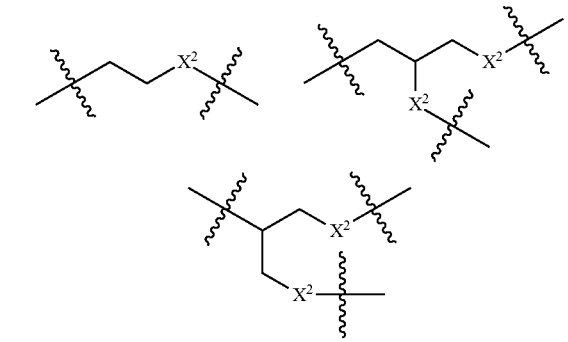

wherein X$^2$ has the same meaning as X$^1$.

According to yet other embodiments, the hydrophobic end group A is conjugated to the dendron through a functional group represented by the structure:

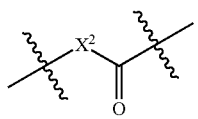

wherein X$^2$ is a part of the terminal repeating unit of said dendron and C(=O) is part of hydrophobic end group; or wherein X$^2$ is part of the hydrophobic end group and C(=O) is a part of the terminal repeating unit of said dendron, or wherein X$^2$—C(=O) are part of the hydrophobic end group, or wherein $X^2$—C(=O) is part of the terminal repeating unit of said dendron; and wherein $X^2$ has the same meaning as $X^1$.

Enzymatically Cleavable Hydrophobic End Groups (A)

According to the present invention, the dendron comprises a plurality of enzymatically cleavable hydrophobic end groups.

According to some embodiments, the enzymatically cleavable hydrophobic end group is present at one or more of the terminal repeating units (i.e., terminal generations) of the hydrophobic dendron, and/or in intermediary generations of the dendron. In other embodiments, the enzymatically cleavable hydrophobic end group is present only at the terminal repeating units of the hydrophobic dendron (i.e., the enzymatically cleavable hydrophobic end group is not present in intermediary generations of the dendron).

According to some embodiments, the enzymatically cleavable hydrophobic end group is conjugated to the dendron through an enzymatically cleavable functional group selected from the group consisting of an ester, an amide, a carbamate, a carbonate, a urea, a sulfate, an amidine, an ether, a phosphate, a phosphoamide, sulfamates, and a trithionate. Each possibility represents as separate embodiment of the present invention.

According to some embodiments, the enzymatically cleavable hydrophobic end group is conjugated to the dendron through an amide which is cleavable by an amidase. In one embodiment, the amidase is selected from the group consisting of aryl-acylamidase, aminoacylase, alkylamidase, and phthalyl amidase. Each possibility represents as separate embodiment of the present invention.

According to some embodiments, the enzymatically cleavable hydrophobic end group is conjugated to the dendron through an ester which is cleavable by an esterase. In one embodiment, the esterase is selected from the group consisting of carboxylesterase, arylesterase, and acetylesterase. Each possibility represents as separate embodiment of the present invention.

In other embodiments, the enzymatically cleavable hydrophobic end group is an ester O—C(O)—R or C(O)—OR wherein R is an aliphatic chain of C1-C12 carbon atoms, or an aryl, which is cleavable by esterases. Examples or esters based on octanoic acid and undecanoic acid as describe herein, with each possibility representing a separate embodiment of the present invention. In other embodiments, the enzymatically cleavable hydrophobic end group is an amide —NH—C(O)—R or —C(O)—NH—R wherein R is an aliphatic chain of C1-C12 carbon atoms, or an aryl, which is cleavable by amidases. In one currently preferred embodiment, the enzymatically cleavable hydrophobic end group is phenyl acetate, which is cleaved by esterases. In other currently preferred embodiments, the enzymatically hydrophobic end group is phenylacetamide, which is cleavable by amidases.

According to other embodiments, the enzymatically cleavable hydrophobic end group is cleaved by an enzyme which is (i) present in greater amount at; or (ii) produced in greater quantity at, or (iii) has higher activity in cells near or at a site of disease or infection. Each possibility represents as separate embodiment of the present invention.

As contemplated herein, the term "enzymatic cleavage" covers total or partial cleavage of the enzymatically cleavable hydrophobic end group, i.e., all of the cleavable hydrophobic end group may be hydrolyzed, or only a portion of such groups, by any of the enzymes described herein.

PEG Polymer

The hydrophilic PEG polymer is a currently preferred polymer to prepare the block co-polymer hybrid of the present invention as it is generally recognized as safe for use in food, cosmetics, medicines and many other applications by the US Food and Drug Administration. PEG has beneficial physical and/or chemical properties such as water-solubility, non-toxic, odorless, lubricating, nonvolatile, and non-intrusive which are particularly suitable for pharmaceutical utility.

There are many commercial available derivatives of PEG, all of which may be useful in the present invention. When the PEG is derivatized at both termini, a heterobifunctional PEG is preferably used, i.e., containing orthogonal functional groups that are reactive under different conditions, thereby allowing for selective reactivity on each side. Examples of PEG derivatives that may be used include, but not limited to methoxy PEG-OH (mPEG), amine-terminated PEG (PEG-$NH_2$), carboxylated PEG (PEG-COOH), thiol-terminated PEG (PEG-SH), N-hydroxysuccinimide-activated PEG (PEG-NHS), $NH_2$-PEG-$NH_2$ or $NH_2$-PEG-COOH. Additional non-limiting examples of PEG derivatives that may be used as starting materials are: PEG-azide (for Cu/azide/alkyne click chemistry), PEG-acrylate/acrylamide, PEG-alkyne (for Cu/azide/alkyne click chemistry), PEG-DBCO, PEG-epoxide glycidyl ether, PEG-halide; PEG-hydrazide, PEG-maleimide, PEG-nitrophenyl carbonate (NPC), PEG-orthopyridyl disulfide (PUSS), PEG-silane, PEG-sulfonate (e.g., tosyl, mesyl), PEG-COOR wherein R is an alkyl, etc. Each possibility represents as separate embodiment of the present invention.

These PEG derivatives may be subjected to further chemical modifications and substitutions. For example RU-PEG-OH may be functionalized by allylation followed by thiolation with cystamine to produce RO-PEG-$(CH_2)_3$—S—$(CH_2)_2$—$NH_2$ as a starting material, as described in Scheme 3A hereinbelow.

Thus, according to various embodiments, the PEG is linked to the dendron or the multi-functional moiety through a PEG terminal functional group selected from the group consisting of —$(CH_2)_t$—X—$(CH_2)_t$—X—, —X—$(CH_2)_t$X—, —$(CH_2)_t$— wherein X is independently at each occurrence selected from O, S and NH, and t is independently at each occurrence 1-10; —O—, —S—, —NH—, —C(=O)—, —C(=O)—O—, —O—C(=O)—O—, —C(=O)—NH—, —NH—C(=O)—NH—, —NH—C(=O)—O—, —S(=O)—, —S(=O)—O—, —PO(=O)—O—, —C=C—, —C≡C—, triazolyl, and any combination thereof. Preferably, the PEG is functionalized by the functional group $(CH_2)_3$—S—$(CH_2)_2$—NH— (i.e., the group T in formula (I)).

The PEG may be derivatized by a terminal group Q which is preferably selected from the group consisting of OR wherein is H or a C1-C4 alkyl (e.g., methyl); $NH_2$, SH and COOH. However, other functional groups can advantageously be used, e.g., as targeting moieties to direct the hybrid delivery systems of the present invention to their biological targets.

According to some embodiments, the PEG has an average molecular weight between about 0.5 and 70 kDa. In one currently preferred embodiment, the hydrophilic PEG polymer is an mPEG. In another currently preferred embodiment, the PEG polymer has a molecular weight of about 2 kDa. In another currently preferred embodiment, the PEG polymer has a molecular weight of about 5 kDa. In yet another currently preferred embodiment, the PEG polymer has a molecular weight of about 10 kDa. In yet another currently preferred embodiment, the PEG polymer has a molecular weight of about 20 kDa. In yet another currently preferred embodiment, the PEG polymer has a molecular weight of about 30 kDa. Preferably, the PEG has at least 10 repeating units of ethylene glycol monomers.

In one embodiment, the hybrid polymer of the present invention may generally be represented by formula (II):

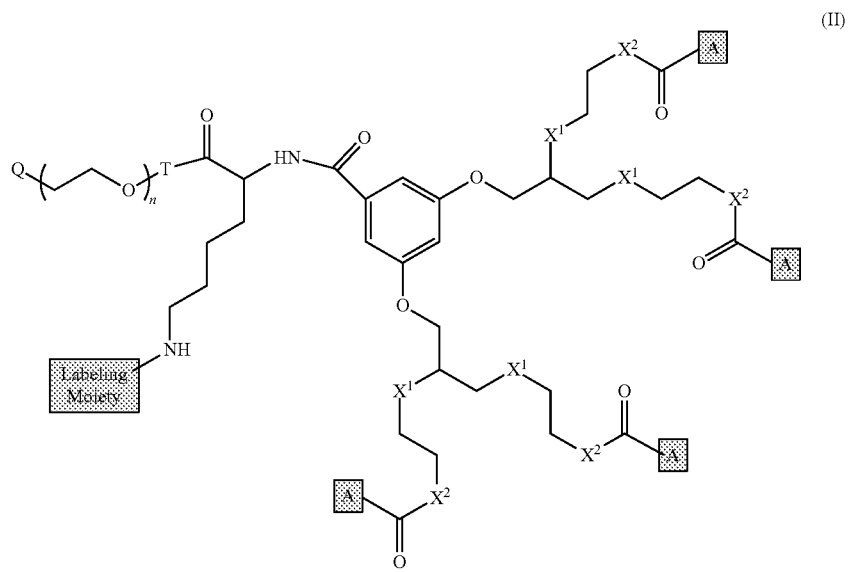

(II)

wherein each $X^1$ and $X^2$ is independently at each occurrence selected from the group consisting of O, S and NH;

Q is selected from the group consisting of OR wherein is H or a C1-C4 alkyl (e.g., methyl); $NH_2$, SH and COOH;

the labeling moiety is selected from a fluorescent dye, a dark quencher and a fluorinated moiety; and n is an integer of 1 to 1,500, preferably 1 to 1,000.

One specific embodiment of formula (II) is represented by the structure of formula (IIa):

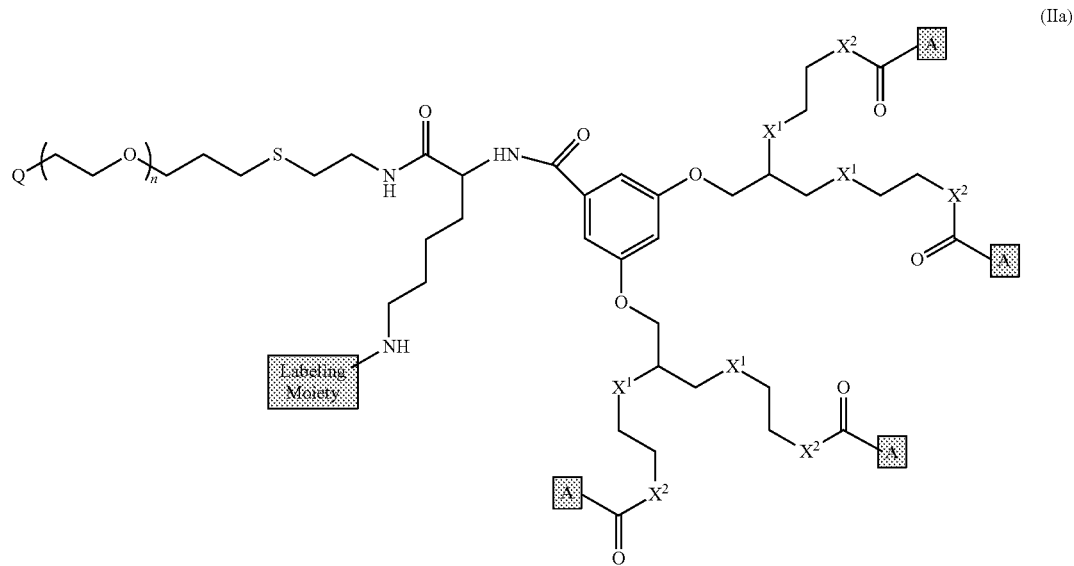

(IIa)

A, alone or together with C(=O) is a hydrophobic end group;

T is absent or is a functional group selected from the group consisting of
—$(CH_2)_t$—X—$(CH_2)_t$—X—, —X—$(CH_2)_t$—X—, —$(CH_2)_t$— wherein X is independently at each occurrence selected from O, S and NH, and t is independently at each occurrence 1-10; —O—, —S—, —NH—, —C(=O)—, —C(=O)—O—, —O—C(=O)—O—, —C(=O)—NH—, —NH—C(=O)—NH—, —NH—C(=O)—O—, —S(=O)—, —S(=O)—O—, —PO(=O)—O—, —C=C—, —C≡C—, any combination thereof;

Other examples of the hybrid polymers of formula (I) include, but are not limited to, any one or more of the following structures:

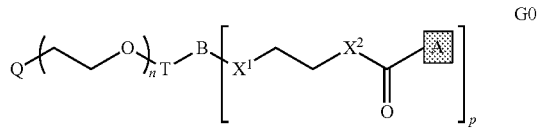

G0

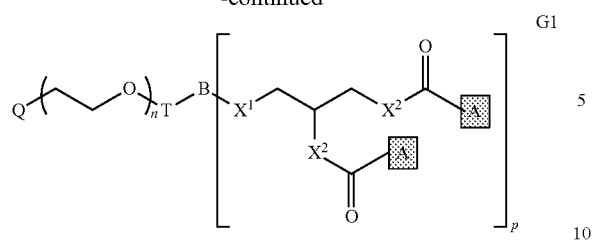
G1
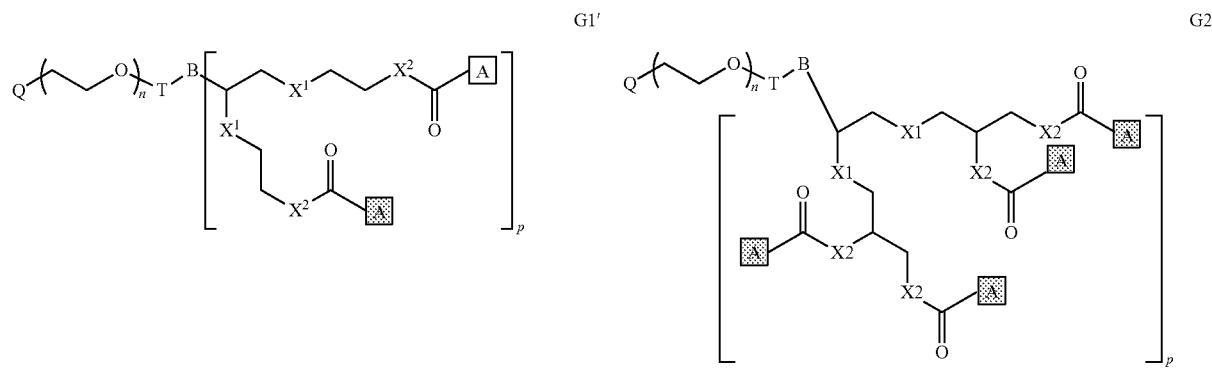
G1'    G2
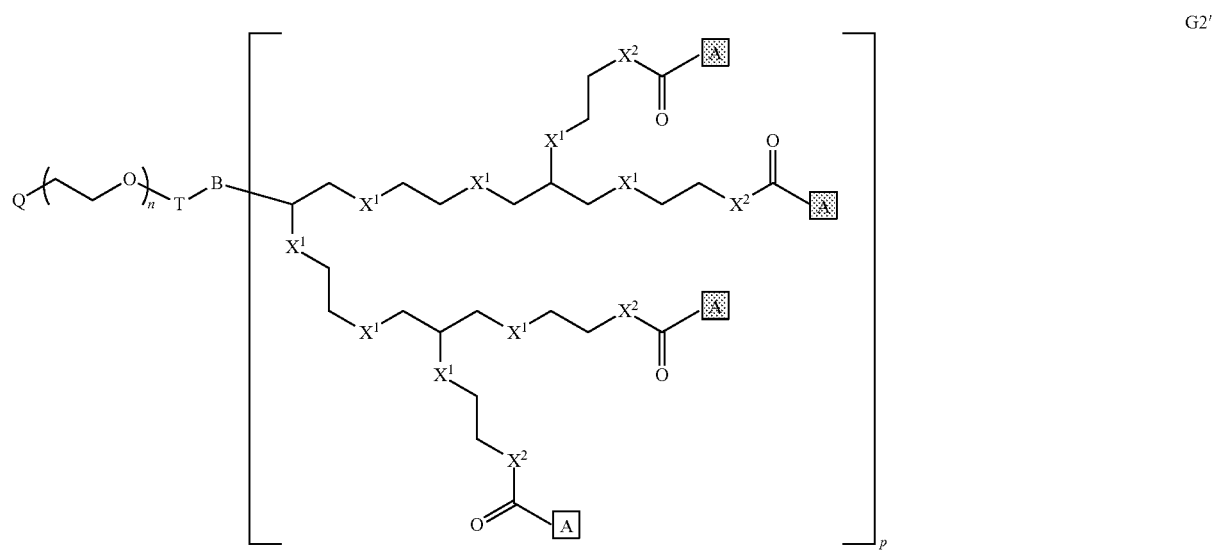
G2'

G3

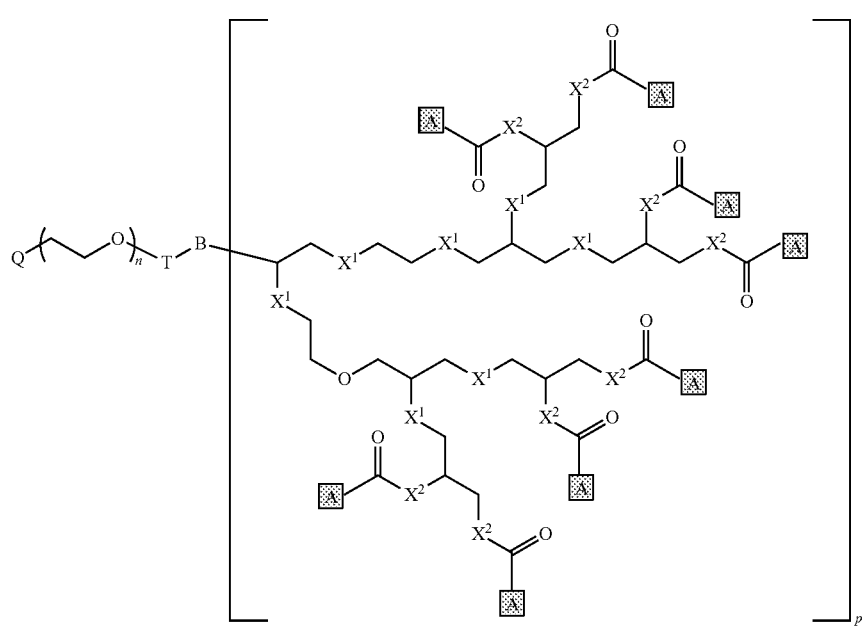

wherein each $X^1$ and $X^2$ is independently at each occurrence selected from the group consisting of O, S and NH;

Q is selected from the group consisting of OR wherein is H or a C1-C4 alkyl (e.g., methyl); $NH_2$, SH and COOH A, alone or together with C(=O) is a hydrophobic end group;

B is a bifunctional moiety comprising a labeling moiety covalently attached thereto;

p is 1, 2, 3, 4 or 5; and n is an integer of 1 to 1,500.

In some embodiments, n is an integer in the range of 1 to 1,000.

Each possibility represents as separate embodiment of the present invention.

Also contemplated are analogues of compounds of formulae (I), (II), (IIa), G0, G1, G1', G2, G2', and G3 wherein the linkage of A to —$X^2$—C(=O)— is reversed, i.e., the compounds incorporate the following moiety:

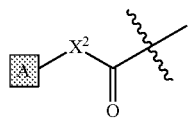

wherein $X^2$ is part of the hydrophobic end group A or part of the dendron.

In some embodiments, the micelle has an average particle size of less than about 100 nm, preferably about 50 nm or lower, more preferably about 10 nm to 50 nm, and most preferably about 10 nm to 20 nm. Each possibility represents as separate embodiment of the present invention.

A diagnostic agent refers to a chemical or biological molecule used to identify a disease, disorder or medical condition as well as monitor treatment effects. Diagnostic agents include radiopharmaceuticals, contrast agents for use in imaging techniques, allergen extracts, activated charcoal, different testing strips (e.g., cholesterol, ethanol, and glucose), pregnancy test, breath test with urea $^{13}$C, and various stains/markers. Each possibility represents as separate embodiment of the present invention.

The term "derived from" as used herein means a moiety that is derived from an active compound (i.e., any of the biologically or diagnostically active compounds described herein) and that is incorporated into the hybrid systems of the present invention. A derivative of an active moiety may be formed, e.g., by removing one or more of the atoms of said compound or adding one or more atoms or functional groups so as to chemically conjugate it to the dendron.

Chemical Definitions

The term "alkyl" used herein alone or as part of another group denotes a saturated aliphatic hydrocarbon, including straight-chain and branched-chain alkyl groups. In one embodiment, the alkyl group has 1-12 carbons designated here as C1-C12-alkyl. In another embodiment, the alkyl group has 1-4 carbons designated here as C1-C4-alkyl. Examples of alkyl groups include, but are not limited to, methyl, ethyl, propyl, isopropyl, n-butyl, isobutyl, sec-butyl, t-butyl, and the like.

The term "aryl" used herein alone or as part of another groups denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like.

The term "C1-C20 alkylene" used herein alone or as part of another group denotes a bivalent radicals of 1 to 20 carbons, which is bonded at two positions connecting together two separate additional groups (e.g., $CH_2$). Examples of alkylene groups include, but are not limited to —($CH_2$)—, —($CH_2$)$_2$—, —($CH_2$)$_3$—, —($CH_2$)$_4$—, etc.

The term "C2-C20 alkenylene" used herein alone or as part of another group denotes a bivalent radical of 2 to 20 carbons which contains at least one double bond, which is bonded at two positions connecting together two separate additional groups (e.g., —CH=CH—).

The term "C2-C20 alkynylene" used herein alone or as part of another group denotes a bivalent radicals of 2 to 20 carbons containing at least one triple bond, which is bonded at two positions connecting together two separate additional groups (e.g., —C≡C—).

The term "arylene" denotes a bivalent radicals of aryl, which is bonded at two positions connecting together two separate additional groups. The term "acyclic hydrocarbon" used herein denotes to any linear or branched, saturated and mono or polyunsaturated carbon atoms chain, or the residue of such compound after it has chemically bonded to another molecule. Preferred are acyclic hydrocarbon moieties containing from 1 to 20 carbon atoms. The acyclic hydrocarbon of the present invention may comprise one or more of an alkyl, an alkenyl, and an alkynyl moieties. Examples of acyclic hydrocarbon include, but are not limited to, n-propyl, isopropyl, n-butyl, sec-butyl, isobutyl and tert-butyl, n-pentyl, n-hexyl, vinyl, allyl, butenyl, pentenyl, ropargyl, butynyl, pentynyl, and hexynyl. Each possibility represents as separate embodiment of the present invention.

The term "cyclic hydrocarbon" generally refers to a C3 to C8 cycloalkyl or cycloalkenyl which includes monocyclic or polycyclic groups. Non-limiting examples of cycloalkyl groups are cyclopropyl, cyclobutyl, cyclopentyl, cyclohexyl or cycloheptyl. The cycloalkyl group can be unsubstituted or substituted with any one or more of the substituents defined above for alkyl.

The term "aromatic hydrocarbon" used herein denotes to an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. Each possibility represents as separate embodiment of the present invention. The aryl group can be unsubstituted or substituted through available carbon atoms with one or more groups defined hereinabove for alkyl.

The terms "heterocyclic" or "heterocyclyl" used herein alone denote a five-membered to eight-membered rings that have 1 to 4 heteroatoms, such as oxygen, sulfur and/or nitrogen. These five-membered to eight-membered rings can be saturated, fully unsaturated or partially unsaturated. Preferred heterocyclic rings include piperidinyl, pyrrolidinyl, pyrrolinyl, pyrazolinyl, pyrazolidinyl, piperidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. Each possibility represents as separate embodiment of the present invention. The heterocyclyl group can be unsubstituted or substituted through available atoms with one or more groups defined hereinabove for alkyl.

The term "heteroaryl" used herein denotes a heteroaromatic system containing at least one heteroatom ring atom selected from nitrogen, sulfur and oxygen. The heteroaryl generally contains 5 or more ring atoms. The heteroaryl group can be monocyclic, bicyclic, tricyclic and the like. Also included in this expression are the benzoheterocyclic rings. If nitrogen is a ring atom, the present invention also contemplates the N-oxides of the nitrogen containing heteroaryls. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. Each possibility represents as separate embodiment of the present invention. The heteroaryl group may optionally be substituted through available atoms with one or more groups defined hereinabove for alkyl.

Any of the moieties described herein (e.g., alkylene, alkenylene, alkynylene, arylene, acyclic and cyclic hydrocarbons, heterocyclic and heteroaromatic moieties) may be unsubstituted, or substituted with one or more substituents selected from the group consisting of halogen, hydroxy, alkoxy, aryloxy, alkylaryloxy, heteroaryloxy, oxo, cycloalkyl, phenyl, heteroaryl, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, $C_1$ to $C_4$ alkylthio, arylthio, or $C_1$ to $C_4$ alkylsulfonyl groups. Any substituent can be unsubstituted or further substituted with any one of these aforementioned substituents. Each possibility represents as separate embodiment of the present invention.

All stereoisomers, optical and geometrical isomers of the compounds of the instant invention are contemplated, either in admixture or in pure or substantially pure form. The compounds of the present invention can have asymmetric centers at any of the atoms. Consequently, the compounds can exist in enantiomeric or diastereomeric forms or in mixtures thereof. The present invention contemplates the use of any racemates (i.e., mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, 1,L or d,1, D,L. In addition, several of the compounds of the invention contain one or more double bonds. The present invention intends to encompass all structural and geometrical isomers including cis, trans, E and Z isomers, independently at each occurrence.

One or more of the compounds of the invention, may be present as a salt. The term "salt" encompasses both basic and acid addition salts, including but not limited to phosphate, dihydrogen phosphate, hydrogen phosphate and phosphonate salts, and include salts formed with organic and inorganic anions and cations. Furthermore, the term includes salts that form by standard acid-base reactions of basic groups and organic or inorganic acids. Such acids include hydrochloric, hydrofluoric, hydrobromic, trifluoroacetic, sulfuric, phosphoric, acetic, succinic, citric, lactic, maleic, fumaric, cholic, pamoic, mucic, D-camphoric, phthalic, tartaric, salicyclic, methanesulfonic, benzenesulfonic, p-toluenesulfonic, sorbic, picric, benzoic, cinnamic, and like acids. Additional salts of the conjugates described herein may be prepared by reacting the parent molecule with a suitable base, e.g., NaOH or KOH to yield the corresponding alkali metal salts, e.g., the sodium or potassium salts. Additional basic addition salts include ammonium salts ($NH_4$), substituted ammonium salts, Li, Ca, Mg, salts, and the like.

Uses

The molecular assemblies described herein are useful as diagnostic probes for monitoring specific enzymatic activity and/or as probes capable of reporting the degree and location of activation.

Potential uses of the hybrid delivery systems described herein include advanced enzymatically activated fluorescent imaging probes and smart drug delivery platforms, as well as or $^{19}F$ probes for turn-on of $^{19}F$-magnetic resonance signal ($^{19}F$-MR probes) for diagnostic and monitoring purposes.

In one aspect, the present invention provides a method of delivering the amphiphilic hybrid system of the invention comprising the step of contacting the amphiphilic hybrid delivery system with an enzyme to induce cleavage of the enzymatically cleavable hydrophobic end group, thereby disassembling the micelle.

In another aspect, the present invention provides a method of monitoring enzymatic activity in a biological system, the method comprising the step of contacting the biological system with a hybrid delivery system according to claims 1, and monitoring said enzymatic activity by fluorescence or $^{19}$F-magnetic resonance (MR).

In another aspect, the present invention relates to the use of the hybrid delivery system according to claim 1 wherein the labeling moiety is a fluorescent labeling moiety, as $^{19}$F-magnetic resonance (MR) probe for $^{19}$F-MR imaging.

As used herein, the term "contacting" refers to bringing in contact with the amphiphilic hybrid delivery system of the present invention. Contacting can be accomplished to cells or tissue cultures, or to living organisms, for example humans. In one embodiment, the present invention encompasses contacting the amphiphilic hybrid delivery system of the present invention with a human subject.

As used herein, the term "contacting the amphiphilic hybrid delivery system" may be ex-vivo on a surface, on a device, in cell/tissue culture dish, in food and water, as well as in-vivo, among others. Alternatively, the contact may be in the body of a human or non-human subject.

Kits

In another aspect, the present invention provides a kit for delivering the amphiphilic hybrid system comprising in one compartment the amphiphilic hybrid system, and in a second compartment an enzyme capable of cleaving the enzymatically cleavable hydrophobic end group so as to disassemble the micelle.

The kit may further include appropriate buffers and reagents known in the art for administering/contacting the compartments listed above to a host cell or a host organism. The amphiphilic hybrid delivery system and the enzyme may be provided in solution and/or in lyophilized form. When the enzyme is in a lyophilized form, the kit may optionally contain a sterile and physiologically acceptable reconstitution medium such as water, saline, buffered saline, and the like.

According to some embodiments, associated with such compartments may be various written materials such as instructions for use.

The examples hereinbelow are presented in order to more fully illustrate some embodiments of the invention. They should, in no way be construed, however, as limiting the broad scope of the invention. One skilled in the art may readily devise many variations and modifications of the principles disclosed herein without departing from the scope of the invention.

EXAMPLES

Example 1—Smart Micelles Containing Tunable Fluorescent Probes

The amino acid lysine with two orthogonal amine protecting groups was chosen as the tri-functional junction since selective deprotection should allow simple synthesis of the dendron from α-amine and fluorescent labeling of the ε-amine. Fluorescein (F) was chosen as the Turn-On dye, due to its small Stokes shift and known self-quenching at high loading. 7-Diethylamino-3-carboxy coumarin (C) was utilized as the spectral shift dye as coumarins can form excimers with red-shifted emission. Two esterase-responsive labeled hybrids, 1F and 1C, bearing four enzymatically cleavable hydrophobic end-groups and either fluorescein or coumarin dye, respectively, were chosen as model compounds (Scheme 1).

Scheme 1. Structures of fluorescein- and coumarin-labeled hybrids 1F and 1C, respectively, bearing four enzymatically cleavable ester groups.

Hybrid 1F

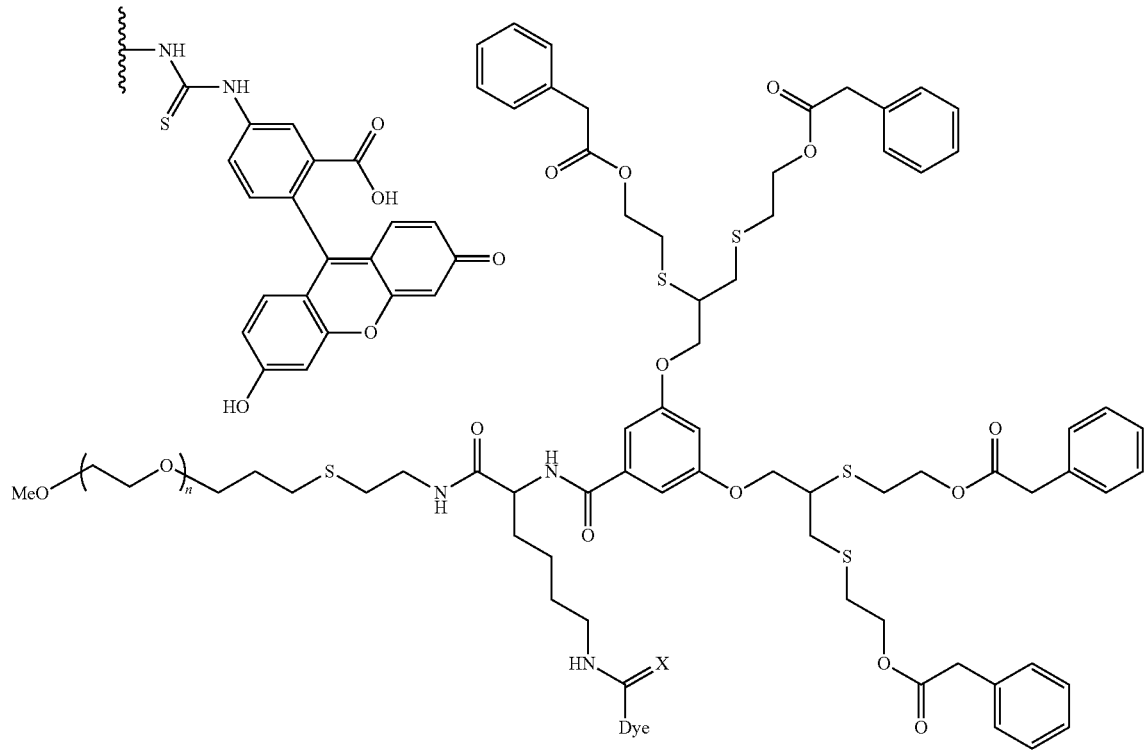

Dye = 5-thiourea-fluorescein

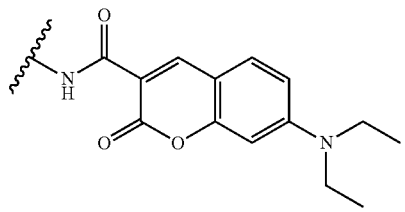

Hybrid 1C

Dye = 7-Diethylamino-3-carboxamide-coumarin

Figure 8A:
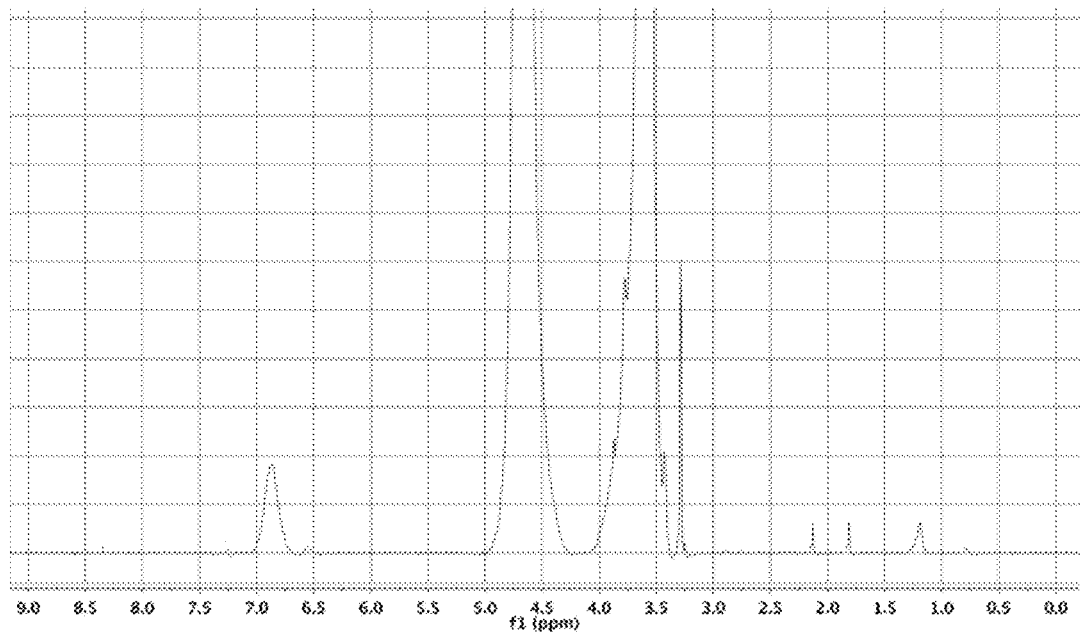
FIG. 8A: $^1$H-NMR spectrum of hybrid 1F in D$_2$O before addition of PLE.
Figure 8B:
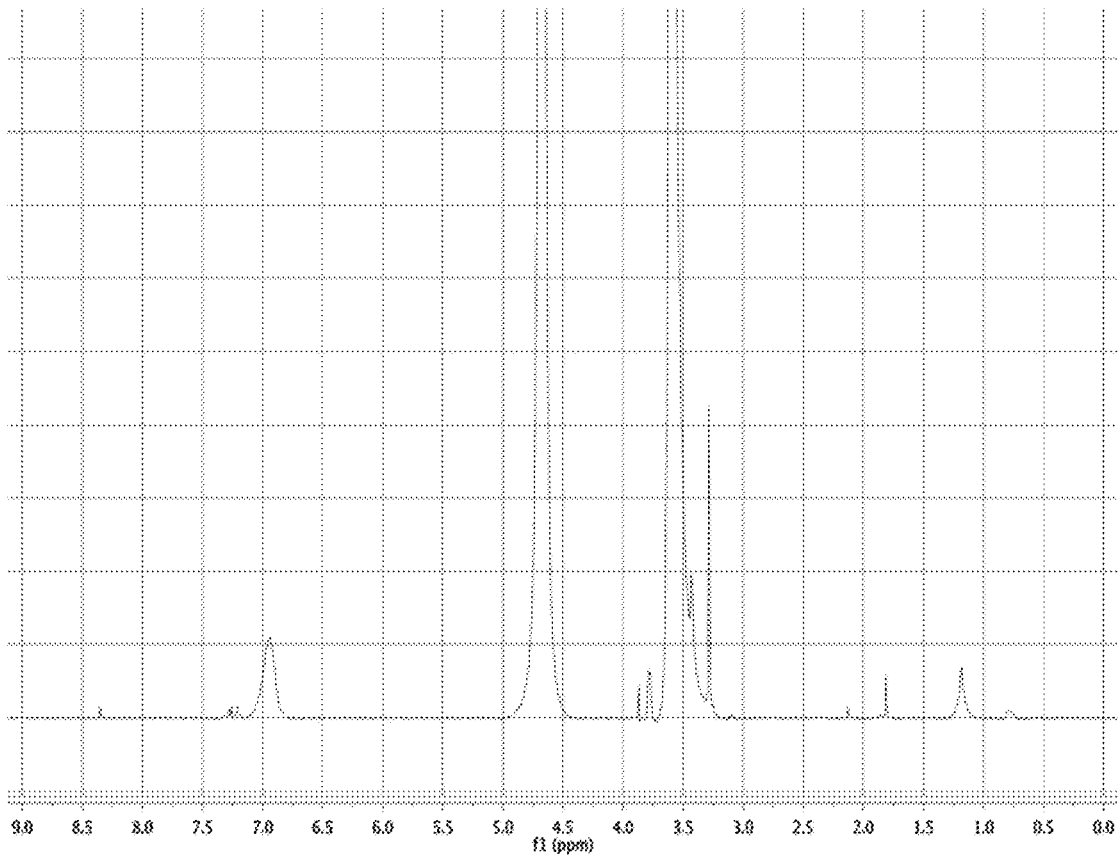
FIG. 8B: $^1$H-NMR spectrum of hybrid 1C in D$_2$O before addition of PLE.

Characterization of the self-assembled micelles: Dynamic light scattering (DLS) measurements showed diameters of about 17 nm for both hybrids 1F and 1C (FIG. 2a). Transmission electron microscopy (TEM) images confirmed the formation of spherical structures (FIGS. 2b and 2c). The critical micellar concentrations, determined using Nile red, were 6 µM and 3 µM for hybrids 1F and 1C, respectively. Further support for the micellar core-shell morphology was obtained from comparison of $^1$H-NMR spectra in CDCl$_3$ and D$_2$O as peaks assigned to dendron were significantly broadened or disappeared in D$_2$O, whereas the PEG signals remained unchanged (FIG. 8A-8B).

Figure 3A:
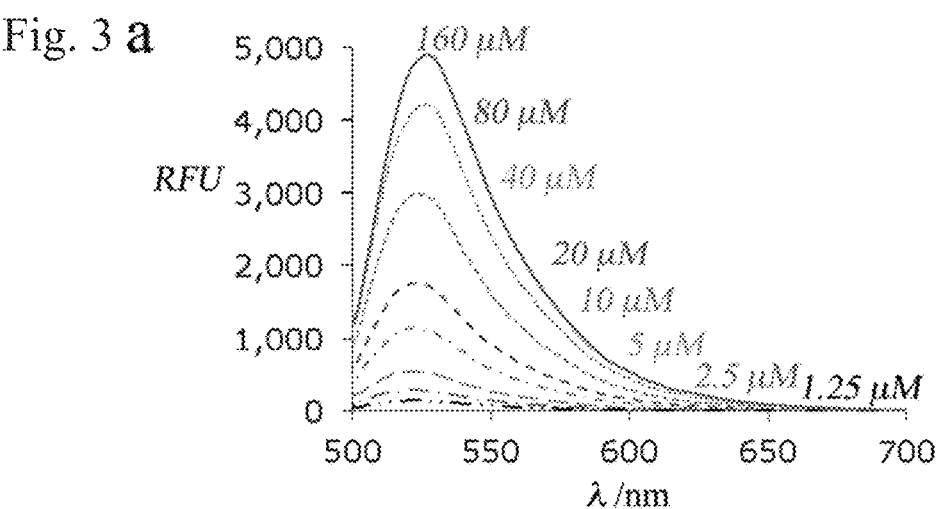
FIG. 3: (a) Fluorescence spectra of 1F (Ex 470 nm). (b) Comparison of the emission intensities (Ex 470 nm, Em 525 nm) of hybrids 1F and 7F (obtained by chemical hydrolysis) as a function of concentration. Photos of solutions of hybrids (160 μM) excited by a standard 365 nm UV-lamp.
Figure 3B:
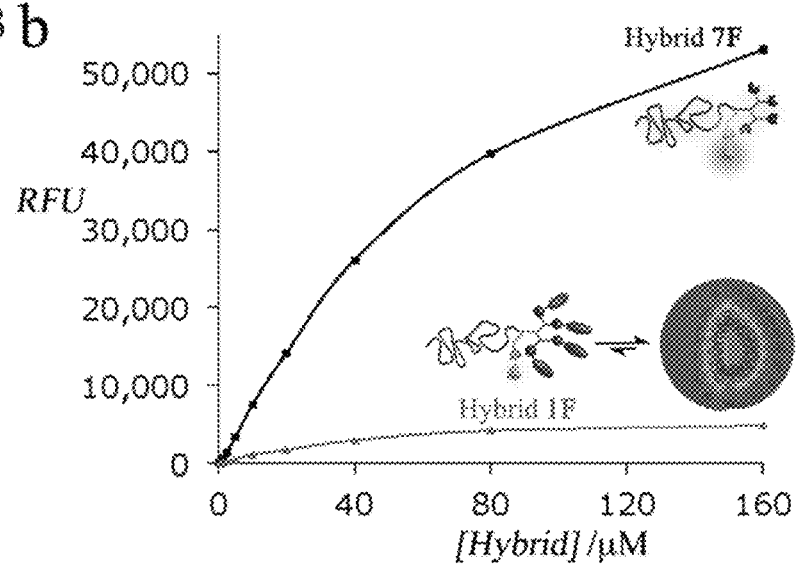

After the self-assembly of hybrids 1F and 1C into micelles was confirmed, their fluorescence was studied together with hydrophilic hybrids 7F and 7C as controls. As hypothesized, the emission intensities of hybrid 1F (FIG. 3a) were significantly weaker than those of hydrophilic hybrid 7F (FIG. 3b) due to self-quenching in the assembled state.

Figure 4A:
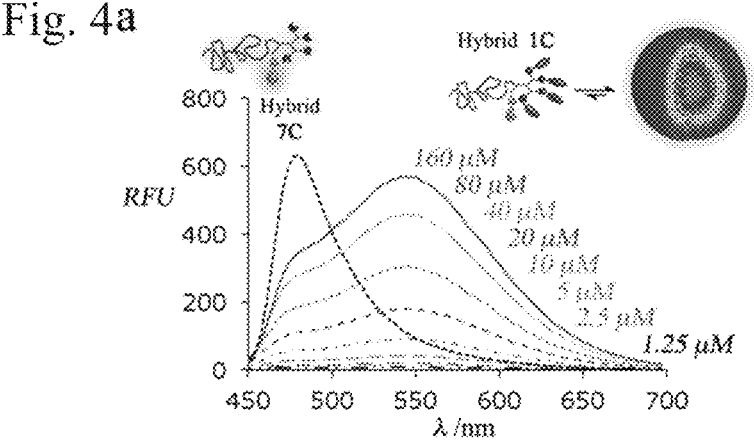
FIG. 4: (a) Fluorescence spectra of 1C (Ex 420 nm) and photos of solutions of hybrids (160 μM) excited by a standard 365 nm UV-lamp. (b) Fluorescence spectra of 1C (Ex 420 nm) at concentrations below its CMC value. (c) Excitation spectra of hybrid 1C recorded at $\lambda_{em}$ monomer=480 and $\lambda_{em}$ excimer=540 mm (d) Comparison of the ratio of emission intensities at 540 nm and 480 nm (Ex 420 nm) of hybrids 1C and 7C (obtained by chemical hydrolysis) as a function of their concentrations.
Figures 4B, 4C:
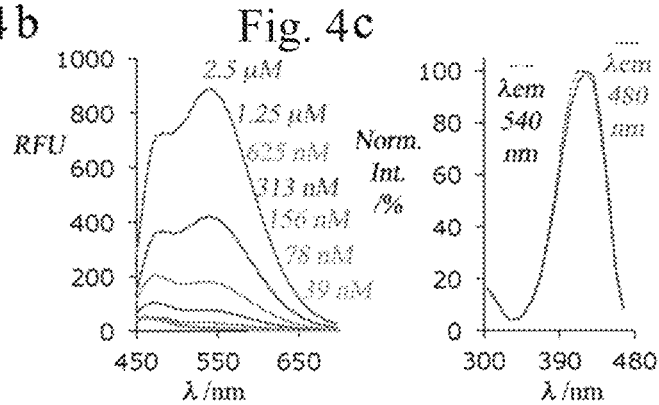
Figure 4D:
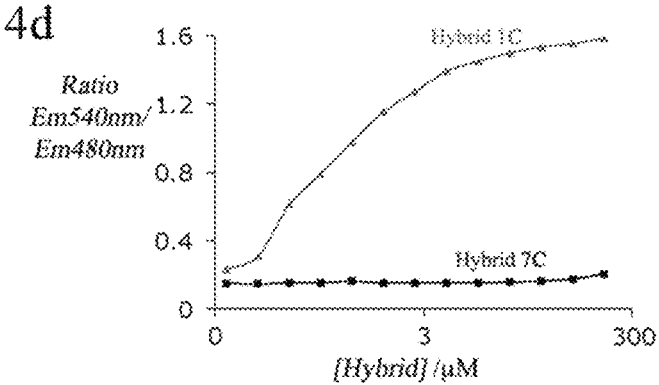

Comparison of the coumarin-labeled hybrids showed that hydrophilic hybrid 7C had an emission maximum at 480 nm, as expected for this coumarin derivative, whereas micelles based on hybrid 1C showed a significantly red-shifted maximum at 540 nm with a shoulder at 480 nm (FIGS. 4a and 4b). This 60 nm red-shift can be explained by formation of excimers by closely packed coumarin dyes at the interface between the PEG shell and the hydrophobic core, as confirmed by excitation measurements (FIG. 4c). Very interestingly, comparison of the ratio of emission intensities at 540 nm and 480 nm, which is indicative of the self-assembly process, reveals that the amphiphilic labeled hybrids start to self-assemble in concentrations well below their CMC value (FIG. 4d). The inherited ability of these new hybrids to report on their self-assembly, opens opportunities to deeper understanding of self-assembly as it allows a direct feedback from the polymers on their aggregation state.

Figure 5A:
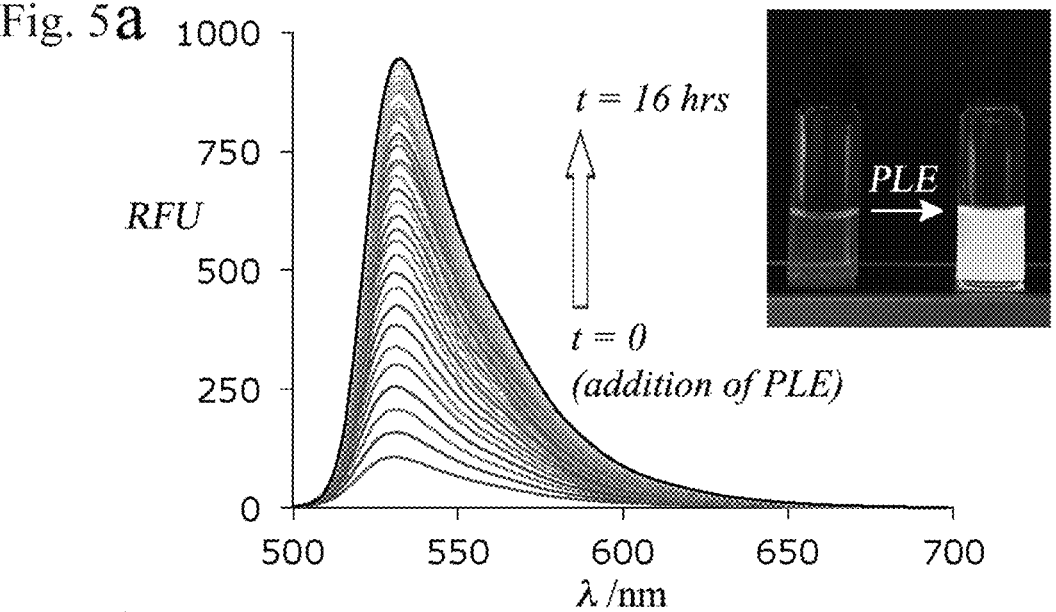
FIG. 5: (a) Time-dependent fluorescence spectra of hybrid 1F (160 μM) after the addition of PLE (27 nM) and photos of a solution of 1F before and after addition of PLE. (b) Overlay of the increase in fluorescence and HPLC analysis of enzymatic degradation of hybrid 1F.
Figure 5B:
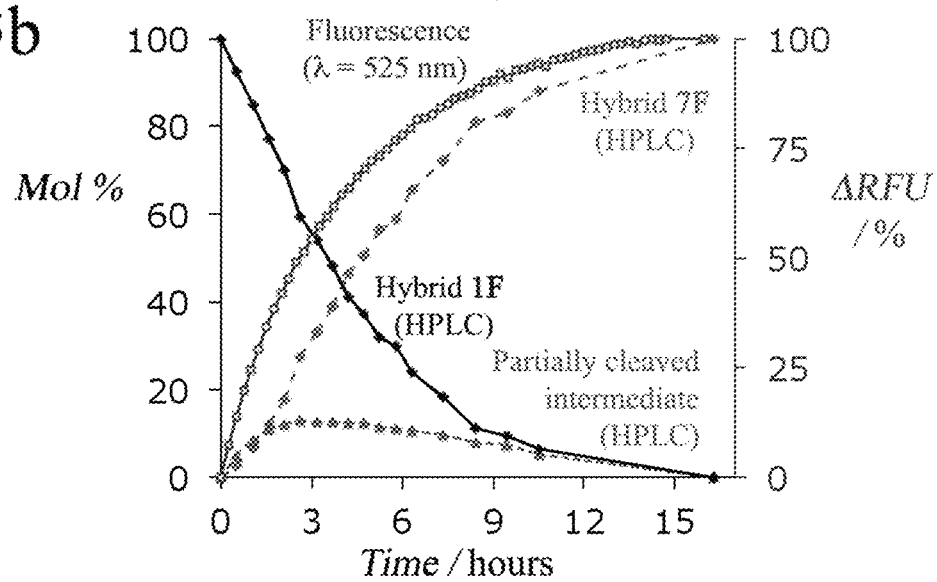
Figure 16:
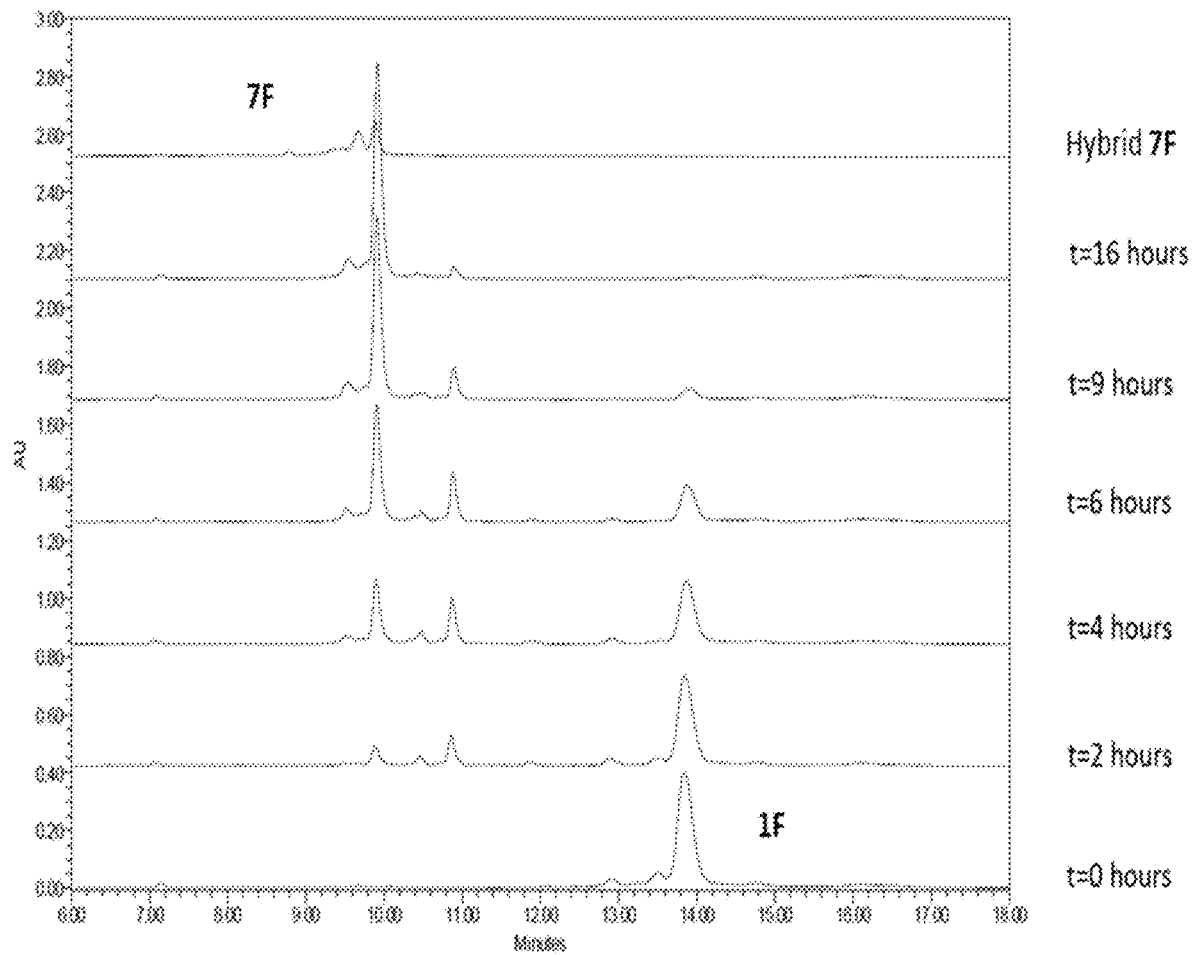
FIG. 16: HPLC monitoring of micelle degradation in presence of 27 nM PLE enzyme for hybrid 1F over time.
Figure 17:
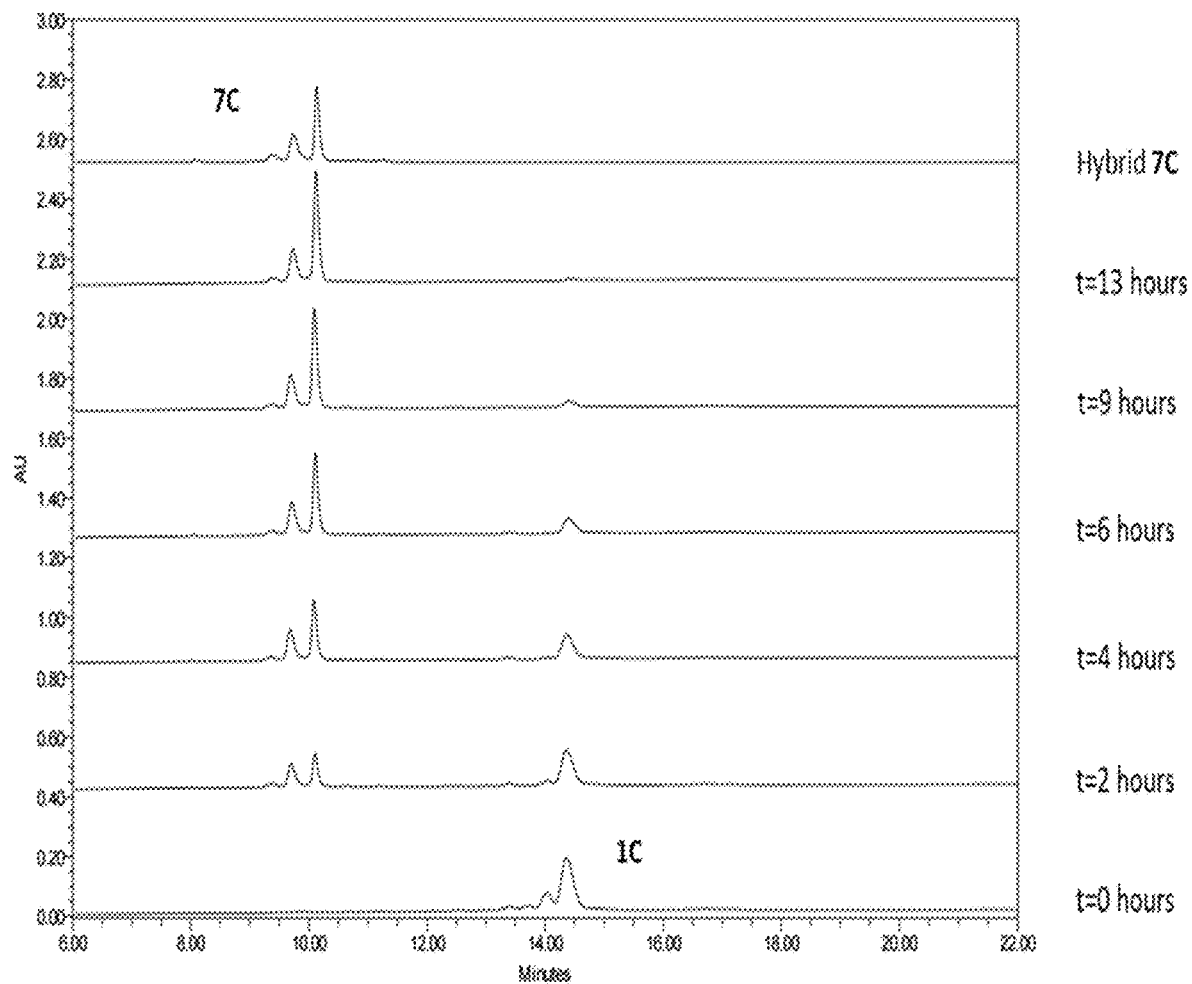
FIG. 17: HPLC monitoring of micelle degradation in presence of 270 nM PLE enzyme for hybrid 1C over time.

Characterization of the enzymatically triggered disassembly: The significant differences between the fluorescence of the assembled and disassembled states motivated us to explore whether the enzymatically triggered structural change from micelles into hydrophilic hybrids could induce the spectral responses. Parallel HPLC analysis and fluorescence measurements of both hybrids in the presence and absence of the activating enzyme (porcine liver esterase, PLE) were used to study the enzymatic activation. The HPLC data indicated transformations of hybrids 1F and 1C into the corresponding hydrophilic tetra-hydroxy hybrids 7F and 7C, respectively, upon addition of PLE (FIGS. 16 and 17). The very weak fluorescence of the fluorescein-labeled hybrid 1F at 525 nm (excited at 470 nm) increased rapidly upon addition of the enzyme (FIG. 5a). The excellent correlation with the HPLC data (FIG. 5b) indicates that, as hypothesized, the enzymatic hydrolysis of the micelle-forming amphiphilic hybrids leads to the formation of hydrophilic hybrids that disassemble and diffuse away from each other. This physical separation halts the self-quenching of the dyes and thus turns on their strong intrinsic fluorescence.

Figure 6A:
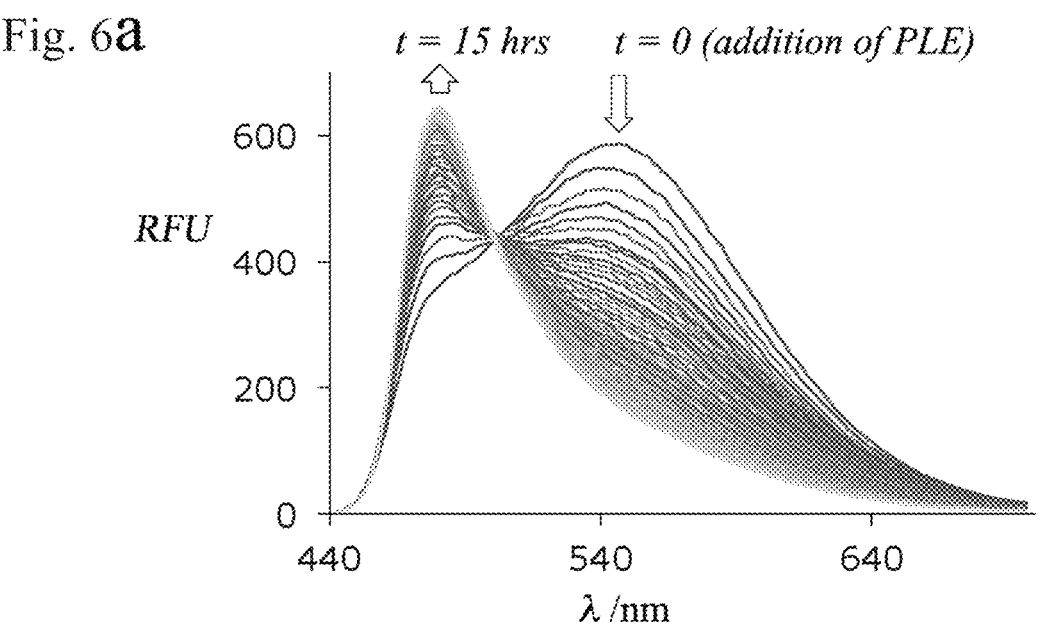
FIG. 6: (a) Time-dependent fluorescence spectra of hybrid 1C (160 μM) after the addition of PLE (270 nM). (b) Overlays of the changes in fluorescence and HPLC analysis of the enzymatic degradation of hybrid 1C.

A very promising spectral response was also observed for the micelles of hybrid 1C that showed a red-shifted spectrum relative to the hydrophilic-labeled hybrid 7C, with maximum emission at 540 nm due to the formation of excimers in the assembled state. Addition of the enzyme resulted in a decrease of emission at 540 nm and an increase in emission intensity at 480 nm (FIG. 6a). This change in fluorescence, which correlates very well with the HPLC analysis (FIG. 6b), resulted from enzymatic cleavage of the hydrophobic end-groups of hybrids 1C, which led to the formation of hydrophilic hybrids (7C) and disassembly of the micelles. As the spatial separation of the labeled hybrids increases, the coumarin dyes cannot form excimers and the emission at 540 nm decays whereas the expected intrinsic emission at 480 nm increases.

Figure 6B:
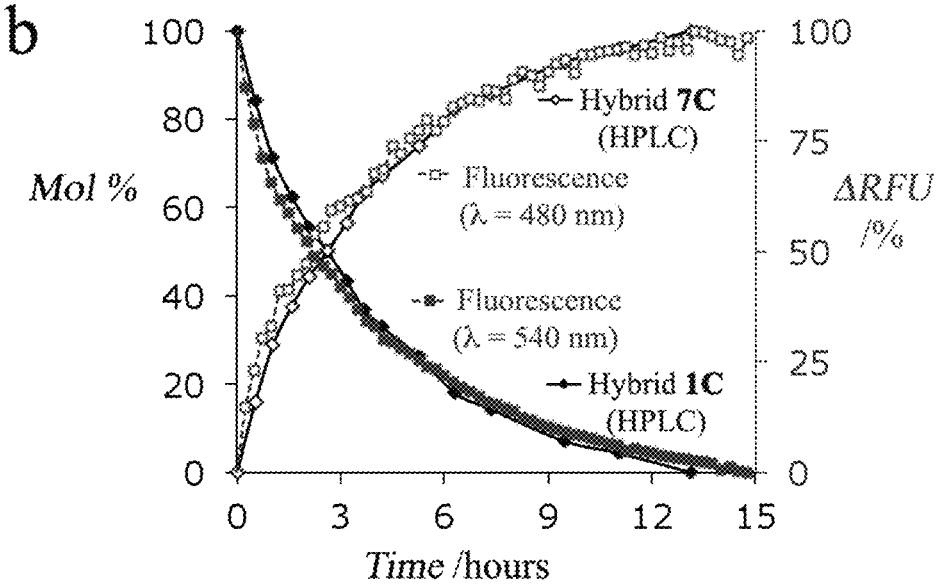
Figure 7A:
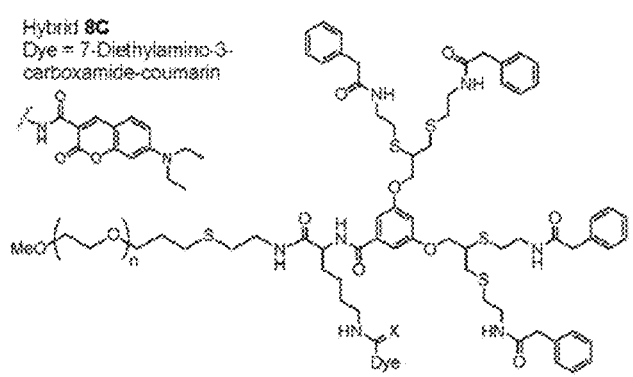
FIG. 7: (a) Structure of amidase-responsive hybrid 8C bearing four cleavable amide bonds and labeled with a coumarin derived dye. (b) Time-dependent fluorescence spectra of hybrid 8C (160 μM) after the addition of PGA (1 μM). (c) Overlays of the changes in fluorescence and HPLC analysis of the enzymatic degradation of hybrid 1C.
Figure 7B:
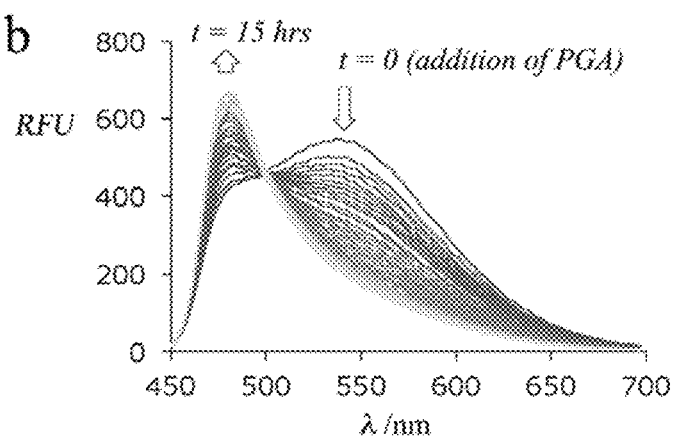
Figure 7C:
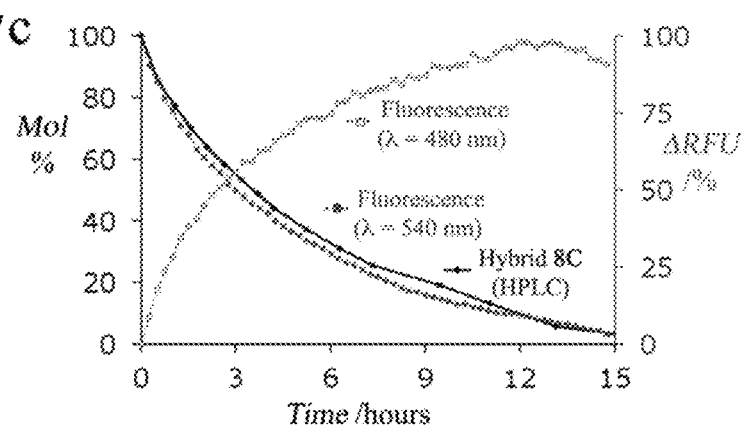

In order to demonstrate the high modularity of this molecular design and the ability to tune its enzymatic activity, an amidase-responsive hybrid MeO-PEG-Lys(C)-dendron-(NHCOCH$_2$Ph)$_4$, 8C was synthesized, with hydrophobic phenyl acetamide end-groups (FIG. 7a) that can be cleaved by the enzyme penicillin G amidase (PGA).[2] Whereas the ester-based hybrids 1F and 1C showed complete transformation into fully hydrolyzed hybrids, the amidase-responsive hybrids showed accumulation of partially cleaved intermediates. With fluorescently labeled hybrids, this partial cleavage could lead to the formation of small aggregates such as dimers or trimers, which might result in significant dye-dye interactions also in the non-micellar state, thus limiting the magnitude of the desired spectral effect. HPLC analysis of the enzymatic degradation of 8C by PGA (FIG. 18) showed indeed the formation of partially cleaved intermediates, however, the fluorescence response (FIG. 7b) was as strong as the one observed for the esterase-responsive hybrids (FIG. 6b). Furthermore, a very good correlation was observed for the disappearance of the starting hybrid 8C and the spectral changes at both 540 nm and 480 nm (FIG. 7c).

In summary, the novel molecular design described herein enabled the synthesis of fluorescently labeled smart polymeric amphiphiles and their self-assembly into enzyme-responsive micelles with significantly altered fluorescent properties in the assembled compared to unassembled states due to dye-dye interactions in the micelles. Enzymatic cleavage of the hydrophobic end-groups of the dendrons increased the hydrophilicity of the hybrids, resulting in disassembly of the micelles. This supramolecular structural change was translated into a spectral response as the dyes diffuse away from each other and dye-dye interactions are diminished and the intrinsic fluorescence of the dyes is regained. Taking advantage of the high modularity of the supramolecular translation mechanism, micelles were designed with Turn-On or spectral switching of the emitted fluorescence, depending on the type of the labeling dye. The highly efficient synthesis and the ability to rationally adjust both the activating enzyme and spectral-response by installing suitable enzymatic substrates and labeling dye, respectively, make this platform highly promising for the fabrication of advanced enzymatically activated fluorescent imaging probes and smart drug delivery platforms. Furthermore, harnessing the structural responsiveness of this polymeric platform opens the way for simple transformation of non-responsive dyes into enzymatically activated smart fluorescent probes.

Example 2—Synthesis Protocol of the Amphiphilic PEG-Dendron Hybrids Containing Fluorescent Probes The two hybrids, 1F and 1C, were synthesized from MeO-PEG-Lys(Boc)-Fmoc (2) as illustrated in Scheme 2. Following selective deprotection of the Fmoc group, the amine was conjugated to di-acetylene 3 to give hybrid 4. The acetylene groups were then reacted with 2-mercaptoethanol through a thiol-yne reaction to yield hybrid 5. Esterification with phenyl acetic acid yielded hybrid 6 with four enzymatically cleavable end-groups. The Boc group was removed by trifluoroacetic acid, followed by conjugation of dye to the deprotected amine to yield amphiphilic hybrids 1F and 1C. The expected hydrolysis products, hydrophilic hybrids 7F and 7C, were also synthesized as reference compounds. All polymeric hybrids were characterized by $^1$H-NMR, $^{13}$C-NMR, IR, and GPC (1F, 1C, 7F, and 7C were also characterized by MALDI-MS) and the experimental data was found to be in good agreement with the theoretical one.

Scheme 2. Synthesis of amphiphilic hybrids 1F and 1C and their hydrolysis products 7F and 7C, respectively.

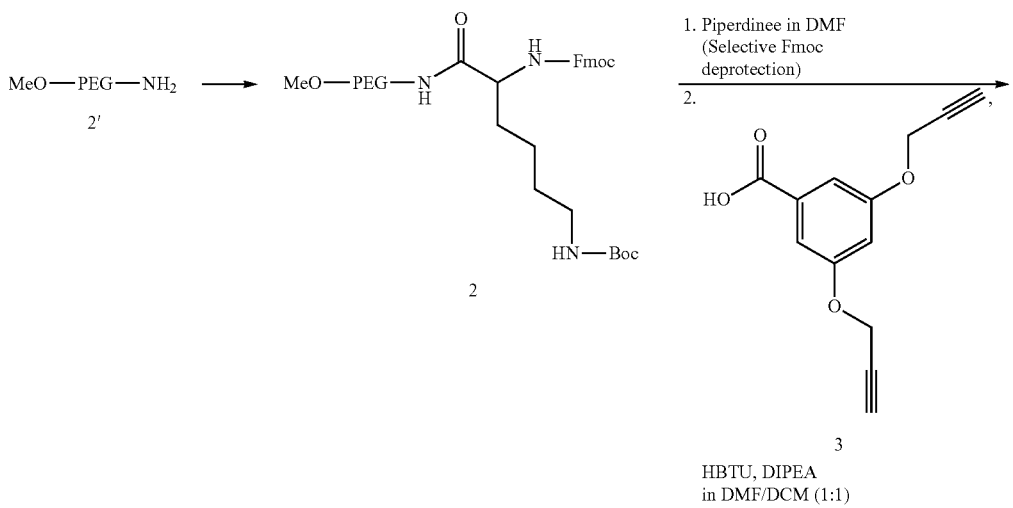

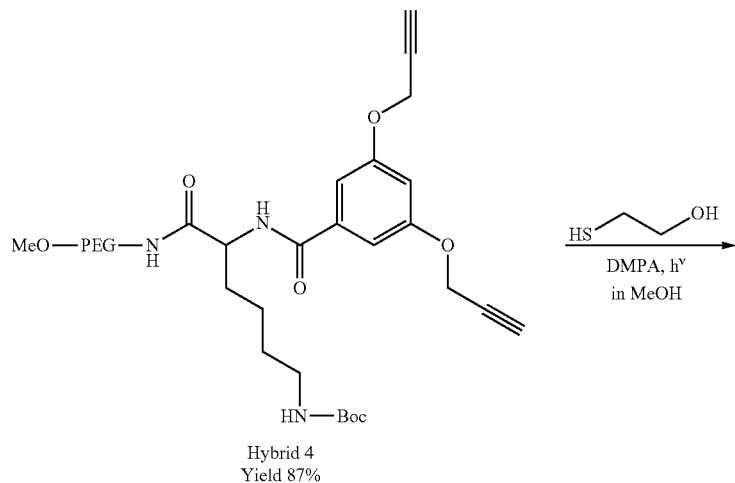

Hybrid 4
Yield 87%

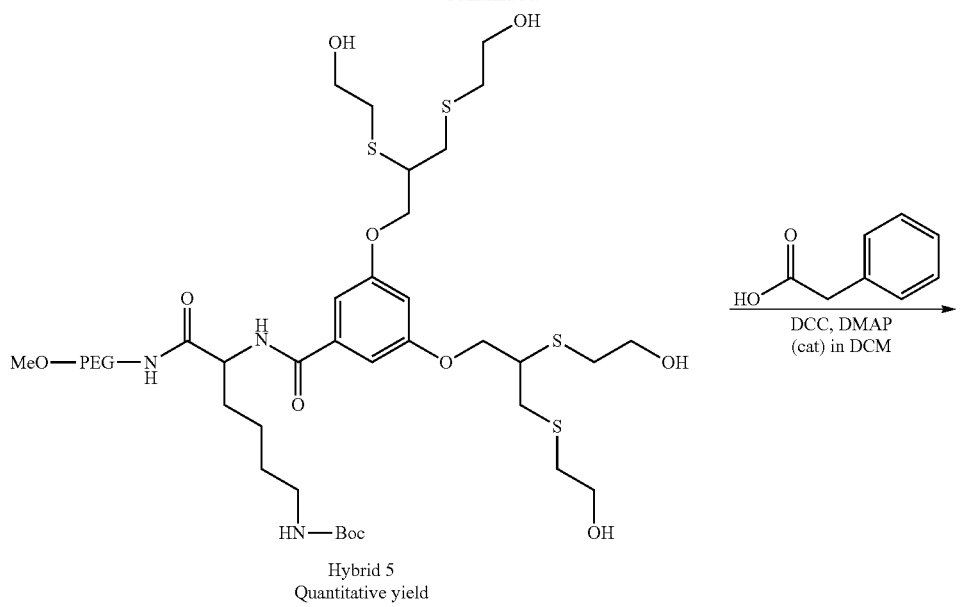
Hybrid 5
Quantitative yield
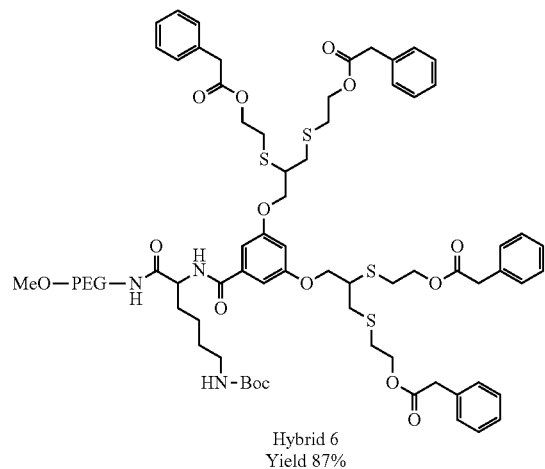
Hybrid 6
Yield 87%
1. TFA/DCM (1:1) (Boc deprotection)
2. FITC, DIPEA, in DCM
1. TFA/DCM (1:1) (Boc deprotection)
2. 7-diethylamino-4-carboxycoumarine, HBTU, DIPEA in DMF/DCM (1:1)

-continued

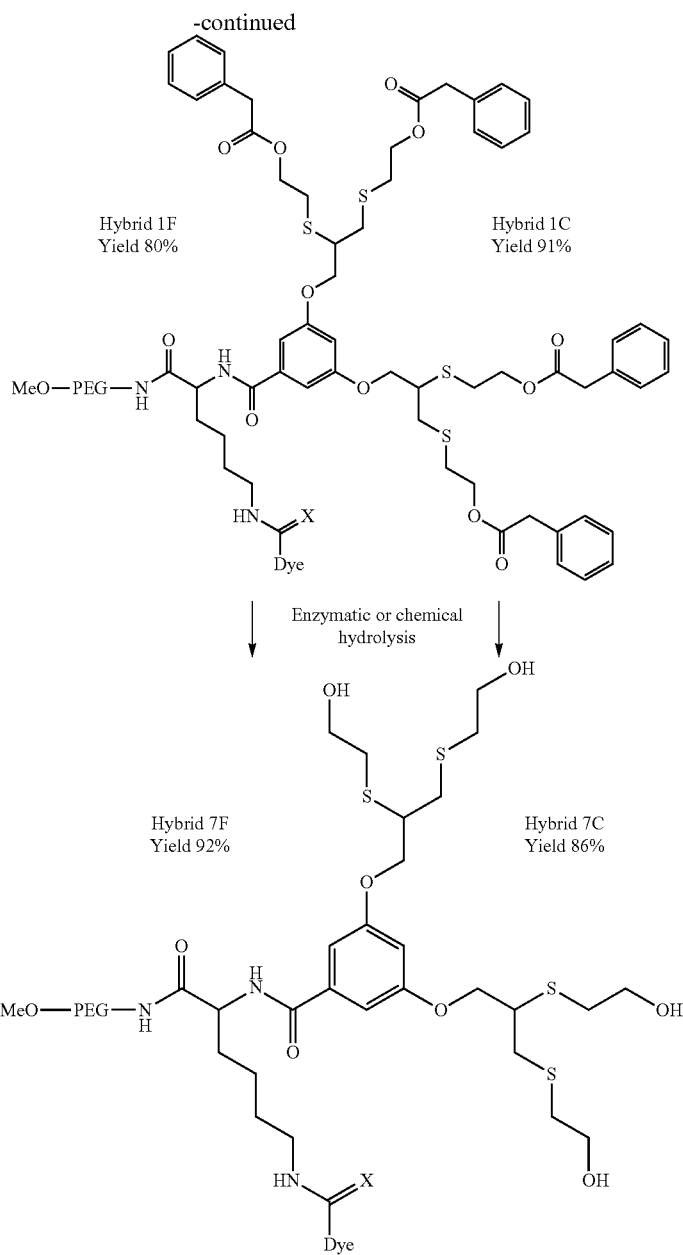

Hybrid 1F Yield 80%
Hybrid 1C Yield 91%

Enzymatic or chemical hydrolysis

Hybrid 7F Yield 92%
Hybrid 7C Yield 86%

General Procedure for Preparing Precursor 2':

Scheme 3A

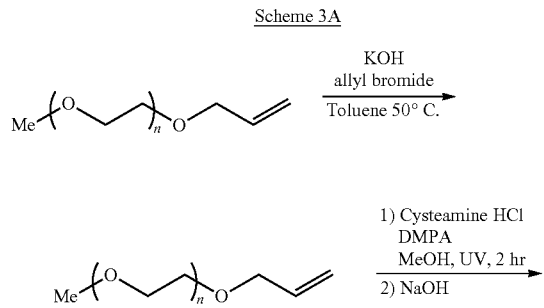

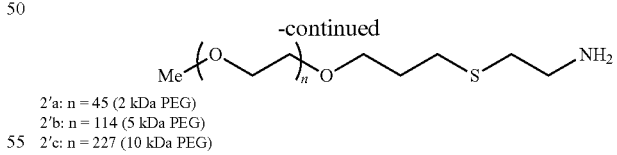

2'a: n = 45 (2 kDa PEG)
2'b: n = 114 (5 kDa PEG)
2'c: n = 227 (10 kDa PEG)

MeO-PEG-Allyl precursors may be prepared by the process described in general Scheme 3A hereinabove. Poly(ethylene glycol) methyl ether was dissolved in toluene (10 mL per 1 g) with KOH (10 eq.). The solution was refluxed for at least 1 hour using a Dean Stark water separation system. Solution was cooled down to 50° C. and then allyl bromide (10 eq.) was added slowly and the reaction was stirred overnight. The solution was filtered hot through celite, the celite was then washed with DCM. Solvents were evaporated in vacuum and the residue was re-dissolved in DCM (5 mL per 1 g PEG). MeO-PEG-Allyl product was precipitated by the dropwise addition of 1:1 v/v Ether: Hexane mixture (50 mL per 1 g PEG). Precipitate was filtered and washed with ether and then with hexane. The final white solid product was dried under high vacuum. Three different products were prepared using 3 PEG precursors (2 kDa PEG (2a), 5 kDa PEG (2b) and 10 kDa PEG (2c).

MeO-PEG2 kDa-Allyl: 3.00 g (1.5 mmol) Poly (ethylene glycol) methyl ether ($M_n$=2 kDa) were reacted according to the general procedure (I) and the product was obtained as a white solid (2.42 g) 80% yield. $^1$H-NMR (CDCl$_3$): δ 5.85-5.95 (m, 1H, vinyl —CH=CH$_2$), 5.26 (dd, J=1.4 Hz, 17.2 Hz, 1H, trans vinyl —CH=CH$_2$), 5.17 (dd, J=1.0 Hz, 10.4 Hz, 1H, cis vinyl —CH=CH2), 4.01 (d, J=5.7 Hz, 2H, —O—CH$_2$—CH=CH$_2$), 3.44-3.82 (m, 206H, PEG backbone), 3.37 (s, 3H, H$_3$C—O—); $^{13}$C-NMR (CDCl$_3$) δ 134.9, 117.2, 72.4, 72.1, 70.7, 69.6, 59.1; FT-IR, ν(cm$^{-1}$) 2878, 1466, 1456, 1359, 1341, 1279, 1240, 1145, 1098, 1060, 957, 947, 842; GPC (DMF+LiBr) $M_n$=1.8 kDa, PDI=1.04. MALDI-TOF MS: molecular ion centered at 2.0 kDa.

MeO-PEG5 kDa-Allyl: 5.00 g (1 mmol) Poly (ethylene glycol) methyl ether ($M_n$=5 kDa) were reacted according to the general procedure (I) and the product was obtained as a white solid (4.45 g), 88% yield. $^1$H-NMR (CDCl$_3$): δ 5.86-5.95 (m, 1H, —CH=CH$_2$), 5.26 (d, J=17.3 Hz, 1H, trans vinyl —CH=CH$_2$), 5.17 (d, J=10.3 Hz, 1H, cis vinyl —CH=CH$_2$), 4.01 (d, J=5.3 Hz, 2H, —O—CH$_2$—CH=CH$_2$), 3.44-3.82 (m, 553H, PEG backbone), 3.37 (s, 3H, H$_3$C—O—); $^{13}$C-NMR (CDCl$_3$) δ 134.9, 117.2, 72.3, 72.0, 70.7, 69.5, 59.1; FT-IR, ν(cm$^{-1}$) 2881, 1466, 1360, 1341, 1279, 1240, 1147, 1098, 1060, 959, 842; GPC (DMF+LiBr): $M_n$=5.7 kDa, PDI=1.02.

MeO-PEG10 kDa-Allyl: 2.00 g (0.2 mmol) Poly (ethylene glycol) methyl ether ($M_n$=10 kDa) were reacted according to the general procedure (I) and the product was obtained as a white solid (1.98 g). $^1$H-NMR (CDCl$_3$): δ 5.82-5.95 (m, 1H, —CH=CH$_2$), 5.25 (dd, J=1.4 Hz, 17.2 Hz, 1H, trans vinyl —CH=CH$_2$), 5.15 (dd, J=1.1 Hz, 10.3 Hz, 1H, cis vinyl —CH=CH$_2$), 4.00 (d, J=5.6 Hz, 2H, —O—CH$_2$—CH=CH$_2$), 3.43-3.81 (m, 956H, PEG backbone), 3.35 (s, 3H, H$_3$C—O—); $^{13}$C-NMR (CDCl$_3$) δ 134.9, 117.2, 72.3, 72.0, 71.1, 70.7, 69.5, 59.1; FT-IR, ν(cm$^{-1}$): 2881, 1467, 1454, 1360, 1341, 1279, 1240, 1147, 1098, 1060, 960, 948, 842; GPC (DMF+LiBr): $M_n$=11.2 kDa, PDI=1.02.

General Procedure for Compounds 2'a-c

MeO-PEG-Allyl was dissolved in MeOH (5 mL per 1 g). Cystamine hydrochloride (40 eq.) and DMPA (0.2 eq.) were added. The solution was purged with nitrogen for minutes and then placed under UV light at 365 nm for 2 hours. MeOH was evaporated to dryness and the crude mixture was dissolved in NaOH 1N (100 mL per 1 g). This aqueous phase was extracted with DCM (3×50 mL). The organic phase was filtered through celite and evaporated in vacuum. The residue was re-dissolved in DCM (5 mL per 1 g PEG) and product was precipitated by the dropwise addition of 1:1 v/v Ether:Hexane mixture (50 mL per 1 g PEG). The white precipitate was filtered and washed with ether and then with hexane and was dried under high vacuum.

2'a: 2.00 g (0.97 mmol) MeO-PEG2k-Allyl were reacted according to the general procedure (II) and the product was obtained as a white solid (1.70 g, 82% yield) $^1$H-NMR (CDCl$_3$): δ 3.44-3.82 (m, 225H, PEG backbone), 3.37 (s, 3H, H$_3$C—O—), 2.86 (t, J=6.3 Hz, 2H, —CH$_2$—NH$_2$), 2.56-2.62 (m, 4H, —CH$_2$—S—CH$_2$—), 1.85 (qui, J=6.7 Hz, 2H, —O—CH$_2$—CH$_2$—CH$_2$—S—); $^{13}$C-NMR (CDCl$_3$) δ 72.1, 70.7, 70.4, 69.8, 59.2, 41.3, 36.4, 30.0, 28.6; FT-IR ν(cm$^{-1}$): 2883, 1467, 1456, 1360, 1343, 1280, 1241, 1146, 1115, 1061, 963, 947, 842; GPC (DMF+LiBr): $M_n$=1.8 kDa, PDI=1.04.

2'b: 2.12 g (0.42 mmol) MeO-PEG5k-Allyl were reacted according to the general procedure (II) and the product was obtained as a white solid (2.02 g, 94% yield). $^1$H-NMR (CDCl$_3$): δ 3.45-3.83 (m, 590H, PEG backbone), 3.38 (s, 3H, H$_3$C—O—), 2.87 (t, J=6.2 Hz, 2H, —CH$_2$—NH$_2$), 2.57-2.63 (m, 4H, —CH$_2$—S—CH$_2$—), 1.82-1.89 (m, 2H, —O—CH$_2$—CH$_2$—CH$_2$—S—); $^{13}$C-NMR (CDCl$_3$): δ 72.1, 70.7, 70.3, 69.4, 59.2, 40.6, 36.4, 29.8, 28.5; FT-IR ν(cm$^{-1}$): 2882, 1542, 1466, 1360, 1341, 1279, 1240, 1146, 1102, 1060, 959, 842; GPC (DMF+LiBr): $M_n$=5.6 kDa, PDI=1.04.

2'c: 500 mg (0.05 mmol) MeO-PEG10k-Allyl were reacted according to the general procedure (II) and the product was obtained as a white solid (434 mg) 86% yield. $^1$H-NMR (CDCl$_3$): δ 3.43-3.81 (m, 1152H, PEG backbone), 3.36 (s, 3H, H$_3$C—O—), 2.87 (t, J6.4=Hz, 2H, —CH$_2$—NH$_2$), 2.53-2.66 (m, 4H, —CH$_2$—S—CH$_2$—), 1.84 (qui, J=6.7 Hz, 2H, —O—CH$_2$—CH$_2$—CH$_2$—S—); $^{13}$C-NMR (CDCl$_3$) δ 72.0, 71.2, 70.7, 69.7, 59.1, 41.1, 35.9, 29.9, 28.5; FT-IR ν(cm$^{-1}$): 2880, 1467, 1454, 1359, 1341, 1279, 1240, 1146, 1096, 1060, 960, 947, 841; GPC (DMF+LiBr): $M_n$=11.3 kDa, PDI=1.02.

Scheme 3B. Preparation of hybrids 2 and 4.

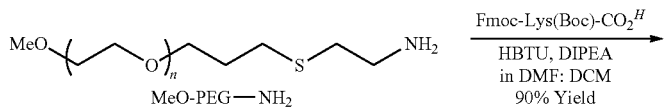

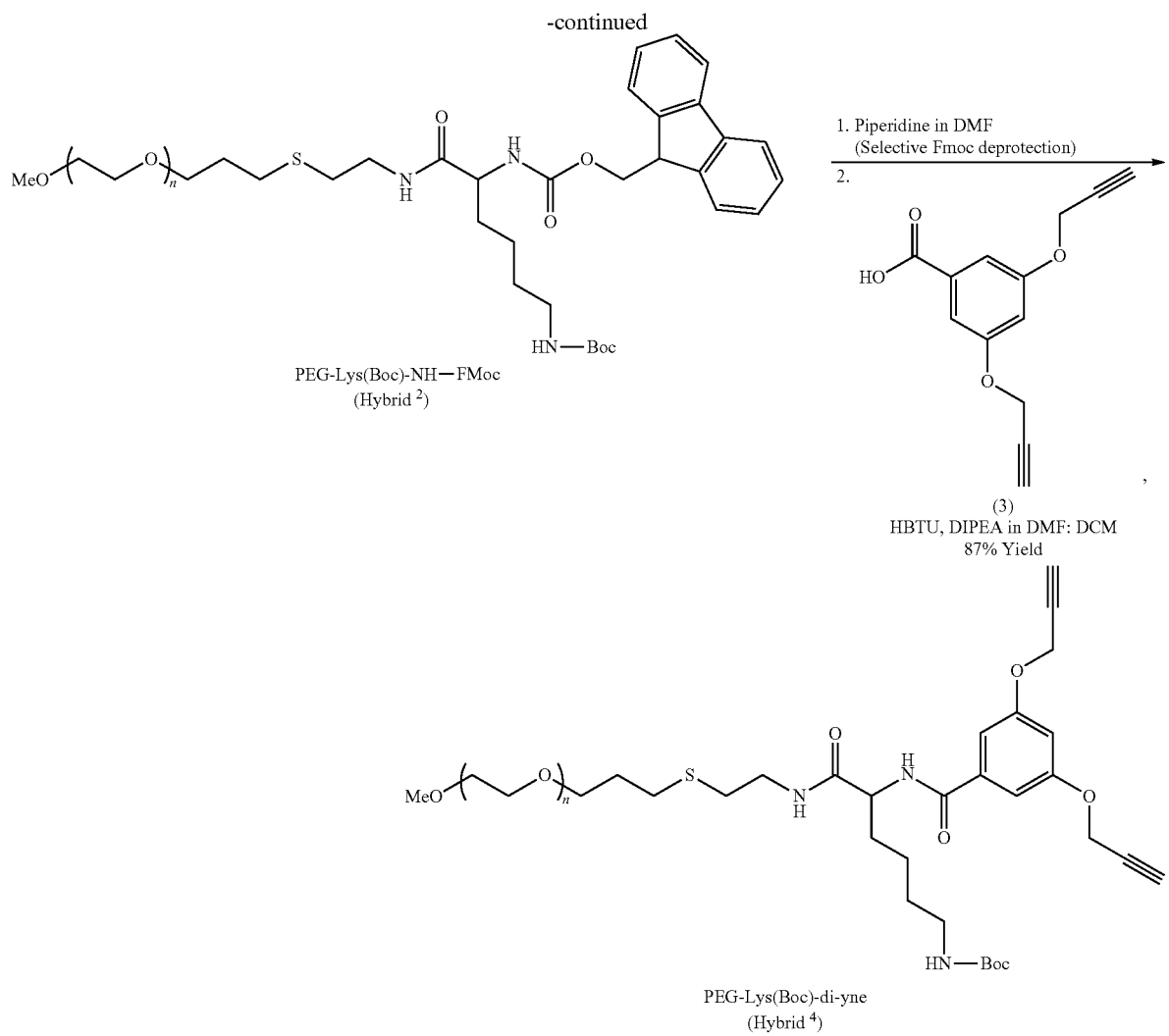

Hybrid 2 (MeO-PEG$_{5kDa}$-Lys(Boc)-Fmoc):

Fmoc-Lys(Boc)-CO$_2$H (5 eq.) and HBTU (5 eq.) were dissolved in DCM:DMF 1:1 (1 mL) followed by addition of DIPEA (15 eq.) and allowed to stir for 1 hour. The solution was added to 200 mg (0.04 mmol) of MeO-PEG$_{5kDa}$-NH$_2$[1] dissolved in DCM (1 mL). The reaction was stirred for 3 hours and complete coupling was confirmed by a negative Kaiser test. The crude mixture was loaded on a MeOH based LH20 SEC column. The fractions that contained the product were unified, the MeOH was evaporated in vacuum, further purification was done by re-dissolving the oily residue in DCM (1 mL) followed precipitation by the dropwise addition of Ether (50 mL). The white precipitate was filtered, washed twice with Ether and dried under high vacuum. The product was obtained as a white solid (197 mg, 90% yield).

$^1$H-NMR (CDCl$_3$): δ 7.69 (d, J=7.5 Hz, 2H, Ar—H), 7.53 (d, J=7.2 Hz, 2H, Ar—H), 7.33 (t, J=7.4 Hz, 2H, Ar—H), 7.24 (d, J=7.4 Hz, 2H, Ar—H), 6.60 (m, 1H, —CH$_2$—NH—CO—CH—), 5.59 (m, 1H, —NH-Fmoc), 4.71 (m, 1H, —NH-Boc), 4.35 (d, J=6.2 Hz, 2H, Fmoc-CH$_2$—), 4.14 (t, J=6.6 Hz, 1H, Fmoc-CH—CH$_2$—), 4.05 (m, 1H, —CO—CH—NH—), 3.57-3.31 (m, PEG backbone), 3.31 (s, 3H, CH$_3$—O-PEG), 3.10-2.86 (m, 2H, Boc-NH—CH$_2$—), 2.64-2.49 (m, 4H, —CH$_2$—S—CH$_2$—), 1.88-1.49 (m, 4H, —O—CH$_2$—CH$_2$—CH$_2$—S—+Boc-NH—CH$_2$—CH$_2$—CH$_2$—CH$_2$—CH—), 1.36 (m, 13H, Boc-NH—CH$_2$—CH$_2$—CH$_2$—CH—+Boc); $^{13}$C-NMR (CDCl$_3$): δ 171.8, 156.3, 156.2, 143.9, 141.4, 127.8, 127.2, 125.1, 120.0, 79.1, 72.0, 70.6, 69.5, 66.9, 63.8, 59.1, 55.0, 47.3, 40.0, 38.6, 32.2, 31.6, 29.8, 29.7, 28.6, 28.3, 22.6; FT-IR, ν (cm$^{-1}$): 2883, 1467, 1453, 1359, 1341, 1279, 1240, 1147, 1099, 1060, 959, 948, 842; GPC: Mn=5.3 kDa, PDI=1.05. Expected Mn=5.6 kDa.

Hybrid 4 (MeO-PEG$_{5kDa}$-Lys(Boc)-di-vne):

180 mg (0.03 mmol) of MeO-PEG$_{5kDa}$-Lys(Boc)-Fmoc (2) were dissolved in 20% piperidine v/v in DMF (3 mL) and stirred for 1 hour. The deprotected product was precipitated by the dropwise addition of 1:1v/v Ether:Hexane mixture (50 mL). The white precipitate was filtered and washed with Hexane and Ether and dried under high vacuum. The deprotected product was obtained as a white solid. Compound 3[1] (5 eq.) and HBTU (5 eq.) were dissolved in DCM:DMF 1:1 (1 mL) followed by addition of DIPEA (15 eq.) and allowed to stir for 1 hour. The solution was added to 173 mg (0.03 mmol) of the deprotected hybrid 2 MeO-PEG$_{5kDa}$-lys (BOC)—NH$_2$ dissolved in DCM (1 mL). The reaction was stirred for 1 hour, complete coupling was confirmed by a negative Kaiser test. The crude mixture was loaded on a MeOH based LH20 SEC column. The fractions that contained the product were unified and the MeOH was evaporated in vacuum, further purification was done by re-dissolving the oily residue in DCM (1 mL) followed by precipitation by the dropwise addition of Ether (50 mL). The white precipitate was filtered and washed twice with Ether and dried under high vacuum. The product was obtained as a white solid (162 mg, 87% yield).

$^1$H-NMR (CDCl$_3$): δ 7.08 (m, 1H, —CH—NH—CO—Ar—), 7.00 (m, 2H, Ar—H), 6.90 (d, J=6.1 Hz, 1H, —CH$_2$—NH—CO—CH—), 6.66 (d, J=2.4 Hz, 1H, Ar—H), 4.78 (m, 1H, —NH—Boc), 4.64 (d, J=2.3 Hz, 4H, —O—CH$_2$—C≡CH), 4.48 (q, J=7.1 Hz, 1H, —CO—CH—NH—), 3.82-3.33 (m, PEG backbone), 3.30 (s, 3H, CH$_3$—O-PEG), 3.01 (d, J=6.9 Hz, 2H, Boc-NH—CH$_2$—), 2.54 (m, 6H, —CH$_2$—S—CH$_2$—+—O—CH$_2$—C≡CH), 1.94-1.59 (m, 4H, —O—CH$_2$—CH$_2$—CH$_2$—S—+Boc-NH—CH$_2$—CH$_2$—CH$_2$—CH$_2$—CH), 1.44-1.24 (m, 13H, Boc-NH—CH$_2$—CH$_2$—CH$_2$—CH$_2$—CH+Boc); $^{13}$C-NMR (CDCl$_3$) δ 171.7, 166.8, 158.8, 156.2, 136.2, 107.1, 105.8, 82.1, 78.1, 76.3, 72.0, 70.6, 69.5, 59.1, 56.2, 53.7, 40.1, 38.8, 32.2, 31.5, 29.8, 29.7, 28.5, 28.3, 22.9; FT-IR, v (cm$^{-1}$): 2882, 1593, 1467, 1453, 1380, 1359, 1341, 1279, 1240, 1147, 1098, 1060, 960, 948, 842; GPC: Mn=5.8 kDa, PDI=1.08. Expected Mn=5.6 kDa.

Scheme 4. Preparation of hybrids 5 and 6.

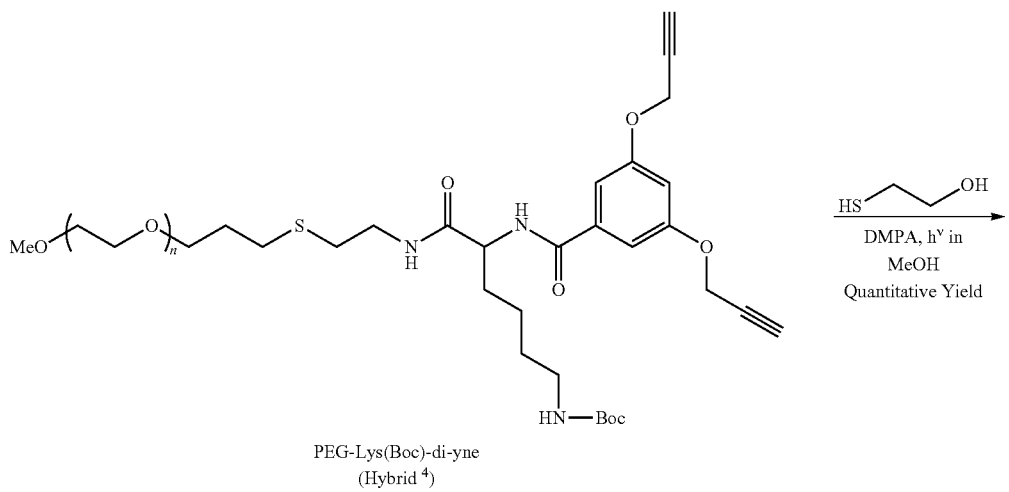

PEG-Lys(Boc)-di-yne
(Hybrid $^4$)

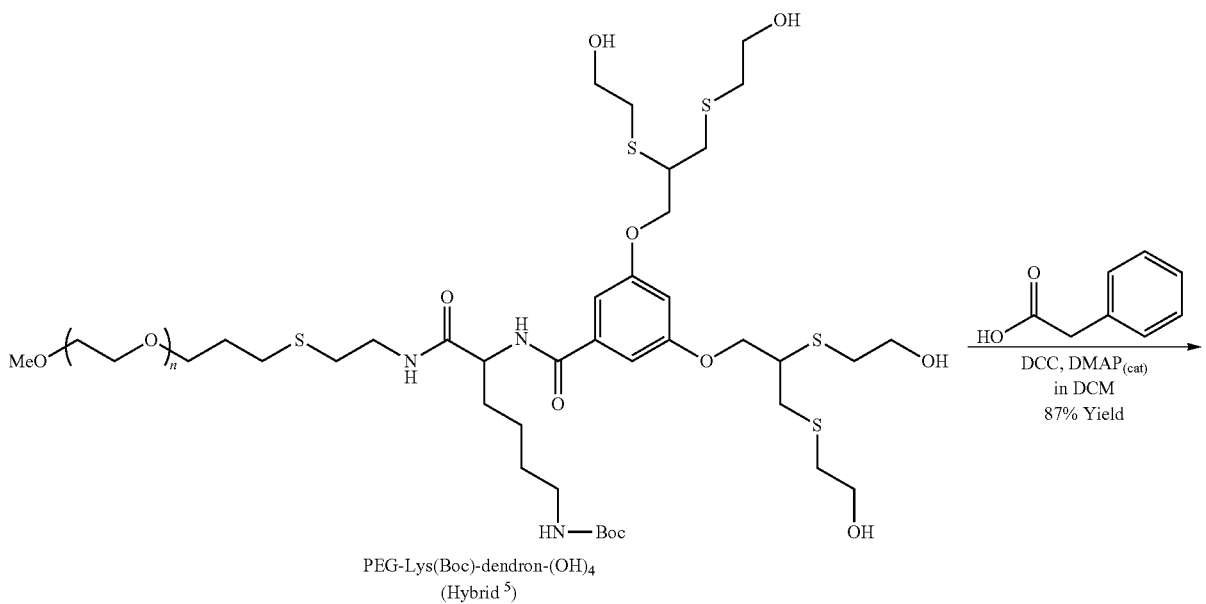

PEG-Lys(Boc)-dendron-(OH)$_4$
(Hybrid $^5$)

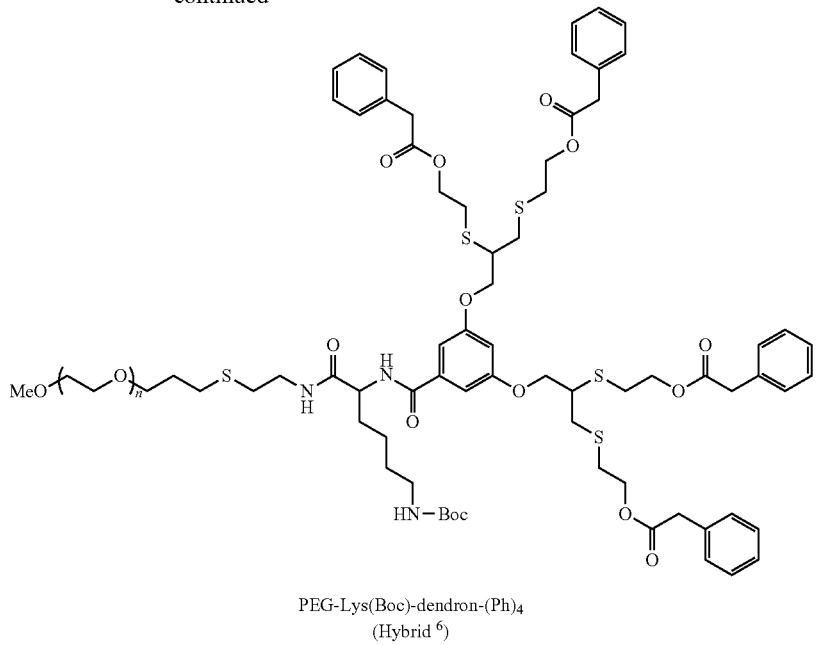

PEG-Lys(Boc)-dendron-(Ph)₄
(Hybrid 6)

Hybrid 5 (MeO-PEG$_{5kDa}$-Lys(Boc)-dendron-(OH)$_4$):

152 mg (0.03 mmol) of MeO-PEG$_{5kDa}$-Lys(Boc)-di-yne (4) were dissolved in MeOH (1 mL), 2-mercaptoethanol (80 eq.) and DMPA (0.8 eq.) were added. The solution was purged with nitrogen for 15 minutes and then placed under UV light at 365 nm for hours. The crude mixture was then loaded on a MeOH based LH20 SEC column. The fractions that contained the product were unified and the MeOH was evaporated in vacuum to yield an oily residue. In order to facilitate the removal of residual MeOH and solidification of the product, the oily residue was re-dissolved in DCM (1 mL) followed by addition of Hexane (3 mL). DCM and Hexane were evaporated to dryness and the off-white solid was dried under high vacuum. The product was obtained as an off-white solid (157 mg, quantitative yield).

$^1$H-NMR (CDCl$_3$): δ 7.42 (d, J=8.0 Hz, 1H, —CH—NH—CO—Ar—), 7.06 (d, J=2.8 Hz, 2H, Ar—H), 6.99 (m, 1H, —CH$_2$—NH—CO—CH—), 6.62 (d, J=2.6 Hz, 1H, Ar—H), 4.79 (m, 1H, —NH-Boc), 4.58 (q, J=7.3 Hz, 1H, —CO—CH—NH—), 4.33-4.12 (m, 4H, —Ar—O—CH$_2$—), 3.83-3.42 (m, PEG backbone), 3.36 (s, 3H, CH$_3$—O-PEG), 3.30 (q, J=6.1 Hz, 2H, —CH—S—), 3.08 (m, 2H, Boc-NH—CH$_2$—), 2.98 (dd, J=13.8, 6.4 Hz, 2H, —CH—CH$_2$—S—), 2.89-2.77 (m, 6H, —CH—CH$_2$—S—+—CH—S—CH$_2$—), 2.74 (t, J=6.0 Hz, 4H, —CH—CH$_2$—S—CH$_2$—), 2.61 (t, 6.9 Hz, 4H, —CH$_2$—CH$_2$—S—CH$_2$—), 1.83 (m, 4H, —O—CH$_2$—CH$_2$—CH$_2$—S—+Boc-NH—CH$_2$—CH$_2$—CH$_2$—CH$_2$—CH—), 1.51-1.39 (m, 13H, Boc-NH—CH$_2$—CH$_2$—CH$_2$—CH$_2$—CH-+Boc); $^{13}$C-NMR (CDCl$_3$) δ 172.2, 167.1, 167.0, 159.5, 156.3, 136.1, 106.4, 106.3, 79.4, 72.0, 70.6, 70.3, 70.2, 69.5, 62.1, 61.2, 59.1, 53.8, 45.4, 40.2, 38.9, 35.2, 35.1, 35.0, 34.9, 32.2, 31.5, 29.7, 28.5, 28.4, 23.0; FT-IR, ν (cm$^{-1}$): 2885, 1591, 1467, 1452, 1359, 1342, 1278, 1241, 1146, 1101, 960, 948, 842; GPC: Mn=6.4 kDa, PDI=1.06. Expected Mn=5.9 kDa Hybrid 6 (MeO-PEG$_{5kDa}$-Lys(Boc)-dendron-(Ph)$_4$):

72 mg (0.01 mmol) of MeO-PEG$_{5kDa}$-Lys(Boc)-dendron-(OH)$_4$ (5) were dissolved in DCM (1 mL), Phenyl acetic acid (18 mg, 0.15 mmol, 3 eq. per OH) was added. The flask was cooled to 0° C. followed by the addition of DCC (30 mg, 0.15 mmol, 3 eq. per OH) and DMAP (0.1 eq. per OH) dissolved in DCM (1 mL). The reaction was heated to 30° C. and allowed to stir overnight. The crude mixture was filtered and the organic solution was evaporated to dryness. The crude mixture was dissolved in MeOH and loaded on a MeOH based LH20 SEC column. The fractions that contained the product were unified and the MeOH was evaporated in vacuum to yield an oily residue. In order to facilitate the removal of residual MeOH and solidification of the product, the oily residue was re-dissolved in DCM (1 mL) followed by addition of Hexane (3 mL). DCM and Hexane were evaporated to dryness and the obtained solid was dried under high vacuum. The product was obtained as an off-white solid (68 mg, 87% yield).

$^1$H-NMR (CDCl$_3$): δ 7.30-7.15 (m, 20H, Ar—H), 7.03 (d, J=7.9 Hz, 1H, —CH—NH—CO—Ar—), 6.94 (d, J=2.2 Hz, 2H, Ar—H), 6.77 (s, 1H, CH$_2$—NH—CO—CH—), 6.54 (t, J=2.2 Hz, 1H, Ar—H), 4.68 (m, 1H, —NH-Boc), 4.50 (q, J=7.6 Hz, 1H, —CO—CH—NH—), 4.31-4.15 (m, 8H, —CH$_2$—O—CO—), 4.15-4.00 (m, 4H, —Ar—O—CH$_2$—), 3.65-3.54 (m, PEG backbone), 3.33 (s, 3H, CH$_3$—O-PEG), 3.07 (m, 4H, Boc-NH—CH$_2$—+—CH—S—), 2.94-2.76 (m, 8H, —CH—CH$_2$—S—+—CH—S—CH$_2$—), 2.72 (t, J=6.8 Hz, 4H, —CH—CH$_2$—S—C11$_2$—), 2.57 (t, 7.0 Hz, 4H, —CH$_2$—S—CH$_2$—), 2.05-1.59 (m, 4H, —O—CH$_2$—CH$_2$—CH$_2$—S-+Boc-NH—CH$_2$—CH$_2$—CH$_2$—CH$_2$—CH—), 1.37 (m, 13H, Boc-NH—CH$_2$—CH$_2$—CH$_2$—CH$_2$—CH+Boc); *$^{13}$C-NMR(CDCl$_3$): δ 171.4, 166.8, 159.5, 156.1, 136.2, 133.79, 133.75, 129.3, 128.7, 127.23, 127.21, 106.3, 104.7, 81.6, 72.0, 69.7, 69.5, 64.1, 63.8, 59.1, 53.6, 45.5, 41.3, 38.7, 34.8, 32.1, 31.5, 30.3, 29.6, 28.5, 28.3, 22.9; FT-IR, ν (cm$^{-1}$): 2884, 1736, 1599, 1466, 1454, 1359, 1341, 1279, 1240, 1147, 1102, 1060, 958, 948, 842; GPC: Mn=6.3 kDa, PDI=1.04. Expected Mn=6.3 kDa.

*Another digit was added to peaks that have very close chemical shift in order to distinguish between them.

Scheme 5. Preparation of hybrids 1F and 1C.
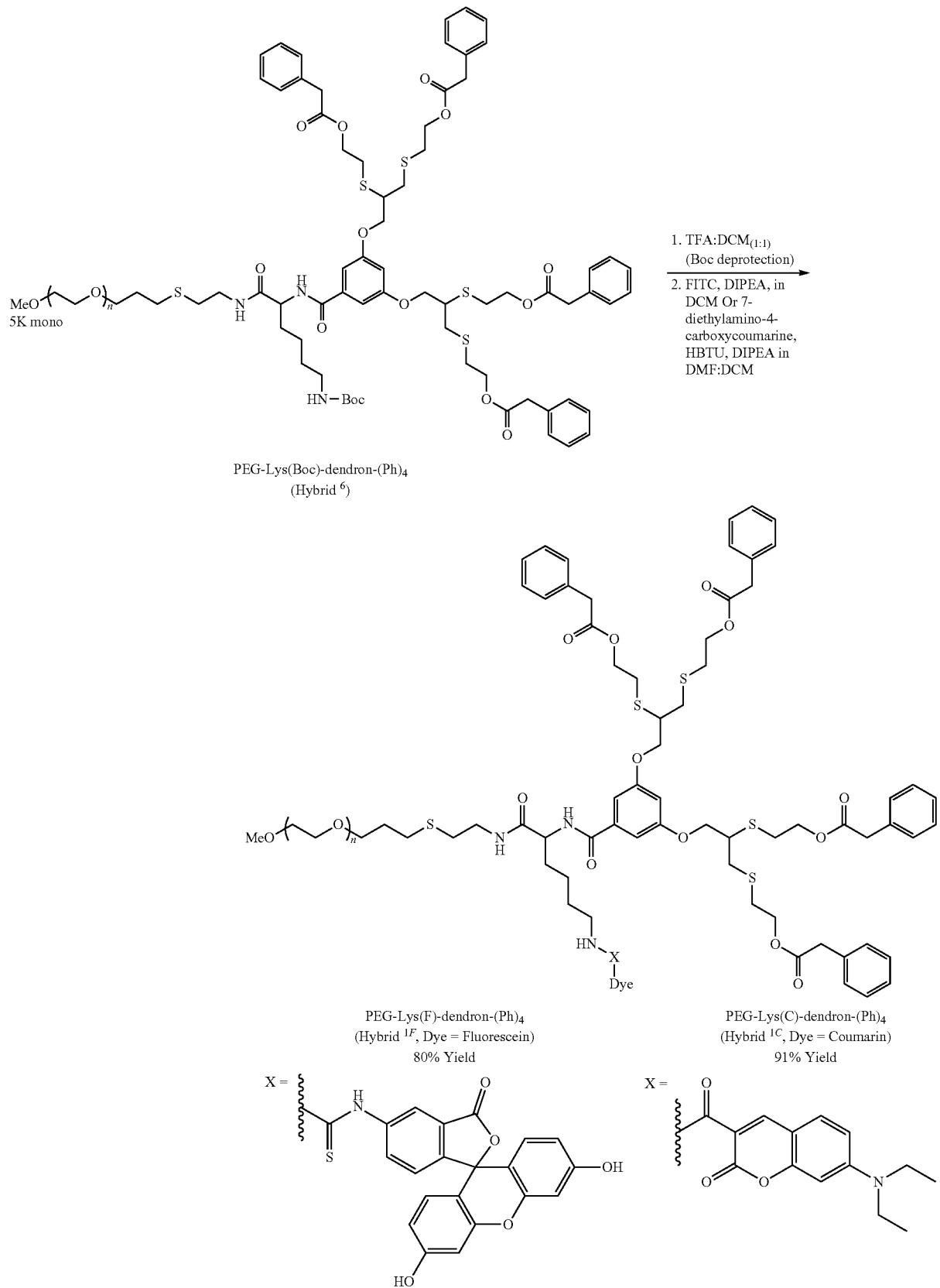

Hybrid 1F (MeO-PEG$_{5kDa}$-Lys(Fluorescein)-dendron-(Ph)$_4$):

60 mg (0.01 mmol) of MeO-PEG$_{5kDa}$-Lys(Boc)-dendron-(Ph)$_4$ (6) were dissolved in DCM (1 mL) and TFA was added (1 mL). After 30 minutes the solution was evaporated to dryness and dried in vacuum. The deprotected hybrid 6 (MeO-PEG$_{5kDa}$-Lys(NH$_2$)-dendron-(Ph)$_4$) was re-dissolved in DMF (1 mL). Fluorescein isothiocyanate (2 eq.) was added followed by addition of DIPEA (20 eq.) and allowed to stir over night. The crude mixture was loaded on a DCM:MeOH 1:1 v/v based LH20 SEC column. The fractions that contained the product were unified and the DCM and MeOH were evaporated in vacuum to yield an oily residue. In order to facilitate the removal of residual MeOH and solidification of the product, the oily residue was re-dissolved in DCM (1 mL) followed by addition of Hexane (3 mL). DCM and Hexane were evaporated to dryness and the obtained orange solid was dried under high vacuum. The product was obtained as an orange solid (50 mg, 80% yield).

$^1$H NMR (CDCl$_3$): δ 8.84 (s, 1H, Ar—OH), 8.10 (s, 1H, Ar—H), 7.91 (d, J=7.8 Hz, 1H, Ar—H), 7.35-7.11 (m, 21H, Ar—H), 7.06-6.93 (m, 4H, Ar—H+—CH—NH—CO—Ar—), 6.72 (s, 2H, Ar—H), 6.66-6.46 (m, 5H, Ar—H), 4.57 (m, 1H, —CO—CH—NH—), 4.30-3.95 (m, 12H, —CH$_2$—O—CO—+—Ar—O—CH$_2$—), 3.78-3.43 (m, PEG backbone), 3.35 (s, CH$_3$—O-PEG), 3.15-3.03 (m, 2H, —CH—S—), 2.95-2.43 (m, 12H, —CH—S—CH$_2$—+—CH—CH$_2$—S—CH$_2$—), 1.95-1.36 (m, 8H, —SC—NH—CH$_2$—CH$_2$—CH$_2$—CH—+—O—CH$_2$—CH$_2$—CH$_2$—S—); $^{13}$C-NMR (CDCl$_3$) δ 181.1, 171.70, 171.5, 169.4, 167.0, 159.7, 152.6, 140.8, 136.1, 133.6, 129.4, 128.7, 127.3, 112.8, 110.5, 106.5, 103.2, 70.7, 70.6, 69.5, 64.2, 63.8, 59.1, 45.6, 44.3, 41.3, 39.0, 35.0, 32.3, 31.6, 30.4, 29.7, 28.4, 23.2; FT-IR, ν (cm$^{-1}$): 2884, 1737, 1592, 1466, 1454, 1359, 1341, 1279, 1240, 1146, 1101, 1060, 1030, 960, 948,842; GPC: Mn=11 kDa, PDI=1.09. Expected Mn=6.6 KDa. MALDI-TOF MS: molecular ion centered at 6.6 kDa.

Hybrid 1C (MeO-PEG$_{5kDa}$-Lys(Coumarin)-dendron-(Ph)$_4$)

31 mg (4.9 μmol) of MeO-PEG$_{5kDa}$-Lys(Boc)-dendron-(Ph)$_4$ (6) were dissolved in DCM (1 mL) and TFA was added (1 mL). After 30 minutes the solution was evaporated to dryness and dried in vacuum. 7-(diethylamino)-3-carboxy coumarin (3 eq.) and HBTU (3 eq.) were dissolved in DCM:DMF 1:1 (1 mL) followed by addition of DIPEA (15 eq.) and allowed to stir for 1 hour. The solution was added to the deprotected hybrid 6 (MeO-PEG$_{5kDa}$-Lys(NH$_2$)-dendron-(Ph)$_4$) dissolved in DCM (1 mL). The reaction was stirred for 1 hours, complete coupling was confirmed by a negative Kaiser test. The crude mixture was loaded on a DCM:MeOH 1:1v/v based LH20 SEC column. The fractions that contained the product were unified and the DCM and MeOH were evaporated in vacuum, further purification was done by resolving the oily residue in DCM (1 mL) followed precipitation by the dropwise addition of Ether (50 mL). The yellow precipitate was filtered and washed twice with Ether and dried under high vacuum. The product was obtained as a yellow solid (29 mg, 91% yield).

$^1$H-NMR (CDCl$_3$): δ 8.89-8.77 (m, 1H, —CH$_2$—CH$_2$—NH—CO—), 8.55 (s, 1H, Ar—H), 7.35 (d, J=9.0 Hz, 1H, Ar—H), 7.25 (m, 20H, Ar—H), 7.01 (m, 3H, Ar—H+—CH—NH—CO—Ar—) 6.77 (m, 1H, —CH$_2$—NH—CO—CH—), 6.64-6.52 (m, 2H, Ar—H), 6.46 (d, J=2.5 Hz, 1H, Ar—H), 4.53 (m, 1H, —CO—CH—NH—), 4.35-3.96 (m, 12H, —CH$_2$—O—CO—+—Ar—O—CH$_2$—), 3.78-3.47 (m, PEG backbone), 3.36 (s, 3H, CH$_3$—O-PEG), 3.11 (m, 2H, —CH—S—), 2.85 (m, 8H, —CH—CH$_2$—S—+—CH—S—CH$_2$—), 2.74 (t, J=6.8 Hz, 4H, —CH—CH$_2$—S—CH$_2$—), 2.60 (t, 7.0 Hz, 4H, —CH$_2$—CH$_2$—S—CH$_2$), 2.04-1.88 (m, 1H, —OC—NH—CH$_2$—CH$_2$—CH$_2$—CH$_2$—CH—), 1.86-1.69 (m, 3H, —O—CH$_2$—CH$_2$—CH$_2$—S—+—OC—NH—CH$_2$—CH$_2$—CH$_2$—CH$_2$—CH—), 1.66-1.57 (m, 2H, —OC—NH—CH$_2$—CH$_2$—CH$_2$—CH—), 1.42 (m, 2H, —OC—NH—CH$_2$—CH$_2$—CH$_2$—CH—), 1.27-1.09 (m, 6H, —N—CH$_2$—CH$_3$); $^{13}$C-NMR (CDCl$_3$): δ 171.8, 171.5, 167.1, 163.5, 162.8, 159.7, 159.6, 157.7, 152.6, 148.1, 133.9, 133.8, 131.3, 129.4, 128.7, 127.3, 110.1, 106.5, 96.7, 72.1, 70.9, 70.7, 69.9, 69.6, 64.2, 63.9, 59.1, 45.6, 45.2, 41.3, 38.8, 35.0, 31.7, 31.6, 30.4, 29.8, 29.7, 29.5, 29.4, 28.4; FT-IR, ν (cm$^{-1}$): 2884, 1736, 1694, 1614, 1584, 1535, 1513, 1466, 1454, 1359, 1341, 1279, 1240, 1146, 1102, 1060, 958, 842; GPC: Mn=6.2 kDa, PDI=1.05. Expected Mn=6.5 kDa. MALDI-TOF MS: molecular ion centered at 6.5 kDa.

Scheme 6. Preparation of hybrids 7F and 7C from hybrids 1F and 1C.

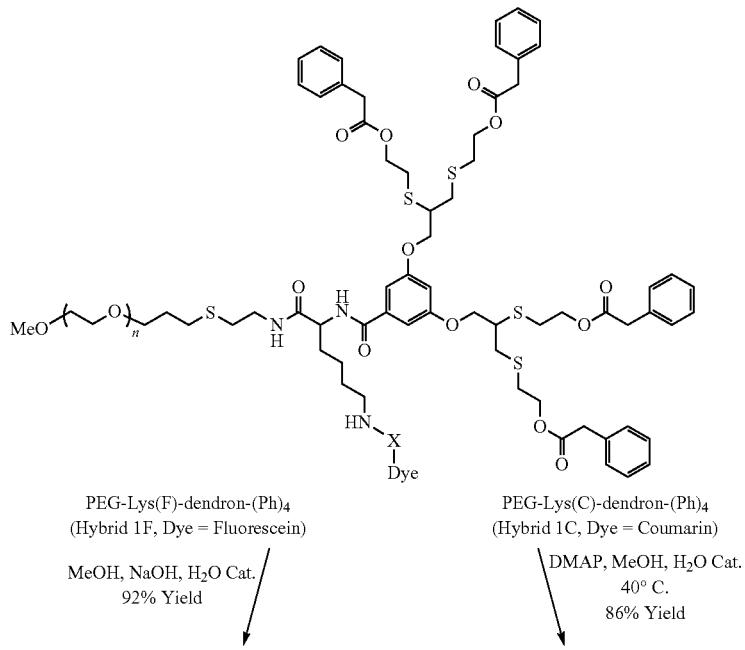

PEG-Lys(F)-dendron-(Ph)$_4$
(Hybrid 1F, Dye = Fluorescein)

MeOH, NaOH, H$_2$O Cat.
92% Yield

PEG-Lys(C)-dendron-(Ph)$_4$
(Hybrid 1C, Dye = Coumarin)

DMAP, MeOH, H$_2$O Cat.
40° C.
86% Yield

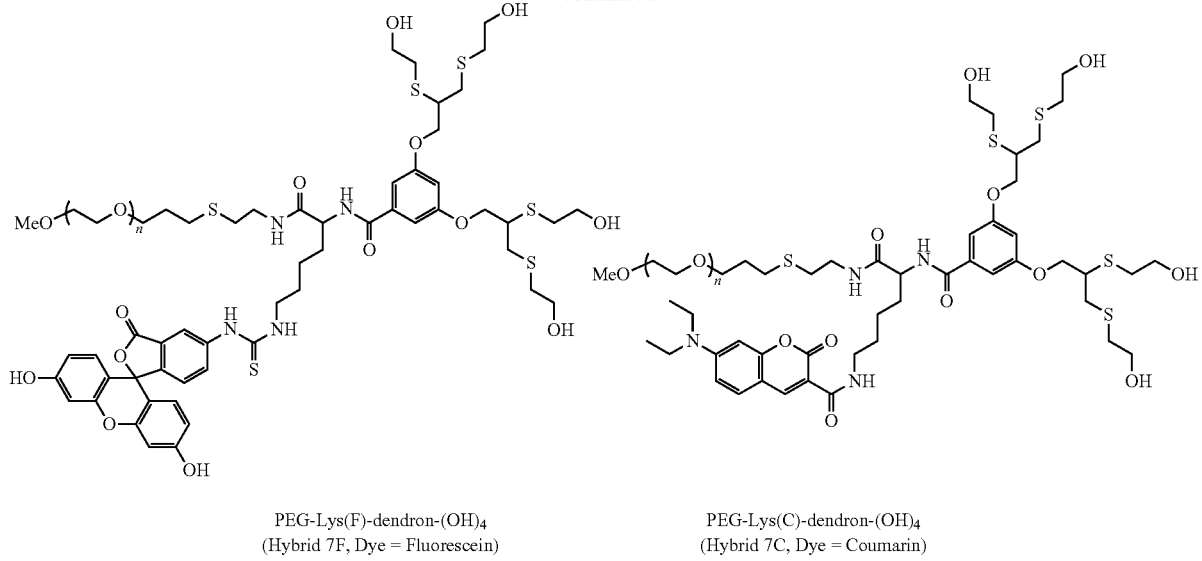

PEG-Lys(F)-dendron-(OH)4
(Hybrid 7F, Dye = Fluorescein)

PEG-Lys(C)-dendron-(OH)4
(Hybrid 7C, Dye = Coumarin)

Hybrid 7F (MeO-PEG$_{5kDa}$-Lys(Fluorescein)-dendron-(OH)$_4$):

35 mg (5.3 μmol) of MeO-PEG$_{5kDa}$-Lys(Fluorescein)-dendron-(Ph)$_4$ (1F) were dissolved in MeOH (1 mL) followed by the addition of a drop of water (cat.) and about 10 μl of NaOH 1N (2 eq.) was added. The mixture was allowed to stir for 20 minutes at 40° C. Complete hydrolysis was confirmed by HPLC. The crude mixture was loaded on a DCM:MeOH 1:1 v/v based LH20 SEC column. The fractions that contained the product were unified and the DCM and MeOH were evaporated in vacuum. In order to facilitate the removal of residual MeOH and solidification of the product, the oily residue was re-dissolved in DCM (1 mL) followed by addition of Hexane (3 mL). DCM and Hexane were evaporated to dryness and the obtained orange solid was dried under high vacuum. The product was obtained as an orange solid (30 mg, 92% yield).

$^1$H NMR (MeOD): δ 8.03 (s, 1H, Ar—H), 7.70 (d, J=9.0 Hz, 1H, Ar—H), 7.11 (m, 3H, Ar—H), 6.86 (s, 1H, Ar—H), 6.76 (s, 1H, Ar—H), 6.68 (s, 2H, Ar—H), 6.60 (m, 2H, Ar—H), 4.54 (m, 1H, —CO—CH—NH—), 4.42-4.08 (m, 4H, —Ar—O—CH$_2$—), 3.81-3.45 (m, PEG backbone), 3.35 (s, 3H, CH$_3$—O-PEG), 2.98 (m, 4H, —CH—CH$_2$—S—), 2.84-2.76 (m, 4H, —CH—S—CH$_2$—), 2.75-2.57 (m, 8H, —CH—CH$_2$—S—CH$_2$—+—CH$_2$—CH$_2$—S—CH$_2$—), 2.10-1.68 (m, 6H, —O—CH$_2$—CH$_2$—CH$_2$—S—+—SC—NH—CH$_2$—CH$_2$—CH$_2$—CH$_2$—CH—), 1.59 (m, 2H, —SC—NH—CH$_2$—CH$_2$—CH$_2$—CH$_2$—CH—); $^{13}$C-NMR (MeOD): δ 176.4, 173.1, 168.2, 159.9, 136.0, 130.0, 129.6, 115.9, 106.4, 104.9, 102.4, 81.8, 77.6, 71.7, 69.8, 69.2, 63.4, 61.7, 61.3, 57.8, 54.2, 45.5, 38.9, 35.2, 35.0, 34.6, 33.8, 33.4, 30.7, 29.6, 29.4, 29.3, 29.1, 29.0, 28.9, 27.9, 26.8, 25.6, 23.3, 22.9, 22.4, 13.1; FT-IR, v (cm$^{-1}$): 2883, 1591, 1466, 1454, 1359, 1341, 1279, 1241, 1147, 1099, 1060, 961, 947, 841; GPC: Mn=10.5 kDa, PDI=1.18. Expected Mn=6.2 kDa. MALDI-TOF MS: molecular ion centered at 6.2 kDa.

Hybrid 7C (MeO-PEG$_{5kDa}$-Lys(Coumarin)-dendron-(OH)$_4$):

20 mg (3.1 μmol) of MeO-PEG$_{5kDa}$-Lys(Coumarin)-dendron-(Ph)$_4$ (1C) were dissolved in MeOH (1 mL) and followed by addition of DMAP (30 eq.) and a drop of water (cat.). The mixture was allowed to stir for 7 days at 40° C. Complete hydrolysis was confirmed by HPLC. The crude mixture was loaded on a DCM:MeOH 1:1 v/v based LH20 SEC column. The fractions that contained the product were unified and the DCM and MeOH were evaporated in vacuum. In order to facilitate the removal of residual MeOH and solidification of the product, the oily residue was re-dissolved in DCM (1 mL) followed by addition of Hexane (3 mL). DCM and Hexane were evaporated to dryness and the obtained orange solid was dried under high vacuum. The product was obtained as a yellow solid (16 mg, 86% yield).

$^1$H-NMR (CDCl$_3$): δ 8.89 (m, 1H, —CH$_2$—CH$_2$—NH—CO—), 8.53 (s, 1H, Ar—H), 7.38 (d, J=9.0 Hz, 1H, Ar—H), 7.22-7.04 (m, 3H, —CH—NH—CO—Ar—+Ar—H), 6.98 (m, 1H, —CH$_2$—NH—CO—CH—), 6.75-6.57 (m, 2H, Ar—H), 6.47 (s, 1H, Ar—H), 4.56 (m, 1H, —CO—CH—NH—), 4.38-4.14 (m, 4H, —CH$_2$—O—CO—), 3.82-3.44 (m, PEG backbone), 3.37 (s, 7H, CH$_3$—O-PEG+—CH—S—), 2.97 (dd, J=13.7, 6.2 Hz, 2H, —CH—CH$_2$—S—), 2.92-2.70 (m, 10H, —CH—CH$_2$—S—CH$_2$—+—CH—S—CH$_2$—), 2.62 (t, 6.9 Hz, 4H, —CH$_2$—CH$_2$—S—CH$_2$—), 1.88-1.41 (m, 8H, —O—CH$_2$—CH$_2$—CH$_2$—S—+—OC—NH—CH$_2$—CH$_2$—CH$_2$—CH$_2$—CH), 1.37-1.21 (m, 28H, —N—CH$_2$—CH$_3$+Hexane); $^{13}$C-NMR (CDCl$_3$): δ 172.4, 162.8, 159.4, 157.7, 154.7, 152.7, 148.6, 136.4, 131.3, 130.1, 129.8, 127.5, 110.1, 108.4, 106.4, 99.5, 96.6, 89.0, 72.0, 70.2, 69.5, 63.7, 62.1, 61.1, 59.1, 57.1, 53.9, 52.2, 45.3, 45.2, 42.5, 38.8, 37.0, 36.3, 36.0, 35.1, 35.0, 33.8, 32.0, 31.5, 30.7, 29.8, 29.7, 29.4, 29.2, 28.4, 27.8, 27.3, 25.6, 23.6, 23.1, 22.8, 16.4, 14.2, 13.1, 12.53, 10.94; FT-IR, v (cm$^{-1}$): 2884, 1612, 1586, 1467, 1451, 1359, 1342, 1279, 1240, 1146, 1102, 1061, 961, 947, 842; GPC: Mn=5.6 kDa, PDI=1.04. Expected Mn=6.0 kDa. MALDI-TOF MS: molecular ion centered at 6.0 kDa.

Scheme 7A. Preparation of hybrids 9, 10C, 8′C and 8C.
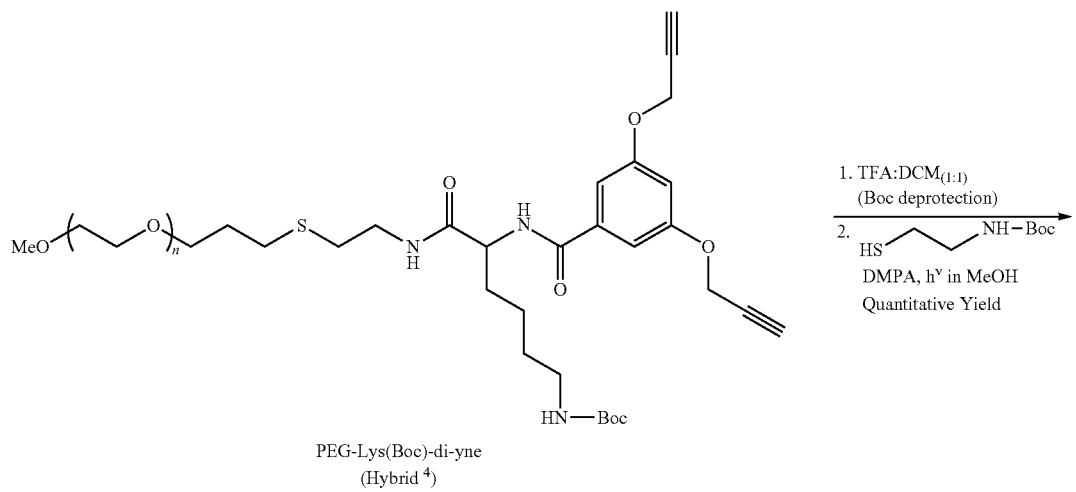
PEG-Lys(Boc)-di-yne
(Hybrid 4)
1. TFA:DCM(1:1)
   (Boc deprotection)
2. HS~~~NH—Boc
   DMPA, hν in MeOH
   Quantitative Yield
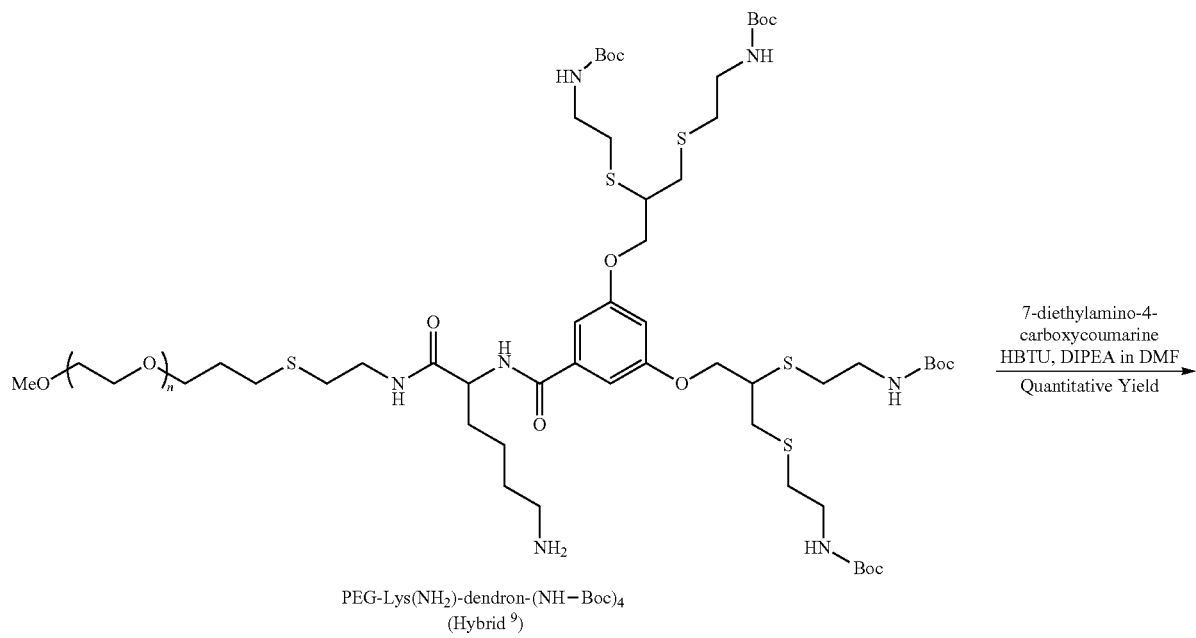
PEG-Lys(NH₂)-dendron-(NH—Boc)₄
(Hybrid 9)
7-diethylamino-4-carboxycoumarine
HBTU, DIPEA in DMF
Quantitative Yield -continued
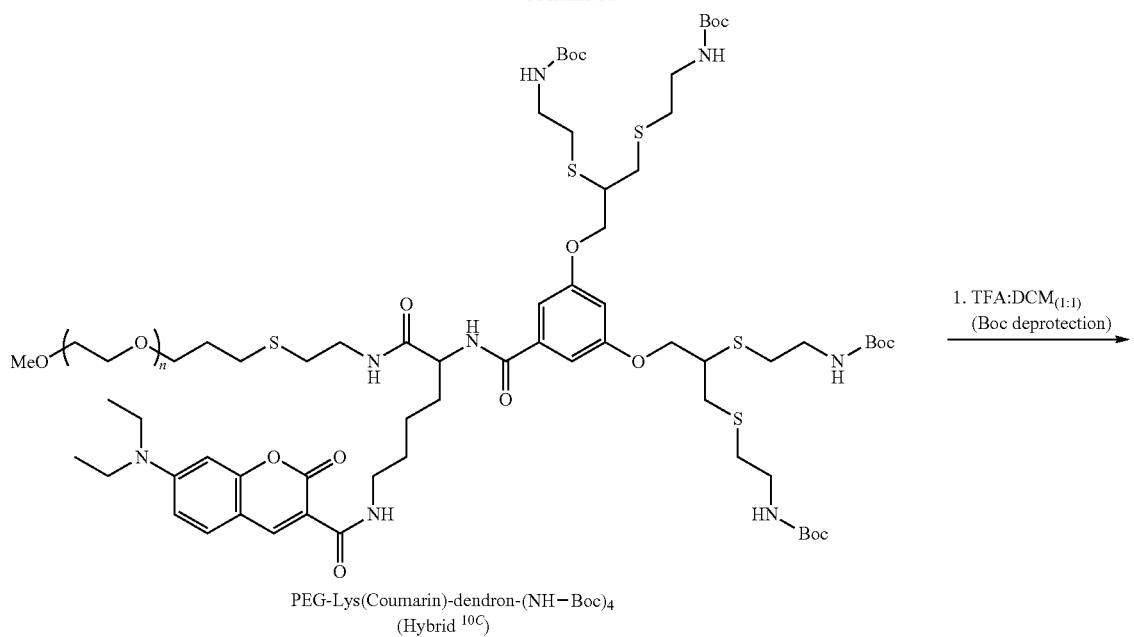
PEG-Lys(Coumarin)-dendron-(NH—Boc)$_4$
(Hybrid $^{10C}$)
1. TFA:DCM$_{(1:1)}$
(Boc deprotection)
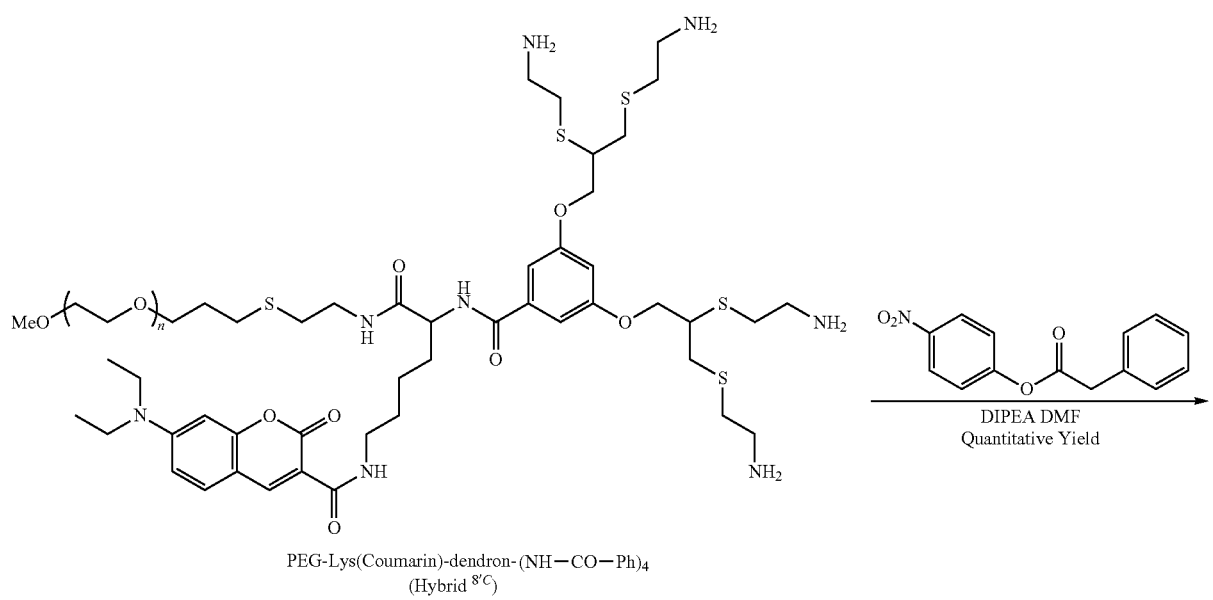
PEG-Lys(Coumarin)-dendron-(NH—CO—Ph)$_4$
(Hybrid $^{8'C}$)
DIPEA DMF
Quantitative Yield

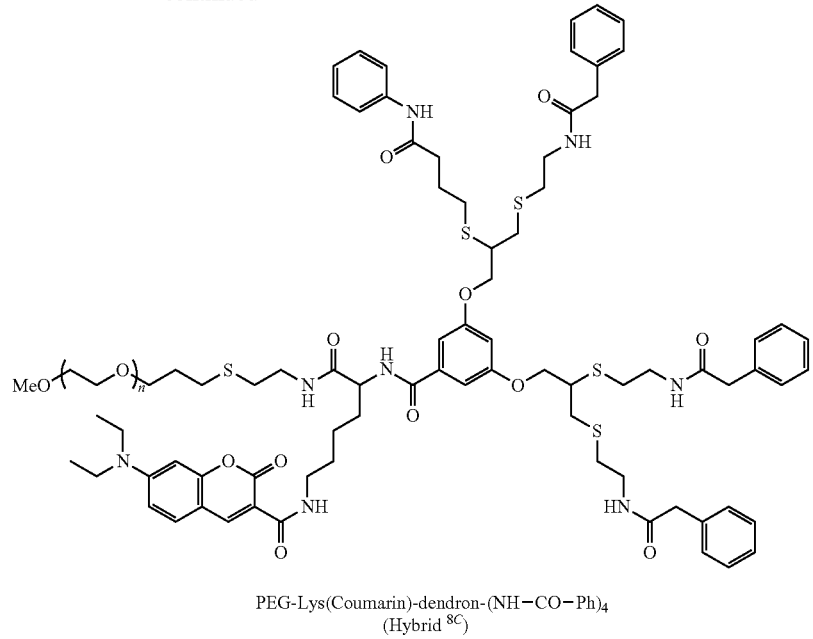

PEG-Lys(Coumarin)-dendron-(NH—CO—Ph)$_4$
(Hybrid $^{8C}$)

Hybrid 9 MeO-PEG$_{5kDa}$-Lys(NH$_2$)-dendron-(NH-Boc)$_4$):

150 mg (0.03 mmol) of MeO-PEG$_{5kDa}$-Lys(Boc)-di-yne (4) were dissolved in DCM (1 mL) and TFA was added (1 mL). After 30 minutes the unprotected product MeO-PEG$_{5kDa}$-Lys(NH$_2$)-di-yne was precipitated by the dropwise addition of Ether (50 mL). The white precipitate was filtered and washed twice with Ether and dried under high vacuum. The product was dissolved in MeOH (1 mL). 2-(Boc-amino)-ethanethiol (80 eq.) and DMPA (0.8 eq.) were added. The solution was purged with nitrogen for minutes and then placed under UV light at 365 nm for 2 hours. The crude mixture was loaded on a MeOH based LH20 SEC column. The fractions that contained the product were unified and the MeOH was evaporated in vacuum to yield an oily residue. In order to facilitate the removal of residual MeOH and solidification of the product, the oily residue was re-dissolved in DCM (1 mL) followed by addition of Hexane (3 mL). DCM and Hexane were evaporated to dryness and the off-white solid was dried under high vacuum. The product was obtained as an off-white solid (162 mg, quantitative yield).

$^1$H-NMR (CDCl$_3$): δ 7.61 (s, 1H, —NH$_2$), 7.07 (s, 2H, Ar—H), 6.58 (d, J=2.2 Hz, 1H, Ar—H), 5.04-5.22 (m, 4H, —NH-Boc), 4.62 (q, J=7.8 Hz, 1H, —CO—CH—NH—), 4.07-4.29 (m, 4H, —Ar—O—CH$_2$—), 3.40-3.80 (m, PEG backbone), 3.35 (s, 3H, CH$_3$—O-PEG), 3.31 (m, 8H, —CH$_2$—NH-Boc), 3.17-3.08 (m, 2H, —CH—S—), 2.90 (m, 6H, —CH—CH$_2$—S—+NH$_2$—CH$_2$—), 2.75 (t, J=6.9 Hz, 4H, —CH—CH$_2$—S—CH$_2$—), 2.70-2.60 (m, 6H, —CH—S—CH$_2$—+—CH$_2$—CH$_2$—S—CH$_2$—), 2.57 (t, J=7.1 Hz, 2H, —CH$_2$—CH$_2$—S—CH$_2$—), 2.05-1.60 (m, 6H, —O—CH$_2$—CH$_2$—CH$_2$—S—+NH$_2$—CH$_2$—CH$_2$—CH$_2$—CH$_2$—CH—), 1.40 (m, 40H, Boc+NH$_2$—CH$_2$—CH$_2$—CH$_2$—CH$_2$—CH—); $^{13}$C-NMR (CDCl$_3$): δ 171.5, 166.2, 159.0, 155.4, 135.7, 105.9, 104.7, 81.6, 78.9, 76.9, 76.8, 76.6, 76.3, 73.5, 71.4, 71.2, 70.0, 69.9, 69.5, 69.2, 68.9, 66.6, 63.2, 58.5, 53.1, 44.6, 40.0, 39.6, 38.5, 33.9, 32.4, 31.5, 30.9, 29.1, 27.9, 27.8, 22.1; FT-IR, ν (cm$^{-1}$): 2884, 1666, 1593, 1466, 1454, 1360, 1341, 1279, 1240, 1147, 1100, 1060, 960, 948, 842; GPC: Mn=5.0 kDa, PDI=1.13. Expected Mn=6.2 kDa.

Hybrid 10C (MeO-PEG$_{5kDa}$-Lys(Coumarin)-dendron-(NH-Boc)$_4$):

7-(diethylamino)-3-carboxy coumarin[2] (3 eq.) and HBTU (3 eq.) were dissolved in DCM:DMF 1:1 (1 mL) followed by addition of DIPEA (20 eq.) and allowed to stir for 20 minutes. The solution was added to 80 mg (0.01 mmol) of hybrid 9 (MeO-PEG$_{5kDa}$-Lys(NH$_2$)-dendron-(NH-Boc)$_4$) dissolved in DCM (1 mL). The reaction was stirred for 1 hours, complete coupling was confirmed by a negative Kaiser test. The crude mixture was loaded on a DCM:MeOH 1:1v/v based LH20 SEC column. The fractions that contained the product were unified and the DCM and MeOH were evaporated in vacuum, further purification was done by resolving the oily residue in DCM (1 mL) followed precipitation by the dropwise addition of Ether (50 mL). The yellow precipitate was filtered and washed twice with Ether and dried under high vacuum. The product was obtained as a yellow solid (80 mg, quantitative yield).

$^1$H-NMR (CDCl$_3$): δ 8.84 (t, J=5.7 Hz, 1H, —CH$_2$—CH$_2$—NH—CO—), 8.53 (s, 1H, Ar—H), 7.36 (d, J=9.0 Hz, 1H, Ar—H), 7.05 (m, 2H, Ar—H+—CH—NH—CO—Ar—), 6.82 (m, 1H, —CH$_2$—NH—CO—CH—), 6.70-6.55 (m, 2H, Ar—H), 6.47 (d, J=2.3 Hz, 1H, Ar—H), 5.18 (m, 4H, —NH-Boc), 4.52 (m, 1H, —CO—CH—NH—), 4.28-4.05 (m, 4H, —Ar—O—CH$_2$—), 3.81-3.62 (m, PEG backbone), 3.35 (s, 3H, CH$_3$—O-PEG), 3.35-3.20 (m, 8H, —CH$_2$—NH-Boc), 3.18-3.07 (m, 2H, —CH—S—), 2.89 (m, 4H, —CH—CH$_2$—S—), 2.75 (t, J=6.5 Hz, 4H, —CH—CH$_2$—S—CH$_2$—), 2.71-2.60 (m, 6H, —CH—S—CH$_2$—+—CH$_2$—CH$_2$—S—CH$_2$—), 2.57 (t, J=7.2 Hz, 2H, —CH$_2$—CH$_2$—S—CH$_2$—), 2.06-1.74 (m, 4H, —O—CH$_2$—CH$_2$—CH$_2$—S—+—NH—CH$_2$—CH$_2$—CH$_2$—CH$_2$—CH—), 1.72-1.56 (m, 2H, —NH—CH$_2$—CH$_2$—CH$_2$—CH—), 1.41 (s, 44H, Boc+—NH$_2$—CH$_2$—CH$_2$—CH$_2$—CH$_2$—CH—), 1.31-1.16 (m, 16H, —N—CH$_2$—CH$_3$+Hexane); *$^{13}$C—NMR (CDCl3): δ 171.3, 166.6, 163.0, 162.2, 159.0, 157.1, 155.4, 152.1, 147.5, 135.8, 130.7, 109.5, 107.9, 105.8, 105.0, 96.0, 88.5, 81.6, 78.9, 78.5, 76.9, 76.8, 76.6, 76.3, 73.5, 71.4, 71.2, 70.0, 69.7, 69.3, 69.0, 66.6, 63.2, 58.5, 53.3, 51.7, 44.6, 40.95, 39.57, 38.2, 33.9, 32.5, 31.5, 31.0, 29.1, 28.8, 27.9, 27.8, 22.3, 12.0; FT-IR, ν (cm$^{-1}$): 2883, 1693, 1614, 1585, 1564, 1547, 1530, 1513, 1466, 1454, 1359, 1341, 1279, 1240, 1146, 1100, 1060, 960, 948, 841; GPC: Mn=6.3 kDa, PDI=1.09. Expected Mn=6.4 kDa.

*Another digit was added to peaks that have very close chemical shift in order to distinguish between them.

Hybrid 8C (MeO-PEG$_{5kDa}$-Lys(Coumarin)-dendron-(NH—CO-Ph)$_4$):

30 mg (4.6 μmol) of MeO-PEG$_{5kDa}$-Lys(Coumarin)-dendron-(NH-Boc)$_4$ (10C) were dissolved in DCM (1 mL) and TFA was added (1 mL). After 30 minutes the solution was evaporated to dryness and dried in vacuum to afford dendron (8'C). The unprotected product MeO-PEG$_{5kDa}$-Lys(Coumarin)-dendron-(NH$_2$)$_4$ was re-dissolved in DMF (1.5 mL). 4-nitrophenyl 2-phenylacetate (12 eq.) and DIPEA (40 eq.) were added and the reaction was allowed to stir overnight. The crude mixture was loaded on a MeOH based LH20 SEC column. The fractions that contained the product were unified and the MeOH was evaporated in vacuum to yield an oily residue. In order to facilitate the removal of residual MeOH and solidification of the product, the oily residue was re-dissolved in DCM (1 mL) followed by addition of Hexane (3 mL). DCM and Hexane were evaporated to dryness and the yellow solid was dried under high vacuum. The product was obtained as a yellow solid (30 mg, quantitative yield).

$^1$H-NMR (CDCl$_3$): δ 8.80 (t, J=5.6 Hz, 1H—CH$_2$—CH$_2$—NH—CO—), 8.53 (s, 1H, Ar—H), 7.69 (s, 1H, —CH—NH—CO—Ar), 7.35 (d, J=9.0 Hz, 1H, Ar—H), 7.32-7.13 (m, 21H, Ar—H), 7.08 (q, J=2.3 Hz, 2H, Ar—H), 6.99 (m, 1H, —CH$_2$—NH—CO—CH—), 6.61 (d, 2.4 Hz, 1H, Ar—H), 6.55 (s, 1H, Ar—H), 6.45-6.35 (m, 4H, —CH$_2$—NH—CO—CH$_2$—Ar+Ar—H), 4.63-4.42 (m, 1H, —CO—CH—NH—), 4.25-3.98 (m, 4H, —Ar—O—CH$_2$—), 3.81-3.62 (m, PEG backbone), 3.35 (m, CH$_3$—O—PEG), 3.04 (t, J=5.9 Hz, 2H, —CH—S—), 2.87-2.64 (m, 8H, —CH—CH$_2$—S—CH$_2$—), 2.57 (m, 8H, —CH—S—CH$_2$—+—CH$_2$—CH$_2$—S—CH$_2$), 1.98 (m, 1H, —NH—CH$_2$—CH$_2$—CH$_2$—CH$_2$—CH—), 1.79 (m, 3H, —NH—CH$_2$—CH$_2$—CH$_2$—CH$_2$—CH—+—O—CH$_2$—CH$_2$—CH$_2$—S—), 1.62 (q, J=6.7 Hz, 2H, —NH—CH$_2$—CH$_2$—CH$_2$—CH$_2$—CH—), 1.54-1.38 (m, 2H, —NH$_2$—CH$_2$—CH$_2$—CH$_2$—CH$_2$—CH—), 1.20 (t, J=7.1 Hz, 10H, —N—CH$_2$—CH$_3$+Hexane); $^{13}$C-NMR (CDCl$_3$): δ 171.4, 170.8, 166.7, 162.9, 162.2, 158.9, 157.0, 152.0, 147.5, 134.4, 130.6, 128.9, 128.4, 126.7, 109.5, 107.9, 106.0, 104.9, 96.0, 76.9, 76.8, 76.6, 76.3, 71.4, 70.1, 69.6, 69.3, 69.0, 58.5, 53.5, 44.6, 44.2, 43.1, 38.9, 38.5, 33.7, 31.8, 31.0, 30.7, 29.1, 28.8, 27.8, 22.6, 12.0; FT-IR, ν (cm$^{-1}$): 2884, 1693, 1643, 1614, 1583, 1563, 1547, 1536, 1513, 1466, 1454, 1415, 1359, 1341, 1279, 1240, 1146, 1100, 1060, 961, 948, 841; GPC: Mn=6.4 kDa, PDI=1.12. Expected Mn=6.5 kDa. MALDI-TOF MS: molecular ion centered at 6.5 kDa.

An additional hybrid 8F, containing a Fluorescein moiety instead of the Coumarin moiety was prepared according to the same method:

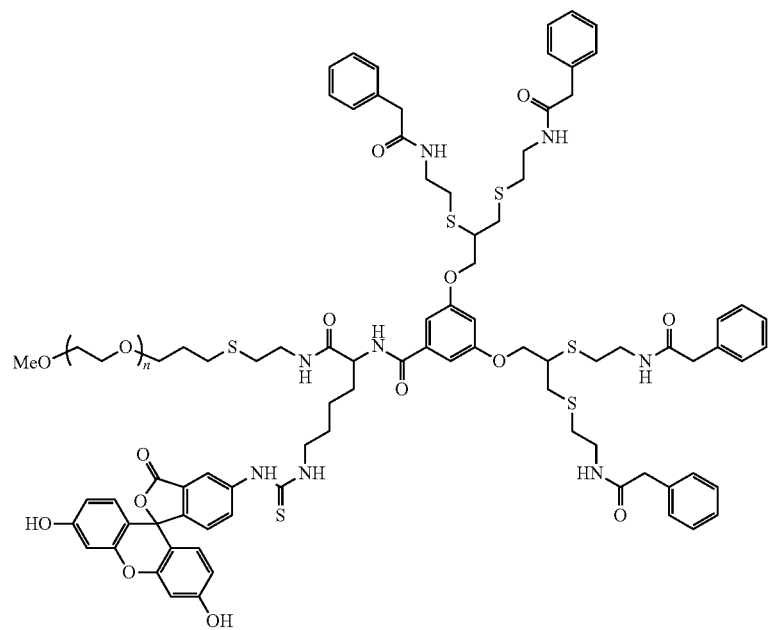

8F

Compounds 8c and 8F may be converted by cleavage of the amide bond to the corresponding hybrids 8(i)C and 8(i)F.

Scheme 7B - Cleavage of hybrids containing fluorescent dyes by amidases. It is apparent to a person of skill in the art that the reaction in Scheme 7B is applicable to other hybrid delivery systems containing a variety of dyes (or MR probes) as described herein.

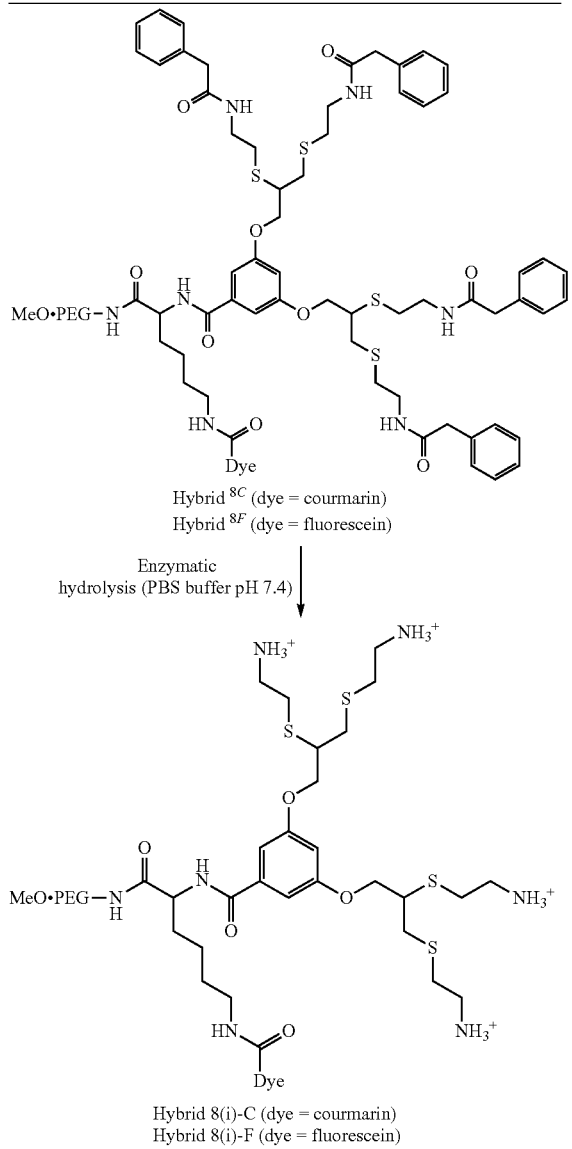

Example 3—Critical Micelle Concentration (CMC) Measurements

Instrument Method:
Excitation: 550 nm
Emission intensity scan: 580-800 nm
Diluent solution preparation: Into 10 ml Phosphate buffer solution (pH 7.4), 4.5 µL of Nile red stock solution (0.88 mg/ml in Ethanol) were added and mixed to give a final concentration of 1.25 µM.

CMC measurement for compound 1F, 1C and 8C: A 800 µM solution was prepared in diluent and sonicated for 15 minutes. This solution was repeatedly diluted by a factor of 1.5 with diluent. 150 µL of each solution were loaded onto a 96 wells plate. The fluorescence emission intensity was scanned for each well. Maximum emission intensity was plotted vs. hybrid concentration in order to determine the CMC. All measurements were repeated 3 times. The CMC for hybrids 1F, 1C and 8C were 6±1 µM, 3±1 µM and 6±1 µM, respectively.

Example 4—Dynamic Light Scattering (DLS)

General Sample Preparation:
Hybrids 1F, 1C and 8C were dissolved in phosphate buffer (pH 7.4) to give a final concentration of 160 µM. Solution was sonicated for 15 minutes and filtered through a 0.22 µm nylon syringe filter. 700 µL of this solution were accurately transferred into a polystyrene cuvette and a measurement was performed (t=0).

For micelle degradation in the presence of 27 nM PLE enzyme: 4.20 µL of PLE enzyme stock solution (14.0 µM in phosphate buffer pH 7.4) was added to 2.20 mL solution of hybrid 1F (160 µM). Measurement was performed after 24 hours.

For micelle degradation in the presence of 270 nM PLE enzyme: 21.5 µL of PLE enzyme stock solution (28.1 µM in PBS buffer pH 7.4) were added to 2.20 mL solution of hybrid 1C (160 µM). Measurement was performed after 24 hours.

Figure 9:
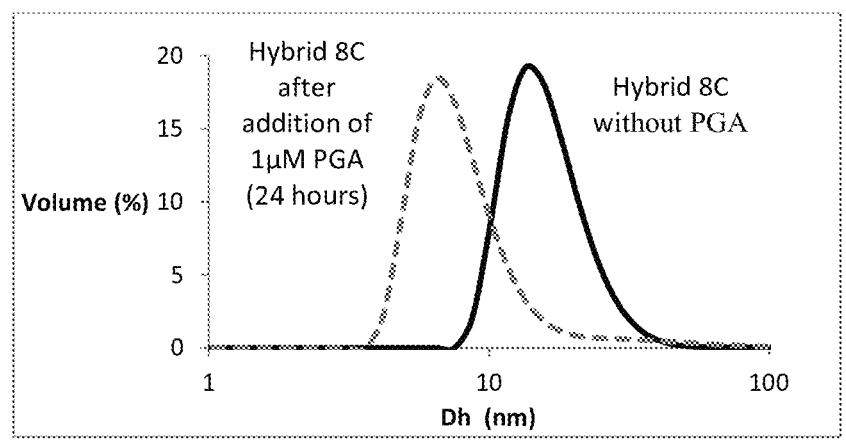
FIG. 9: Micelle degradation of hybrid 8C in presence of 1 µM PGA enzyme (after 24 hours).

For micelle degradation in the presence of 1 µM PGA enzyme: 44.9 µL of PGA enzyme stock solution (50 µM in phosphate buffer pH 7.4) was added to 2.20 mL solution of hybrid 8C (160 µM). Measurement was performed after 24 hours (FIG. 9).

Example 5—Absorbance Measurements

Instrument Method:
Spectra were recorded on TECAN Infinite M200Pro plate reader device.
Absorbance intensity scan: 350-700 nm
Diluted solution preparation of hybrids 1F, 1C, 7F and 7C:
A 160 µM solution was prepared in diluent. Solution was sonicated for 15 minutes and then filtered through a 0.22 µm nylon syringe filter. This solution was repeatedly diluted by a factor of 2 with diluent. 100 µL of each solution were loaded onto a 96 wells plate. The absorbance intensity was scanned for each well. Maximum absorbance intensities were plotted vs. concentrations in order to show the similarity of the molar absorption coefficient.

Figure 10:
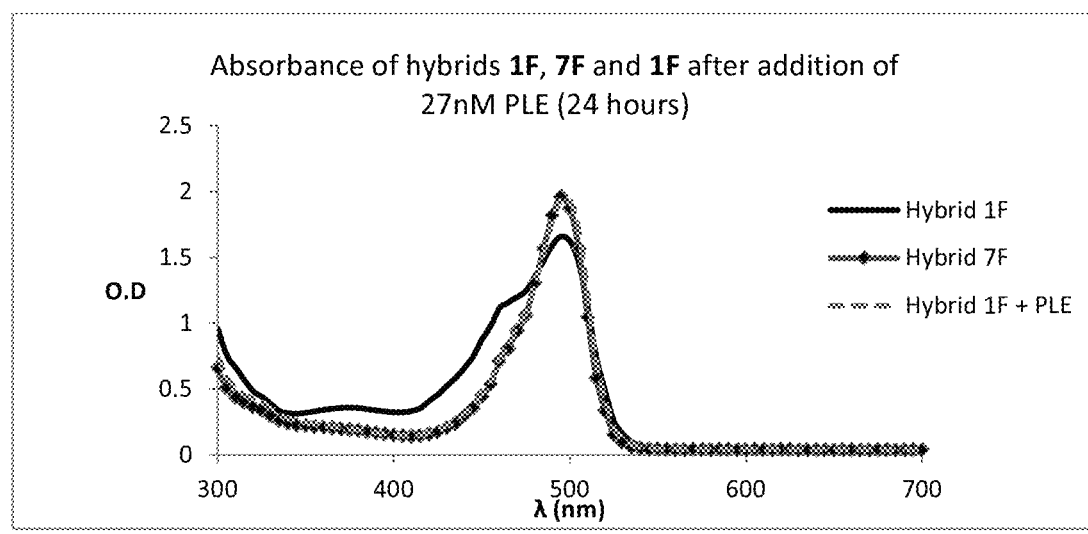
FIG. 10: Absorbance spectra overlay of hybrid 1F (160 µM), hybrid 7F (160 µM) and hybrid 1F (160 µM) after addition of 270 nM PLE enzyme (after 24 hours).

For micelle degradation in the presence of 27 nM PLE enzyme:
4.2 µL of PLE enzyme stock solution (14.004 in phosphate buffer pH 7.4) was added to 2.20 mL solution of hybrid 1F (160 µM). Measurement was performed after 24 hours. (FIG. 10).

Figure 11:
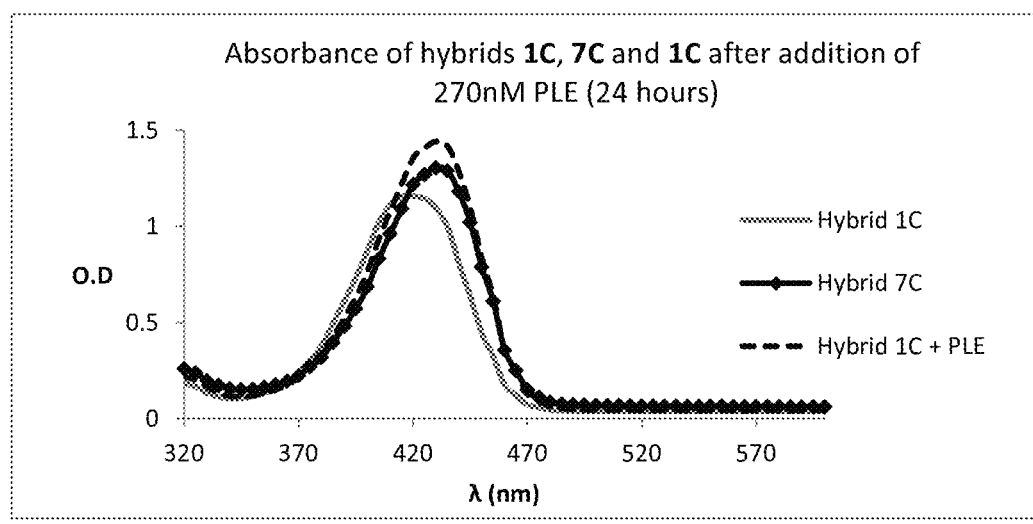
FIG. 11: Absorbance spectra overlay of hybrid 1C (160 µM), hybrid 7C (160 µM) and hybrid 1C (160 µM) after addition of 270 nM PLE enzyme (after 24 hours).

For micelle degradation in the presence of 270 nM PLE enzyme:
21.5 µL of PLE enzyme stock solution (28.1 µM in PBS buffer pH 7.4) were added to 2.20 mL solution of hybrid 1C (160 µM). Measurement was performed after 24 hours. (FIG. 11).

Figure 12:
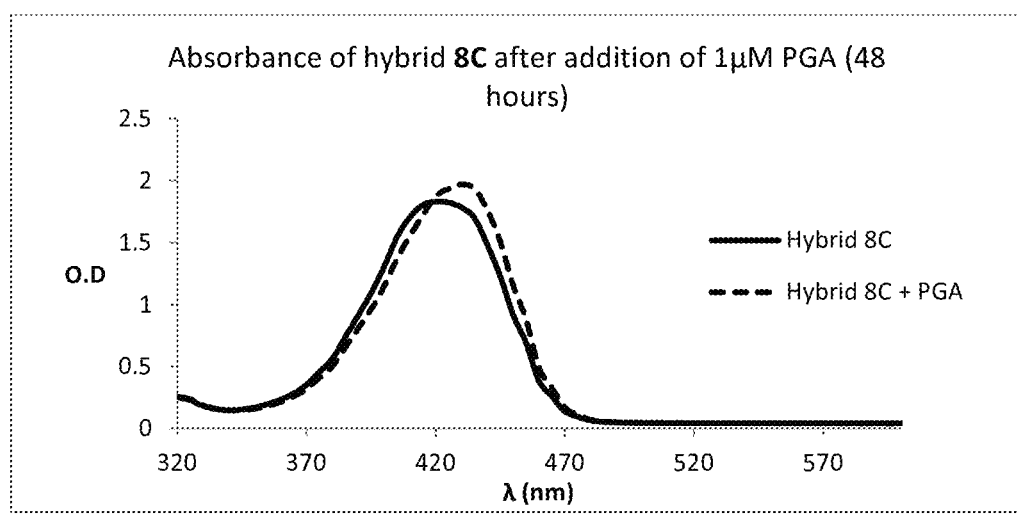
FIG. 12: Absorbance spectra overlay of hybrid 8C (160 µM) and hybrid 1C (160 µM) after addition of 1 µM PGA enzyme (after 48 hours).

For micelle degradation in the presence of 1 µM PGA enzyme:
44.9 µL of PGA enzyme stock solution (50 µM in phosphate buffer pH 7.4) was added to 2.20 mL solution of hybrid 8C (160 µM). Measurement was performed after 48 hours. (FIG. 12).

Example 6—Fluorescence Measurements

Instrument Method of Hybrids 1F and 7F:
Spectra were recorded on TECAN Infinite M200Pro plate reader device:

Excitation: 470 nm
Emission intensity scan: 490-700 nm
Gain: 70
Instrument Method of Hybrids 1C and 7C:
Fluorescence measurements were performed using an Agilent Technologies Cary Eclipse Fluorescence Spectrophotometer:
Excitation: 420 nm
Emission scan: 440-700 nm
Excitation and Emission slits width: 5 nm and 10 nm for the lower concentrations overlay.
Scan rate: 600 nm/min and 700 nm/min for the lower concentrations overlay.
Excitation measurements were performed using Fluorolog 3.22 fluorometer (Horiba) Measurements were taken in front-face mode using a 2 mm cuvette.
Instrument Method of Hybrid 8C:
Spectra were recorded on TECAN Infinite M200Pro plate reader device:
Excitation: 420 nm
Emission intensity scan: 440-700 nm
Gain: 90
Diluted solution preparation of hybrids 1F, 1C, and 8C:
A 160 µM solution was prepared in diluent. Solution was sonicated for 15 minutes and then filtered through a 0.22 µm nylon syringe filter. This solution was repeatedly diluted by a factor of 2 with diluent. 100 µL of each solution were loaded onto a 96 wells plate. The emission intensity was scanned for each well.

For micelle degradation in the presence of 27 nM PLE enzyme:
4.2 µL of PLE enzyme stock solution (14.0 µM in phosphate buffer pH 7.4) was added to 2.20 mL solution of hybrid 1F (160 µM). Measurement was performed after 24 hours.

For micelle degradation in the presence of 270 nM PLE enzyme:
21.5 µL of PLE enzyme stock solution (28.1 µM in phosphate buffer pH 7.4) were added to 2.20 mL solution of hybrid 1C (160 µM). Measurement was performed after 24 hours.

For micelle degradation in the presence of 1 µM PGA enzyme:
44.9 µL of PGA enzyme stock solution (50 µM in phosphate buffer pH 7.4) was added to 2200 µL solution of hybrid 8C (160 µM). Measurement was performed after 48 hours.

Figure 13:
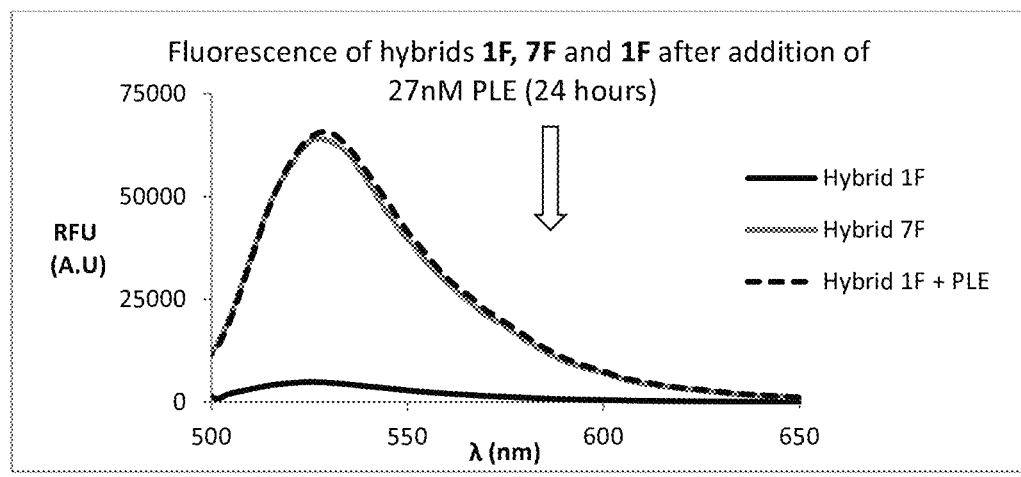
FIG. 13: Fluorescence emission intensity spectra overlay of hybrid 1F (160 µM), hybrid 7F (160 µM) and of hybrid 1F (160 µM) after addition of 27 nM PLE enzyme (after 24 hours).

FIG. 13 depicts the fluorescence emission intensity spectra overlay of hybrid 1F (160 µM), hybrid 7F (160 µM) and of hybrid 1F (160 µM) after addition of 27 nM PLE enzyme (after 24 hours).

Figure 14:
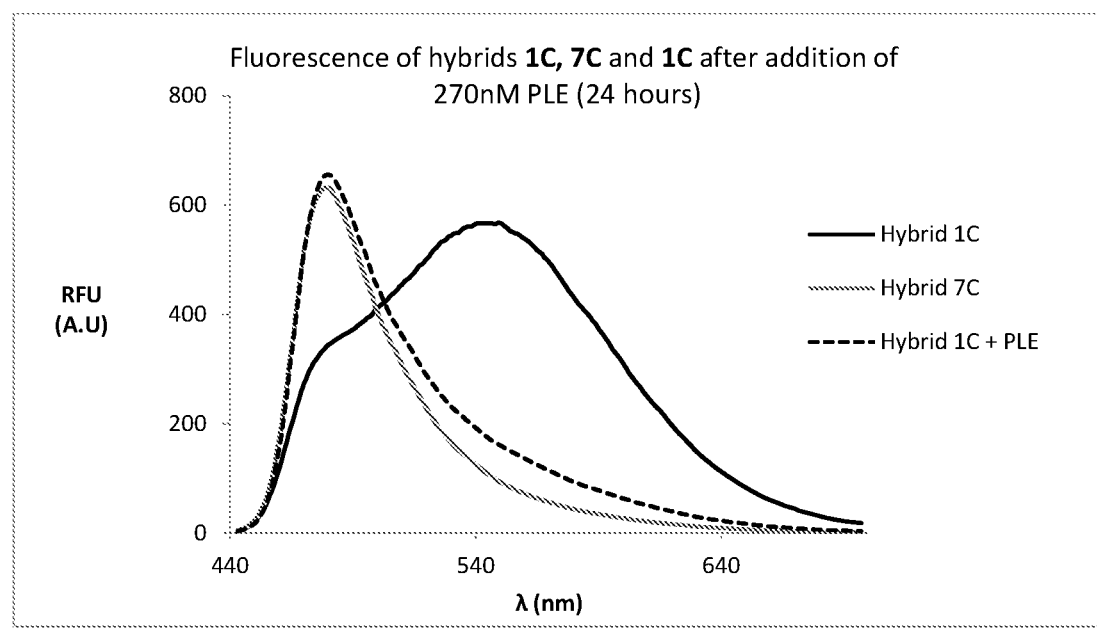
FIG. 14: Fluorescence emission intensity spectra overlay of hybrid 1C (160 µM), hybrid 7C (160 µM) and of hybrid 1C (160 µM) after addition of 270 nM PLE enzyme (after 24 hours).

FIG. 14 depicts the fluorescence emission intensity spectra overlay of hybrid 1C (160 µM), hybrid 7C (160 µM) and of hybrid 1C (160 µM) after addition of 270 nM PLE enzyme (after 24 hours).

Figure 15:
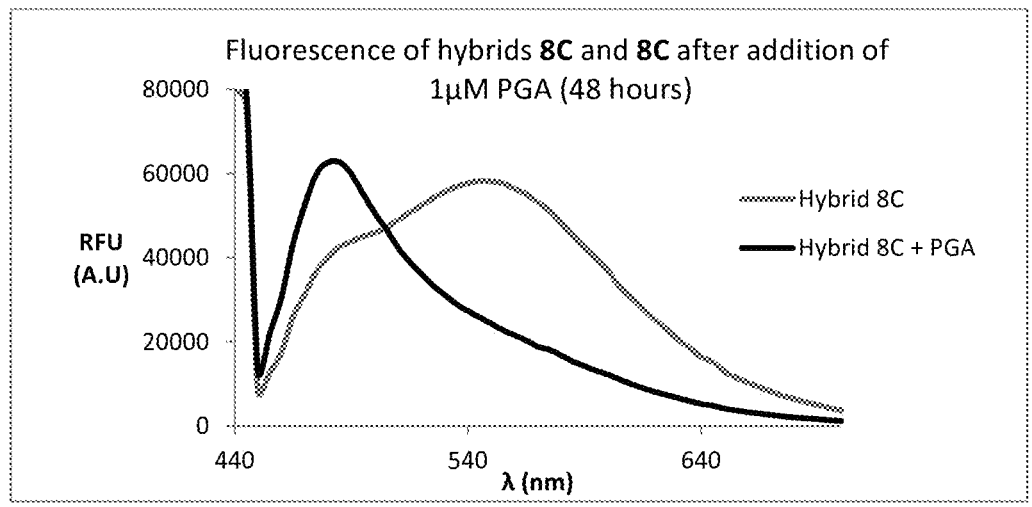
FIG. 15: Fluorescence emission intensity spectra overlay of hybrid 8C (160 µM) and of hybrid 8C (160 µM) after addition of 1 µM PGA enzyme (after 48 hours).

FIG. 15 depicts the fluorescence emission intensity spectra overlay of hybrid 8C (160 µM) and of hybrid 8C (160 µM) after addition of 1 µM PGA enzyme (after 48 hours).

Fluorescence monitoring of enzymatic degradation:
Instrumentation:
Monitoring of micelle disassembly rate by enzymes was performed using an Agilent Technologies Cary Eclipse Fluorescence Spectrophotometer.
Instrument Method Hybrid 1F:
Excitation: 488 nm
Emission scan: 495-700 nm
Excitation and Emission slits width: 5 nm
Scan rate: 480 nm/min
Instrument Method Hybrid 1C and 8C:
Excitation: 420 nm
Emission scan: 440-700 nm
Excitation and Emission slits width: 5 nm
Scan rate: 600 nm/min
Sample Preparation and Measurement:
Hybrid 1F was dissolved in phosphate buffer (pH 7.4) to give a concentration of 160 µM. Solution was sonicated for 15 minutes and then filtered through a 0.22 µm nylon syringe filter. 700 µL were accurately transferred to a quartz cuvette. A fluorescence emission scan was performed (t=0). 4.2 µL of PLE enzyme stock solution (14.0 µM in phosphate buffer pH 7.4) were added to 2.20 mL solution of hybrid 1F (160 µM) and mixed for 10 seconds (vortex mixer) to give final PLE concentration of 27 nM. 700 µL were accurately transferred to a quartz cuvette. Repeating fluorescence scans were performed every 15 minutes for 16 hours. All measurements were repeated 3 times.

Hybrid 1C was dissolved in phosphate buffer (pH 7.4) to give a concentration of 160 µM. Solution was sonicated for 15 minutes and then filtered through a 0.22 µm nylon syringe filter. 700 µL were accurately transferred to a quartz cuvette. A fluorescence emission scan was performed (t=0). 21.5 µL of PLE enzyme stock solution (28.1 µM in phosphate buffer pH 7.4) were added to 2.20 mL solution of hybrid 1C (160 µM) and mixed for 10 seconds (vortex mixer) to give final PLE concentration of 270 nM. 700 µL were accurately transferred to a quartz cuvette. Repeating fluorescence scans were performed every 15 minutes for 15 hours. All measurements were repeated 3 times.

Hybrid 8C was dissolved in phosphate buffer (pH 7.4) to give a concentration of 160 µM. Solution was sonicated for 15 minutes and then filtered through a 0.22 µm nylon syringe filter. 700 µL were accurately transferred to a quartz cuvette. A fluorescence emission scan was performed (t=0). 44.9 µL of PGA enzyme stock solution (50 µM in phosphate buffer pH 7.4) were added to 2.20 mL solution of hybrid 8C (160 µM) and mixed for 10 seconds (vortex mixer) to give final PGA concentration of 1 µM. 700 µL were accurately transferred to a quartz cuvette. Repeating fluorescence scans were performed every 15 minutes for 13 hours. All measurements were repeated 3 times.

Example 7—HPLC Monitoring of Enzymatic Degradation

Instrument Method:
Column: Phenomenex, Aeris WIDEPORE, C4, 150×4.6 mm, 3.6 µm.
Column Temperature: 30° C.
Mobile Phase: Solution A: 0.1% $HClO_4$ in $H_2O$:Acetonitrile 95:5 V/V.
Solution B: 0.1% $HClO_4$ in $H_2O$:Acetonitrile 5:95 V/V.
Solution C: THF.
Gradient Program:

| Time [min] | % Sol. A | % Sol. B | % Sol. C |
|---|---|---|---|
| 0.0 | 95 | 0 | 5 |
| 1.0 | 95 | 0 | 5 |
| 20.0 | 0 | 95 | 5 |
| 23.0 | 0 | 95 | 5 |
| 23.1 | 95 | 0 | 5 |
| 30.0 | 95 | 0 | 5 |

Injection volume: 30 µL.
Detector: UV at 295 nm, 2 Hz detection rate.
Needle Wash: MeOH.
Seal wash solution: $H_2O$:MeOH 90:10 V/V.
Diluent: phosphate buffer pH 7.4.

General Sample Preparation:

All hybrids were dissolved in phosphate buffer to give a concentration of 160 μM. Solution was sonicated for 15 minutes and then filtered through a 0.22 μm nylon syringe filter.

For enzymatic cleavage of hybrid 1F in the presence of 27 nM PLE enzyme:

300 μL of the 160 μM 1F solution were transferred to a proper vial. 30 μL were injected to the HPLC as t=0 injection. 2.20 mL of the 160 μM 1F solution were transferred to a proper vial. 4.41 μL of PLE (14.0 μM) stock solution in phosphate buffer (pH 7.4) were added and mixed manually. 1.50 mL were transferred to a proper vial (700 μL were accurately transferred to a quarts cuvette for monitoring enzymatic degradation of micelles by fluorescence measurements). Enzymatic degradation was monitored by repeating 30 μL injections from the same vial over 16 hours. All measurements were repeated 3 times.

For enzymatic cleavage of hybrids 1C in the presence of 270 nM PLE enzyme:

300 μL of the 160 μM 1C solution were transferred to a proper vial. 30 μL were injected to the HPLC as t=0 injection. 2.20 mL of the 160 μM 1C solution were transferred to a proper vial. 21.5 μL of PLE (28.1 μM) stock solution in phosphate buffer (pH 7.4) were added and mixed manually. 1.50 mL were transferred to a proper vial (700 μL were accurately transferred to a quarts cuvette for monitoring enzymatic degradation of micelles by fluorescence measurements). Enzymatic degradation was monitored by repeating 30 μL injections from the same vial over 15 hours. All measurements were repeated 3 times.

For enzymatic cleavage of hybrids 8C in the presence of 1 μM PGA enzyme:

300 μL of the 160 μM 8C solution were transferred to a proper vial. 30 μL were injected to the HPLC as t=0 injection. 2.2 omL of the 160 μM 8C solution were transferred to a proper vial. 44.9 μL of PGA (50 μM) stock solution in phosphate buffer (pH 7.4) were added and mixed manually. 1.5 omL were transferred to a proper vial (700 μL were accurately transferred to a quarts cuvette for monitoring enzymatic degradation of micelles by fluorescence measurements). Enzymatic degradation was monitored by repeating 30 μL injections from the same vial over 13 hours. The overlay shows accumulation of partially cleaved hybrids with the enzymatic degradation. All measurements were repeated 3 times.

FIG. 16 depicts the HPLC monitoring of micelle degradation in presence of 27 nM PLE enzyme for hybrid 1F over time.

FIG. 17 depicts the HPLC monitoring of micelle degradation in presence of 270 nM PLE enzyme for hybrid 1C over time.

Figure 18:
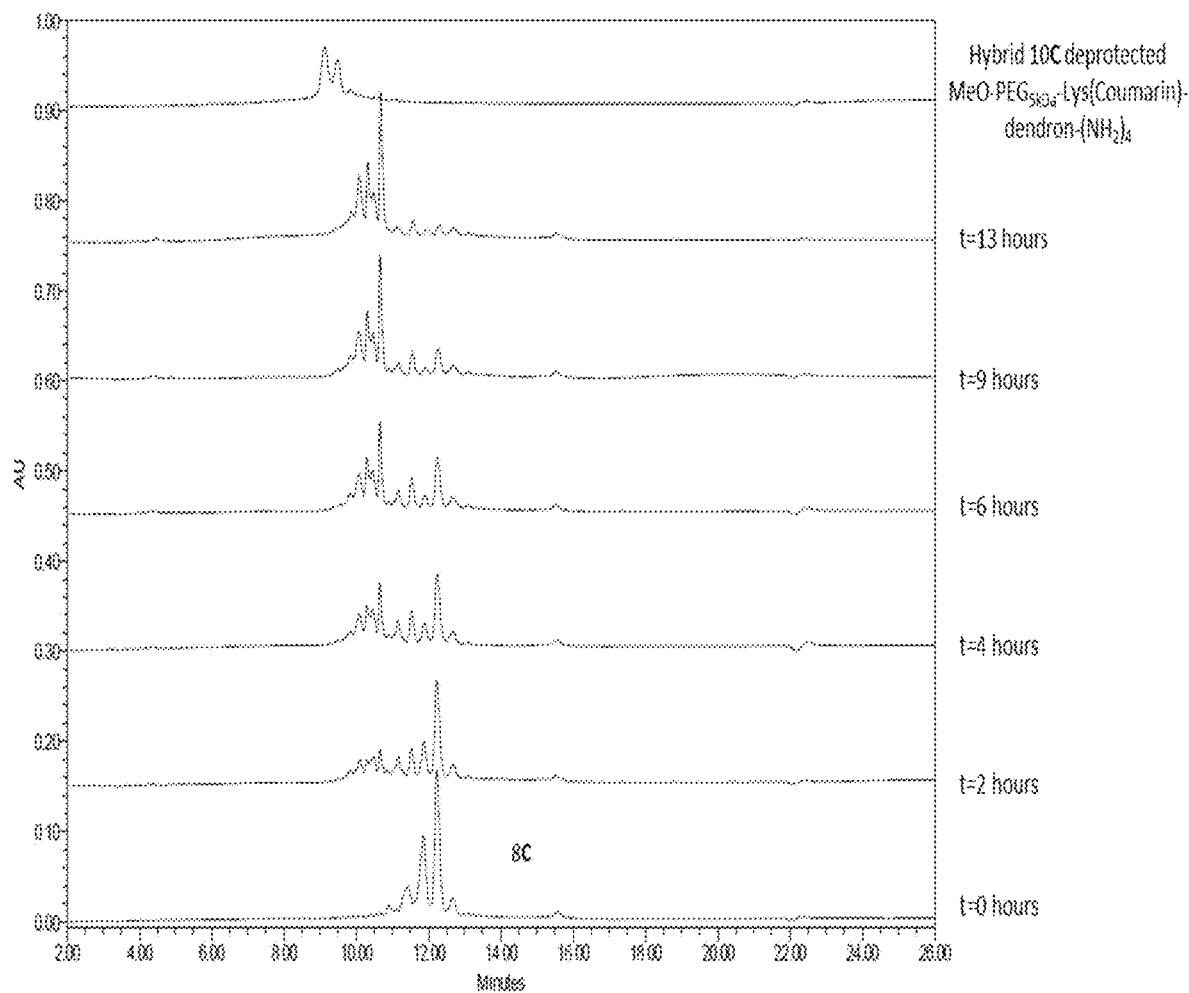
FIG. 18: HPLC monitoring of micelle degradation in presence of 1 µM PGA enzyme for hybrid 8C over time. The overlay shows accumulation of partially cleaved hybrids.
Figure 19:
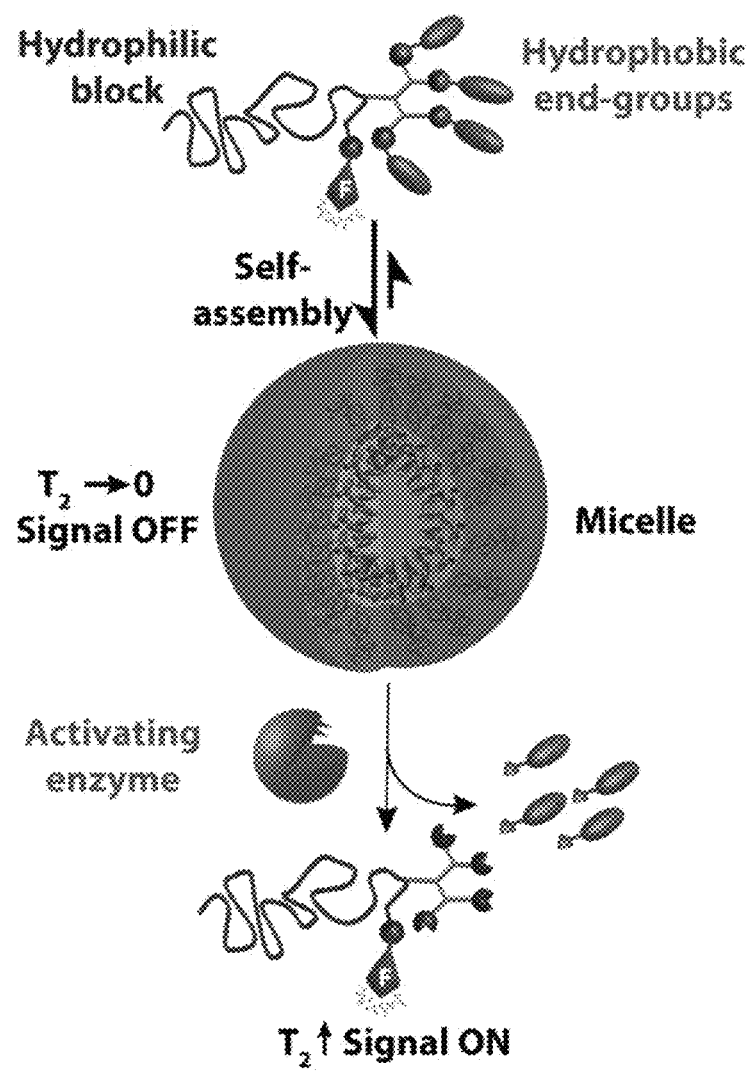

FIG. 18 depicts the HPLC monitoring of micelle degradation in presence of 1 μM PGA enzyme for hybrid 8C over time. The overlay shows accumulation of partially cleaved hybrids.

Example 8—Preparation of Additional MeO-PEG$_{5kDa}$-Lys(Labeled)-dendron-(Aliphatic)$_4$ Hybrids Containing Fluorescent Probes Additional hybrids were synthesized from MeO-PEG$_{5kDa}$-Lys(Boc)-dendron-(OH)$_4$[1] (5) as generally described in Scheme 8. Esterification with an aliphatic carboxylic acid yielded hybrid (11) with four enzymatically cleavable end-groups. The BOC group was removed with trifluoroacetic acid, followed by conjugation of the dye to the protected amine to yield amphiphilic hybrids. Embodiments of hybrids with specific labeling groups are depicted in Schemes 9-12 hereinbelow.

Scheme 8. General procedure for preparation of labelled aliphatic hybrids.

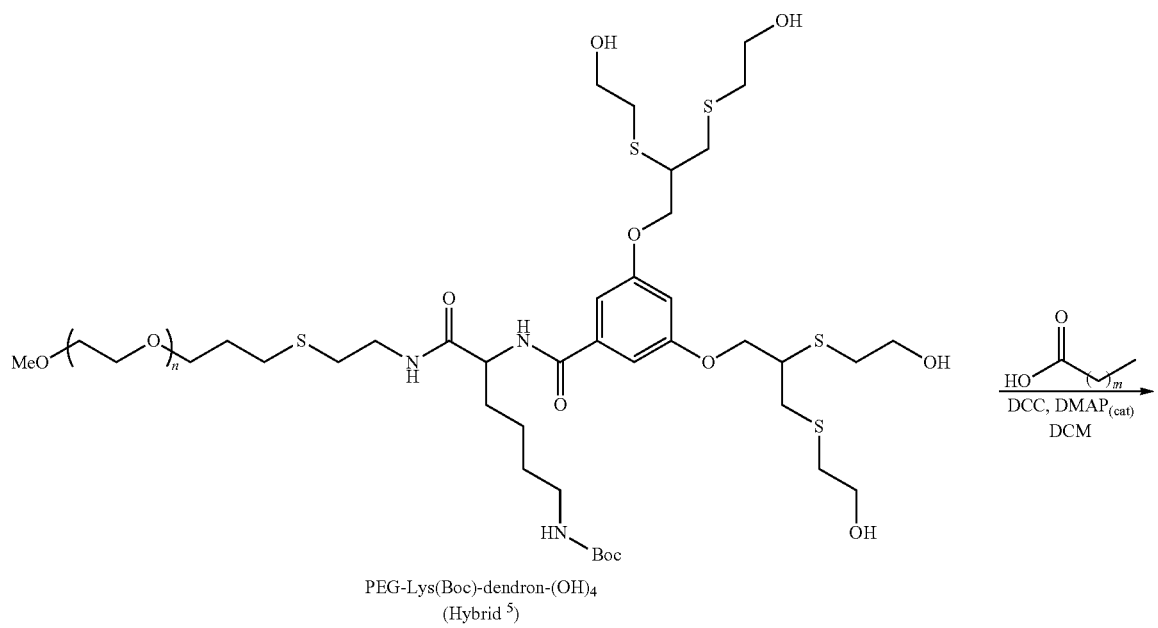

PEG-Lys(Boc)-dendron-(OH)$_4$
(Hybrid [5])

-continued

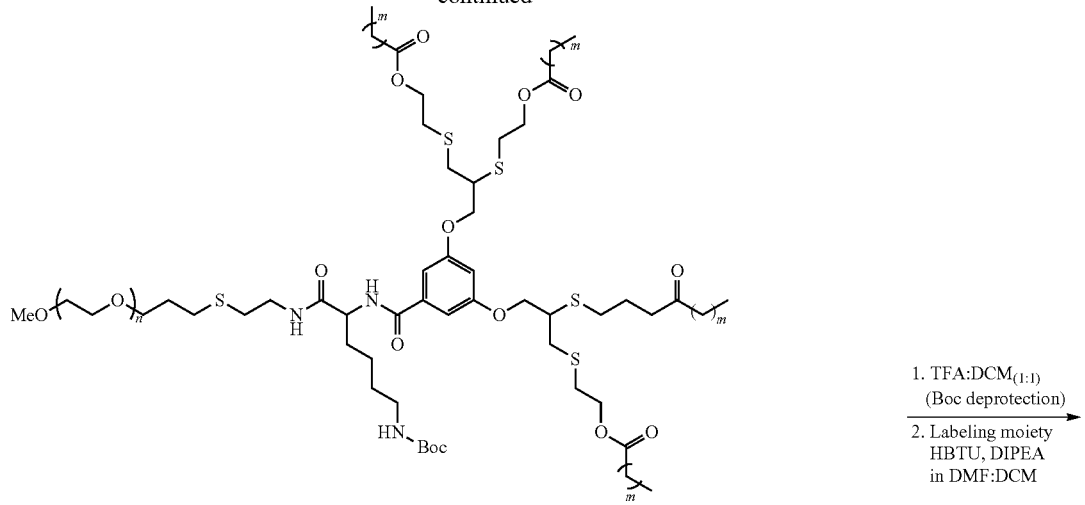

PEG-Lys(Boc)-dendron-(Aliphatic)$_4$
(Hybrid 11)
m = 1-12
Hybrid 11a: m = 6
Hybrid 11b: m = 9

1. TFA:DCM$_{(1:1)}$
(Boc deprotection)
2. Labeling moiety
HBTU, DIPEA
in DMF:DCM

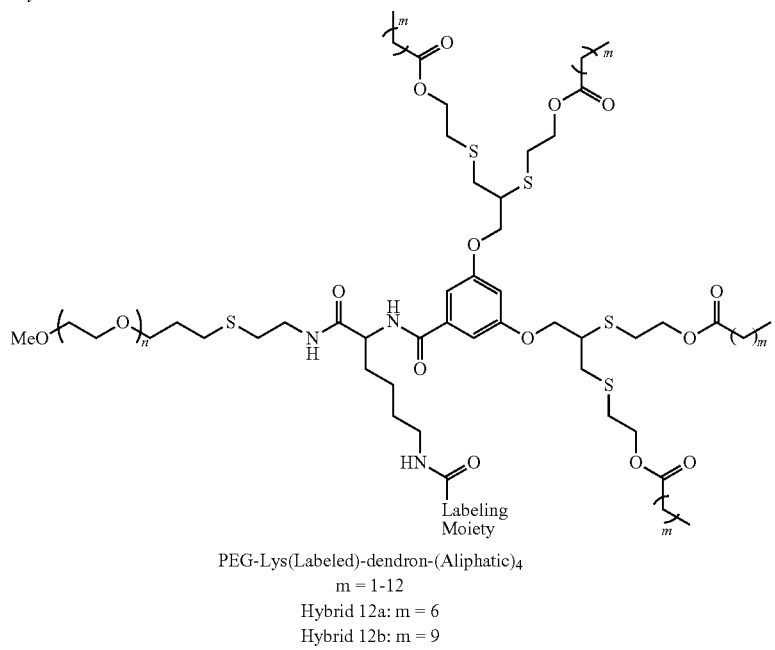

PEG-Lys(Labeled)-dendron-(Aliphatic)$_4$
m = 1-12
Hybrid 12a: m = 6
Hybrid 12b: m = 9

In some specific embodiments of Scheme 8, m=6 (i.e., the carboxylic acid is octanoic acid), and the product is hybrid 12a. In other specific embodiments of Scheme 8, m=9 (i.e., the carboxylic acid is undecanoic acid), and the product is hybrid 12b.

General Procedure for MeO-PEG$_{5kDa}$-Lys(Boc)-dendron-(Aliphatic)$_4$:

MeO-PEG$_{5kDa}$-Lys(Boc)-dendron-(OH)$_4$[1] (5) was dissolved in DCM (1 mL, per 0.1 g). Aliphatic acid (20 eq.) were added. The flask was cooled to 0° C. followed by the addition of DCC (20 eq.) and DMAP (0.1 eq.) dissolved in DCM (1 mL). The reaction was stirred for 1 hour at room temperature. The crude mixture was filtered and the organic solution was evaporated to dryness. The residue was re-dissolved in DCM (5 mL per 1 g) and the product was precipitated by the drop wise addition of Ether (50 mL per 1 g). The precipitate underwent centrifugation and was separated from the organic solvent. The precipitate was collected and residual of solvents were evaporated under vacuum. The residue was dissolved in MeOH and loaded on a MeOH based LH20 SEC column. The fractions that contained the product were unified and the MeOH was evaporated in vacuum to yield an oily residue. In order to facilitate the removal of residual MeOH and solidification of the product, the oily residue was re-dissolved in DCM (1 mL) followed by addition of Hexane (3 mL). DCM and Hexane were evaporated to dryness and the obtained solid was dried under high vacuum.

Hybrid 11a MeO-PEG$_{5kDa}$-Lys(Boc)-dendron-(Oct)$_4$: 245 mg (0.042 mmol) of MeO-PEG$_{5kDa}$-Lys(Boc)-dendron-(OH)$_4$ (5) and Octanoic acid (0.830 mmol, 20 eq.) were reacted according to the general procedure and the product was obtained as an off-whit solid (240 mg, 90% yield).

¹H NMR (400 MHz, Chloroform-d): δ 7.10-6.86 (m, 3H, —CH—NH—CO—Ar—+Ar—H), 6.73-6.49 (m, 2H, CH₂—NH—CO—CH—+Ar—H), 4.66 (m, 1H, —NH-Boc), 4.53 (q, J=7.5 Hz, 1H, —CO—CH—NH—), 4.31-4.06 (m, 12H, —CH₂—O—CO—+—Ar—O—CH₂—), 3.88-3.39 (m, 514H, PEG backbone), 3.34 (s, 3H, CH₃—O-PEG), 3.16 (q, J=6.1 Hz, 2H, —CH—S—), 3.06 (m, 2H, Boc-NH—CH₂—), 3.01-2.82 (m, 8H, —CH—CH₂—S—+—CH—S—CH₂—), 2.81-2.71 (m, 4H, —CH—CH₂—S—CH₂—), 2.59 (dt, J=22.0, 7.0 Hz, 3H, —CH₂—S—CH₂—), 2.27 (td, J=7.5, 1.9 Hz, 8H, —O—CO—CH₂—CH₂—(CH₂)₄—CH₃), 2.02-1.65 (m, 4H, —O—CH₂—CH₂—CH₂—S—+Boc-NH—CH₂—CH₂—CH₂—CH₂—CH—), 1.59 (m, 10H, —O—CO—CH₂—CH₂—(CH₂)₄—CH₃+Boc-NH—CH₂—CH₂—CH₂—CH₂—CH—), 1.37 (m, 11H, Boc-NH—CH₂—CH₂—CH₂—CH₂—CH+Boc), 1.31-1.11 (m, 34H, —O—CO—CH₂—CH₂—(CH₂)₄—CH₃), 0.91-0.73 (m, 12H, —O—CO—CH₂—CH₂—(CH₂)₄—CH₃). ¹³C NMR (101 MHz, CDCl3): δ 173.1, 171.0, 166.3, 159.1, 155.7, 149.1, 135.6, 105.8, 104.3, 71.5, 70.5, 69.8, 69.7, 69.3, 68.9, 62.9, 62.6, 58.5, 53.0, 45.1, 39.6, 38.2, 34.4, 33.7, 31.6, 31.2, 31.1, 29.9, 29.2, 29.1, 28.6, 28.5, 28.4, 27.9, 27.9, 24.4, 22.4, 22.1, 13.6.

Hybrid 11b MeO-PEG$_{5kDa}$-Lys(Boc)-dendron-(Und)₄: 267 mg (0.045 mmol) of MeO-PEG$_{5kDa}$-Lys(Boc)-dendron-(OH)₄ (5) and Undecanoic acid (0.910 mmol, 20 eq.) were reacted according to the general procedure and the product was obtained as an off-white solid (268 mg, 90% yield).

¹H NMR (400 MHz, Chloroform-d): δ 7.06-6.90 (m, 3H, —CH—NH—CO—Ar—+Ar—H), 6.72-6.50 (m, 2H, CH₂—NH—CO—CH—+Ar—H), 4.66 (m, 1H, —NH-Boc), 4.53 (q, J=7.6 Hz, 1H, —CO—CH—NH—), 4.33-4.06 (m, 12H, —CH₂—O—CO—+—Ar—O—CH₂—), 3.77-3.44 (m, 498H, PEG backbone), 3.34 (s, 3H, CH₃—O-PEG), 3.17 (q, J=5.9, 2H, —CH—S—), 3.06 (q, J=6.7 Hz, 2H, Boc-NH—CH₂—), 3.03-2.80 (m, 8H, —CH—CH₂—S—+—CH—S—CH₂—), 2.82-2.71 (m, 4H, —CH—CH₂—S—CH₂—), 2.59 (dt, J=21.9, 7.0 Hz, 4H, —CH₂—S—CH₂—), 2.27 (td, J=7.5, 2.0 Hz, 8H, —O—CO—CH₂—CH₂—(CH₂)₇—CH₃), 2.03-1.65 (m, 4H, —O—CH₂—CH₂—CH₂—S—+Boc-NH—CH₂—CH₂—CH₂—CH₂—CH—), 1.64-1.44 (m, 10H, —O—CO—CH₂—CH₂—(CH₂)₇—CH₃+Boc-NH—CH₂—CH₂—CH₂—CH₂—CH—), 1.38 (m, 11H, Boc-NH—CH₂—CH₂—CH₂—CH₂—CH+Boc), 1.22 (m, 59H, —O—CO—CH₂—CH₂—(CH₂)₇—CH₃), 0.84 (t, J=6.9 Hz, 12H, —O—CO—CH₂—CH₂—(CH₂)₇—CH₃). ¹³C NMR (101 MHz, CDCl₃): δ 173.1, 171.0, 166.3, 159.1, 155.6, 135.6, 105.8, 104.3, 71.4, 70.3, 69.87, 69.7, 69.3, 68.9, 62.9, 62.6, 58.5, 53.0, 45.0, 39.6, 38.2, 34.4, 33.7, 31.6, 31.4, 31.1, 31.0, 29.9, 29.2, 29.1, 29.0, 28.9, 28.8, 28.7, 28.6, 28.0, 27.8, 24.4, 22.4, 22.2, 13.6.

General procedure for MeO-PEG$_{5kDa}$-Lys(Labeled)-dendron-(Aliphatic)₄:

MeO-PEG$_{5kDa}$-Lys(Boc)-dendron-(Aliphatic)₄ (11a or 11b) was dissolved in DCM (1 mL) and TFA was added (1 mL). After 30 minutes the solution was evaporated to dryness and dried in vacuum. The labeling moiety with a carboxylic acid functional group (2 eq.) and HBTU (2 eq.) were dissolved in DCM: DMF 1:1 (1 mL) followed by addition of DIPEA (20 eq.). The solution was added to the deprotected hybrid (MeO-PEG$_{5kDa}$-Lys(NH₂)-dendron-(Aliphatic)₄) dissolved in DCM (1 mL, per 0.1 g). The reaction was stirred for 1 hour in room temperature. The crude mixture was concentrated under vacuum and loaded on a MeOH based LH20 SEC column. The fractions that contained the product were unified and the DCM and MeOH were evaporated in vacuum to yield an oily residue. In order to facilitate the removal of residual MeOH and solidification of the product, the oily residue was re-dissolved in DCM (1 mL) followed by addition of Hexane (3 mL). DCM and Hexane were evaporated to dryness and the obtained solid was dried under high vacuum.

Scheme 9. Procedure for preparation of Coumarin labeled aliphatic hybrids - 13a, 13b.

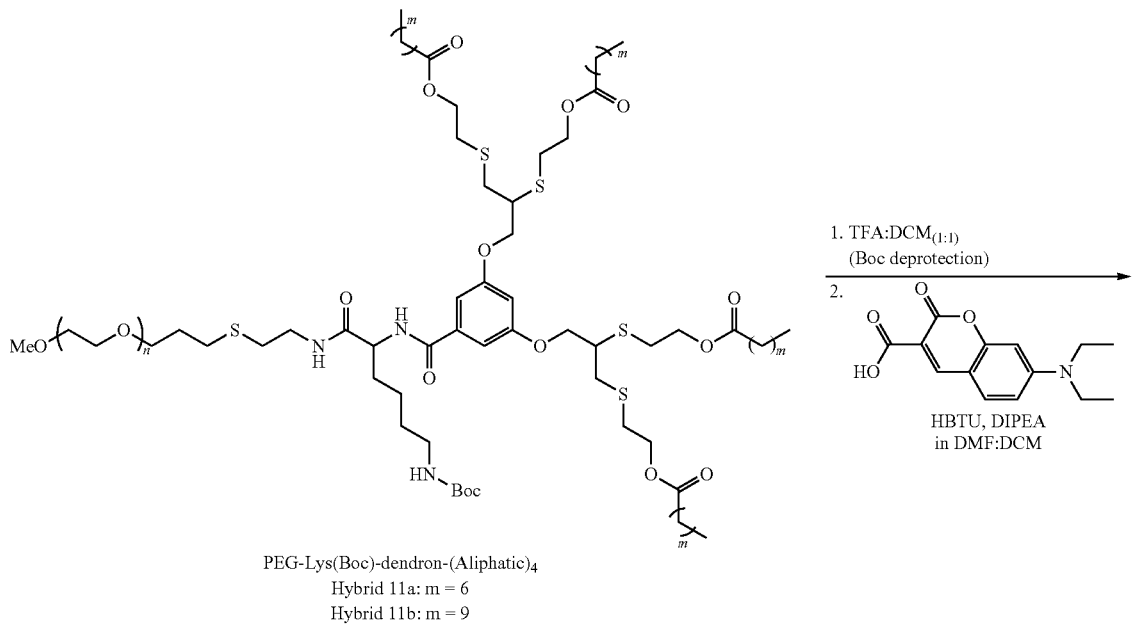

PEG-Lys(Boc)-dendron-(Aliphatic)₄
Hybrid 11a: m = 6
Hybrid 11b: m = 9

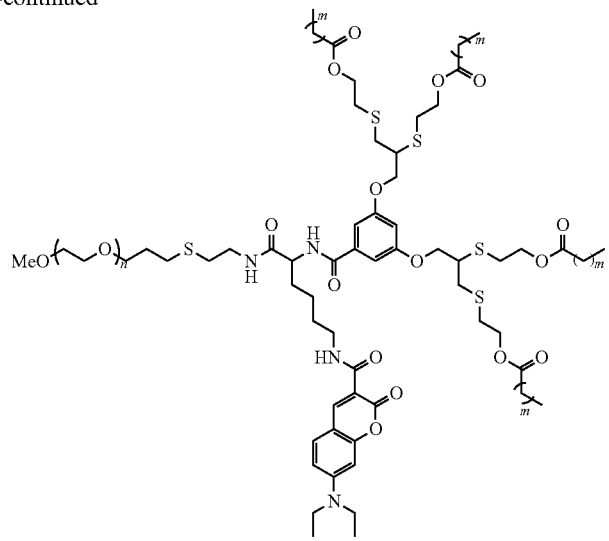

PEG-Lys(Coumarin)-dendron-(Aliphatic)$_4$
Hybrid 13a: m = 6
Hybrid 13b: m = 9

Hybrid 13a MeO-PEG$_{5kDa}$-Lys(Coumarin)-dendron-(Oct)$_4$: 104 mg (0.016 mmol) of MeO-PEG$_{5kDa}$-Lys(Boc)-dendron-(O4. (11a) were deprotected to yield MeO-PEG$_{5kDa}$-Lys(NH$_2$)-dendron-(Oct)$_4$ that were reacted with 7-(diethylamino)-3-carboxy coumarin (0.032 mmol, 2 eq.) according to the general procedure and the product was obtained as a yellow solid (98 mg, 92% yield).

$^1$H NMR (400 MHz, Chloroform-d) δ 8.82 (m, 1H, —CH$_2$—CH$_2$—NH—O—), 8.52 (s, 1H, Ar—H), 7.35 (d, J=9.0 Hz, 1H, Ar—H), 7.19 (d, J=6.8 Hz, 1H, —CH—NH—CO—Ar—), 7.02 (m, 2H, Ar—H), 6.78 (m, 1H, —CH$_2$—NH—CO—CH—), 6.66-6.55 (m, 2H, Ar—H), 6.44 (s, 1H, Ar—H), 4.51 (m, 1H, —CO—CH—NH—), 4.35-4.06 (m, 12H, —CH$_2$—O—CO—+—Ar—O—CH$_2$—), 3.76-3.39 (m, 535H, PEG backbone), 3.33 (s, 3H, CH$_3$—O-PEG), 3.16 (t, J=5.9 Hz, 2H, —CH—S—), 3.03-2.70 (m, 12H, —CH—CH$_2$—S—CH$_2$—+—CH—S—CH$_2$—), 2.58 (dt, J=25.5, 6.9 Hz, 3H, —CH$_2$—S—CH$_2$—), 2.26 (t, J=7.7 Hz, 8H, —O—CO—CH$_2$—CH$_2$—(CH$_2$)$_4$—CH$_3$), 2.04-1.74 (m, 4H, —O—CH$_2$—CH$_2$—CH$_2$—S—+—NH—CH$_2$—CH$_2$—CH$_2$—CH$_2$—CH—), 1.68-1.37 (m, 12H, —O—CO—CH$_2$—CH$_2$—(CH$_2$)$_4$—CH$_3$+—NH—CH$_2$—CH$_2$—CH$_2$—CH—), 1.22 (q, J=7.0, 6.4 Hz, 44H, —O—CO—CH$_2$—CH$_2$—(CH$_2$)$_4$—CH$_3$+—N—CH$_2$—CH$_3$), 0.90-0.74 (m, 13H, —O—CO—CH$_2$—CH$_2$—(CH$_2$)$_4$—CH$_3$). $^{13}$C NMR (101 MHz, CDCl$_3$): δ 173.7, 171.7, 167.1, 163.5, 162.8, 159.5, 157.6, 152.6, 148.2, 136.3, 110.2, 108.4, 96.6, 71.8, 70.6, 69.5, 63.4, 63.1, 45.5, 45.1, 34.3, 31.7, 30.4, 29.6, 29.2, 29.0, 25.0, 22.7, 14.2, 12.6.

Hybrid 13b MeO-PEG$_{5kDa}$-Lys(Coumarin)-dendron-(Und)$_4$: 81 mg (0.012 mmol) of MeO-PEG$_{5kDa}$-Lys(Boc)-dendron-(Und)$_4$ (11a) were deprotected to yield MeO-PEG$_{5kDa}$-Lys(NH$_2$)-dendron-(Und)$_4$ that were reacted with 7-(diethylamino)-3-carboxy coumarin (0.024 mmol, 2 eq.) according to the general procedure and the product was obtained as a yellow solid (81 mg, quantitative yield).

$^1$H NMR (400 MHz, Chloroform-d): δ 8.84 (t, J=5.9 Hz, 1H, —CH$_2$—CH$_2$—NH—CO—), 8.55 (s, 1H, Ar—H), 7.37 (dt, J=9.0, 1.2 Hz, 1H, Ar—H), 7.18 (d, J=7.8 Hz, 1H, —CH—NH—CO—Ar—), 7.02 (d, J=2.3 Hz, 2H, Ar—H), 6.78 (t, J=5.7 Hz, 1H, —CH$_2$—NH—CO—CH—), 6.69-6.52 (m, 2H, Ar—H), 6.47 (d, J=2.3 Hz, 1H, Ar—H), 4.54 (t, J=6.5 Hz, 1H, —CO—CH—NH—), 4.35-4.08 (m, 11H, —CH$_2$—O—CO—+—Ar—O—CH$_2$—), 3.79-3.44 (m, 522H, PEG backbone), 3.35 (s, 3H, CH$_3$—O-PEG), 3.23-3.13 (m, 2H, —CH—S—), 3.03-2.81 (m, 8H, —CH—CH$_2$—S—+—CH—S—CH$_2$—), 2.80-2.72 (m, 4H, —CH—CH$_2$—S—CH$_2$—), 2.61 (dt, J=26.0, 7.0 Hz, 4H, —CH$_2$—S—CH$_2$—), 2.37-2.24 (m, 9H, —O—CO—CH$_2$—CH$_2$—(CH$_2$)$_7$—CH$_3$), 2.06-1.76 (m, 4H, —O—CH$_2$—CH$_2$—CH$_2$—S—+—NH—CH$_2$—CH$_2$—CH$_2$—CH$_2$—CH—), 1.70-1.42 (m, 11H, —O—CO—CH$_2$—CH$_2$—(CH$_2$)$_7$—CH$_3$+—NH—CH$_2$—CH$_2$—CH$_2$—CH—), 1.23 (q, J=4.3, 3.3 Hz, 63H, —O—CO—CH$_2$—CH$_2$—(CH$_2$)$_7$—CH$_3$+—N—CH$_2$—CH$_3$), 0.85 (t, J=6.9 Hz, 12H, —O—CO—CH$_2$—CH$_2$—(CH$_2$)$_7$—CH$_3$). $^{13}$C NMR (101 MHz, CDCl$_3$): δ 173.1, 171.7, 171.1, 166.5, 162.9, 162.2, 159.0, 157.1, 152.0, 147.5, 135.8, 130.6, 129.2, 109.5, 107.9, 105.9, 104.5, 96.1, 81.6, 71.5, 70.1, 69.3, 69.0, 68.8, 62.9, 62.6, 58.5, 53.2, 50.5, 49.1, 45.1, 44.6, 38.2, 34.4, 33.7, 31.4, 31.1, 29.9, 29.2, 29.1, 29.0, 28.9, 28.7, 27.8, 24.4, 22.6, 22.2, 13.6, 12.0, 0.5.

Scheme 10. Procedure for preparation of Cy5 labeled aliphatic hybrid 14a.

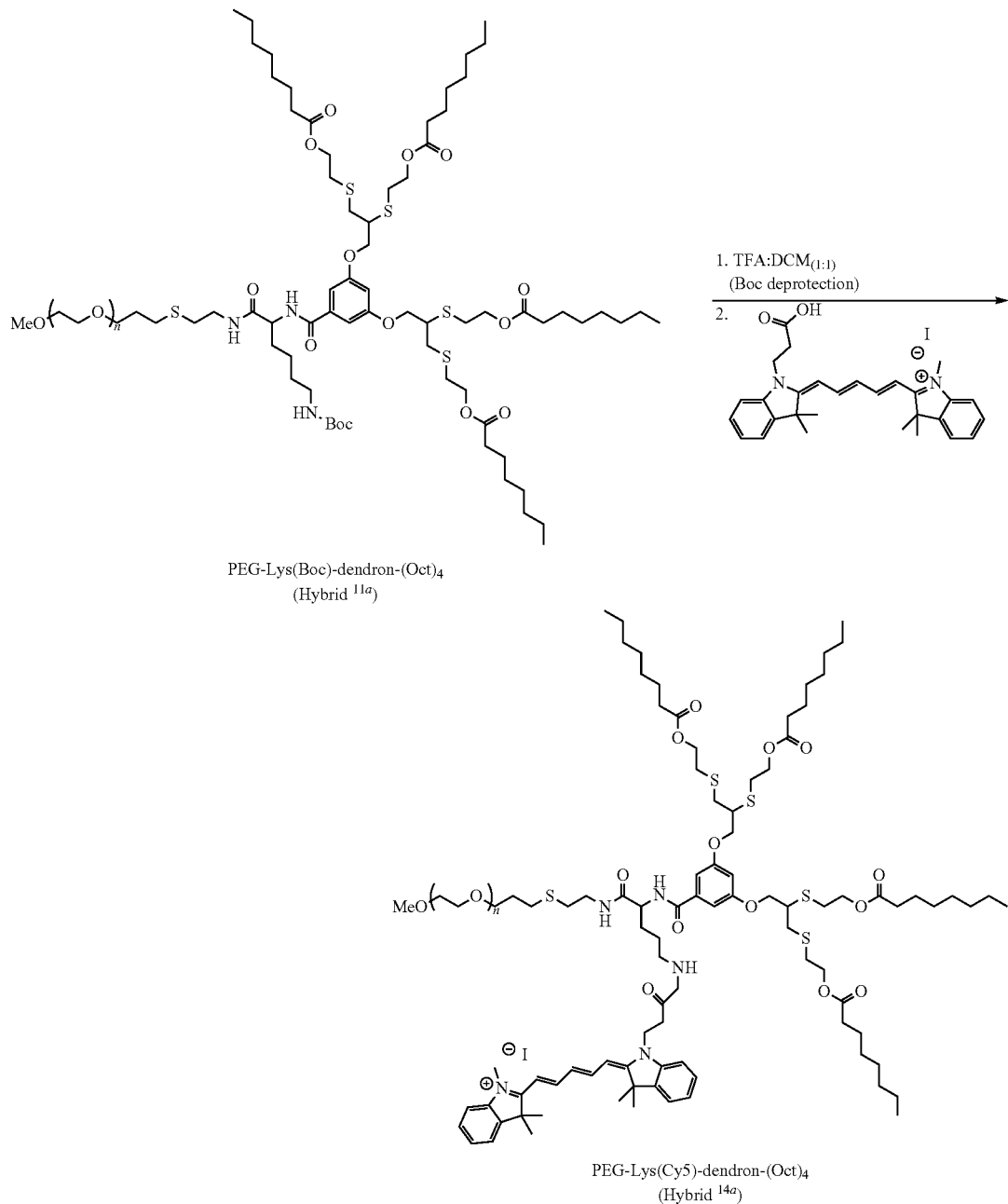

Hybrid 14a MeO-PEG$_{5kDa}$-Lys(Cy5)-dendron-(Oct)$_4$: 150 mg (0.024 mmol) of MeO-PEG$_{5kDa}$-Lys(Boc)-dendron-(Oct)$_4$ (11a) were deprotected to yield MeO-PEG$_{5kDa}$-Lys(NH$_2$)-dendron-(Oct)$_4$ that were reactled with carboxylic acid Cy5 acid (0.048 mmol, 2 eq.) according to the general procedure and the product was obtained as a blue solid (160 mg, quantitative yield).

$^1$H NMR (400 MHz, Chloroform-d) δ 8.59 (m, 1H, —CH$_2$—CO—NH—CH$_2$—), 8.05 (m, 1H, —CH—NH—CO—Ar—+—CH$_2$—NH—CO—CH—), 7.76 (dt, J=26.3, 13.0 Hz, 2H, Ar—H), 7.41-7.16 (m, 8H, Ar—H), 7.14 (d, J=2.3 Hz, 2H, Ar—H), 7.09-6.96 (m, 1H, —C—CH—CH—), 6.65-6.50 (m, 2H, —CH—CH—CH—CH—), 6.44 (d, J=13.7 Hz, 1H, C—CH—CH—), 6.07 (d, J=13.4 Hz, 1H, C—CH—CH—), 4.72-4.51 (m, 1H, —CO—CH—NH—), 4.38 (t, J=7.0 Hz, 1H, —N—CH$_2$—CH$_2$—CO—), 4.30-4.07 (m, 12H, —CH$_2$—O—CO—+—Ar—O—CH$_2$—), 3.79-3.44 (m, 522H, PEG backbone), 3.35 (s, 4H, CH$_3$—O-PEG), 3.17 (m, 3H, —CH—S—), 3.03-2.69 (m, 14H, —CH—CH$_2$—S—CH$_2$—+—CH—S—CH$_2$—), 2.58 (dt, J=23.2, 7.6 Hz, 3H, —CH$_2$—S—CH$_2$—), 2.06-1.73 (m, 4H, —O—CH$_2$—CH$_2$—CH$_2$—S—+—NH—CH$_2$—CH$_2$—CH$_2$—CH$_2$—CH—), 1.66 (d, J=3.9 Hz, 9H, —C—CH$_3$), 1.58 (t, J=7.2 Hz, 12H, —O—CO—CH$_2$—CH$_2$—(CH$_2$)$_4$—CH$_3$+—NH—CH$_2$—CH$_2$—CH$_2$—CH$_2$—CH—), 1.34-1.15 (m, 39H, —O—CO—CH$_2$—CH$_2$—(CH$_2$)$_4$—CH$_3$), 0.91-0.78 (m, 14H, —O—CO—CH$_2$—CH$_2$—(CH$_2$)$_4$—CH$_3$).

$^{13}$C NMR (101 MHz, CDCl$_3$): δ 173.4, 173.0, 172.1, 171.7, 168.9, 166.1, 158.9, 153.0, 151.6, 142.3, 141.1, 140.0, 136.1, 128.4, 128.2, 125.7, 125.2, 124.3, 121.5, 121.5, 111.0, 109.6, 105.9, 104.4, 102.4, 71.4, 70.6, 70.3, 70.0, 69.6, 69.3, 69.1, 68.9, 62.8, 62.6, 58.5, 53.9, 49.0, 45.1, 41.3, 38.8, 38.1, 34.4, 33.7, 31.1, 31.0, 30.4, 29.8, 29.1, 28.5, 28.4, 27.8, 27.6, 27.5, 27.4, 27.3, 24.4, 22.5, 22.1, 22.0, 13.5.

A corresponding compound of formula 14b comprising an ester based on undecanoic acid was prepared following the procedure for compound 14a.

(0.04 mmol, 2 eq.) according to the general procedure and the product was obtained as an orange solid (131 mg, quantitative yield).

$^1$H NMR (400 MHz, Chloroform-d) δ 7.98-7.74 (m, 4H, Ar—H), 7.49-7.31 (m, 3H, Ar—H), 7.11 (d, J=7.0 Hz, 1H, —CH—NH—CO—Ar—), 7.03-6.89 (m, 4H, Ar—H), 6.86-6.62 (m, 2H, —CH$_2$—NH—CO—CH—), 6.57 (t, J=2.2 Hz, 1H, Ar—H), 4.56-4.31 (m, 3H, —CO—CH—NH—+—O—CH$_2$—CO—), 4.26-4.09 (m, 12H, —CH$_2$—O—CO—+—

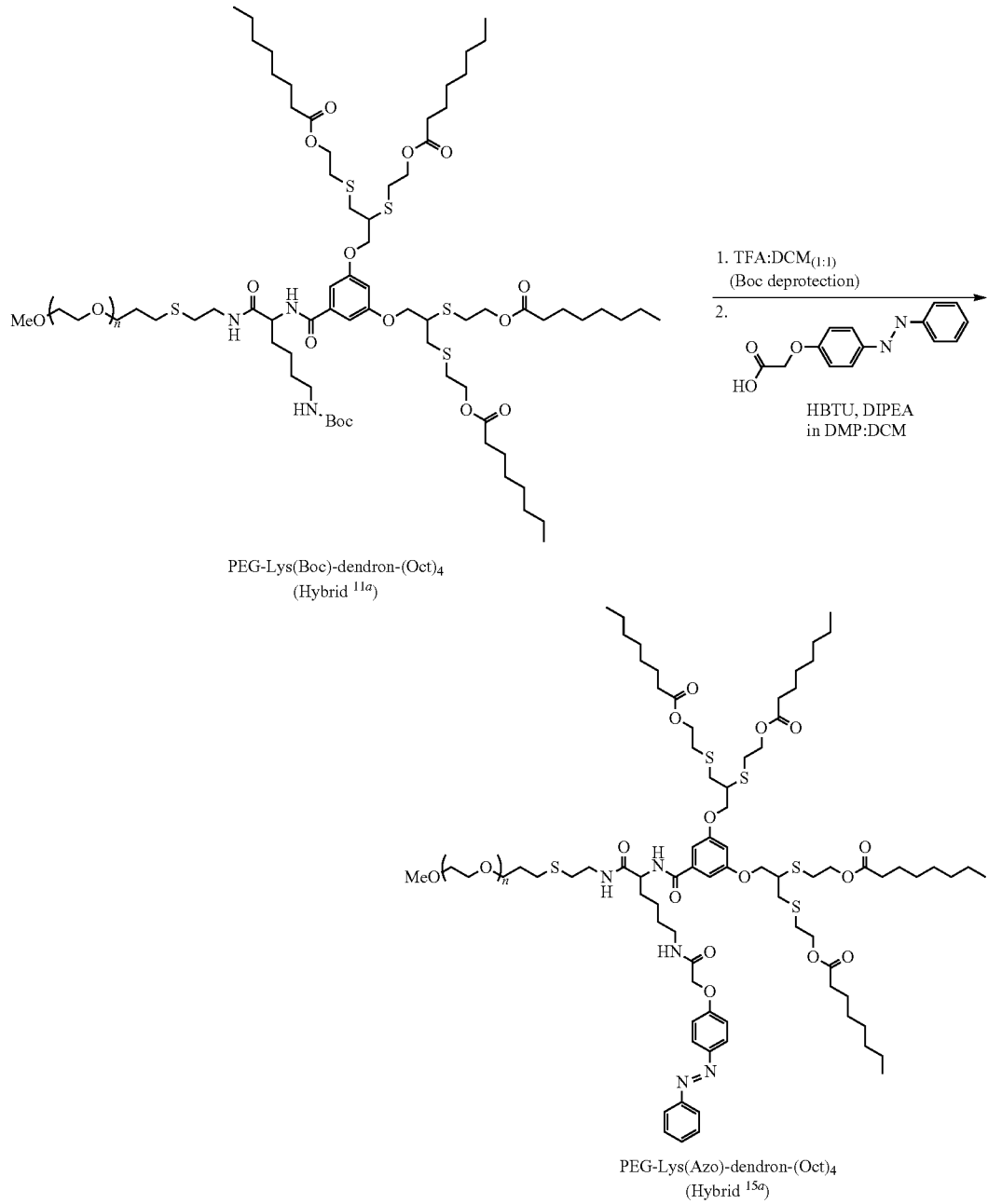

Scheme 11. Procedure for preparation of labeled aliphatic hybrid 15a.

PEG-Lys(Boc)-dendron-(Oct)$_4$
(Hybrid $^{11a}$)

1. TFA:DCM$_{(1:1)}$ (Boc deprotection)
2. HBTU, DIPEA in DMP:DCM

PEG-Lys(Azo)-dendron-(Oct)$_4$
(Hybrid $^{15a}$)

Hybrid 15a MeO-PEG$_{5kDa}$-Lys(Azo)-dendron-(Oct)$_4$: 130 mg (0.020 mmol) of MeO-PEG$_{5kDa}$-Lys(Boc)-dendron-(Oct)$_4$ (11a) were deprotected to yield MeO-PEG$_{5kDa}$-Lys(NH$_2$)-dendron-(Oct)$_4$ that were reacted with azo acid$^2$ Ar—O—CH$_2$—), 3.8.0-3.38 (m, 509H, PEG backbone), 3.31 (s, 6H, CH$_3$—O-PEG), 3.21-3.07 (m, 3H, —CH—S—), 3.00-2.63 (m, 13H, —CH—CH$_2$—S—CH$_2$—+ CH—S—CH$_2$—), 2.56 (dt, J=22.5, 7.0 Hz, 9H, —CH$_2$—

S—CH$_2$—), 2.32-2.13 (m, 8H, —O—CO—CH$_2$—CH$_2$—(CH$_2$)$_4$—CH$_3$), 2.02-1.69 (m, 4H, —O—CH$_2$—CH$_2$—CH$_2$—S—+—NH—CH$_2$—CH$_2$—CH$_2$—CH$_2$—CH—), 1.53 (dd, J=11.0, 4.0 Hz, 10H, —O—CO—CH$_2$—CH$_2$—(CH$_2$)$_4$—CH$_3$+—NH—CH$_2$—CH$_2$—CH$_2$—CH$_2$—CH—), 1.43-1.31 (m, 3H, —NH—CH$_2$—CH$_2$—CH$_2$—CH—), 1.31-1.08 (m, 35H, —O—CO—CH$_2$—CH$_2$—(CH$_2$)$_4$—CH$_3$), 0.80 (t, J=6.9 Hz, 12H, —O—CO—CH$_2$—CH$_2$—(CH$_2$)$_4$—CH$_3$). $^{13}$C NMR (101 MHz, CDCl$_3$): δ 173.0, 171.0, 167.5, 166.4, 159.1, 158.7, 152.1, 147.3, 135.5, 130.2, 128.5, 128.4, 124.3, 122.9, 122.2, 119.4, 114.5, 114.1, 105.8, 104.4, 71.4, 70.3, 69.8, 69.7, 69.3, 68.9, 66.9, 63.2, 62.9, 62.5, 58.5, 53.0, 45.0, 38.2, 37.7, 34.3, 33.7, 31.1, 31.0, 30.8, 29.9, 29.1, 28.6, 28.5, 28.4, 27.8, 24.4, 22.1, 13.6.

A corresponding compound of formula 15b comprising an ester based on undecanoic acid was prepared following the procedure for compound 15a.

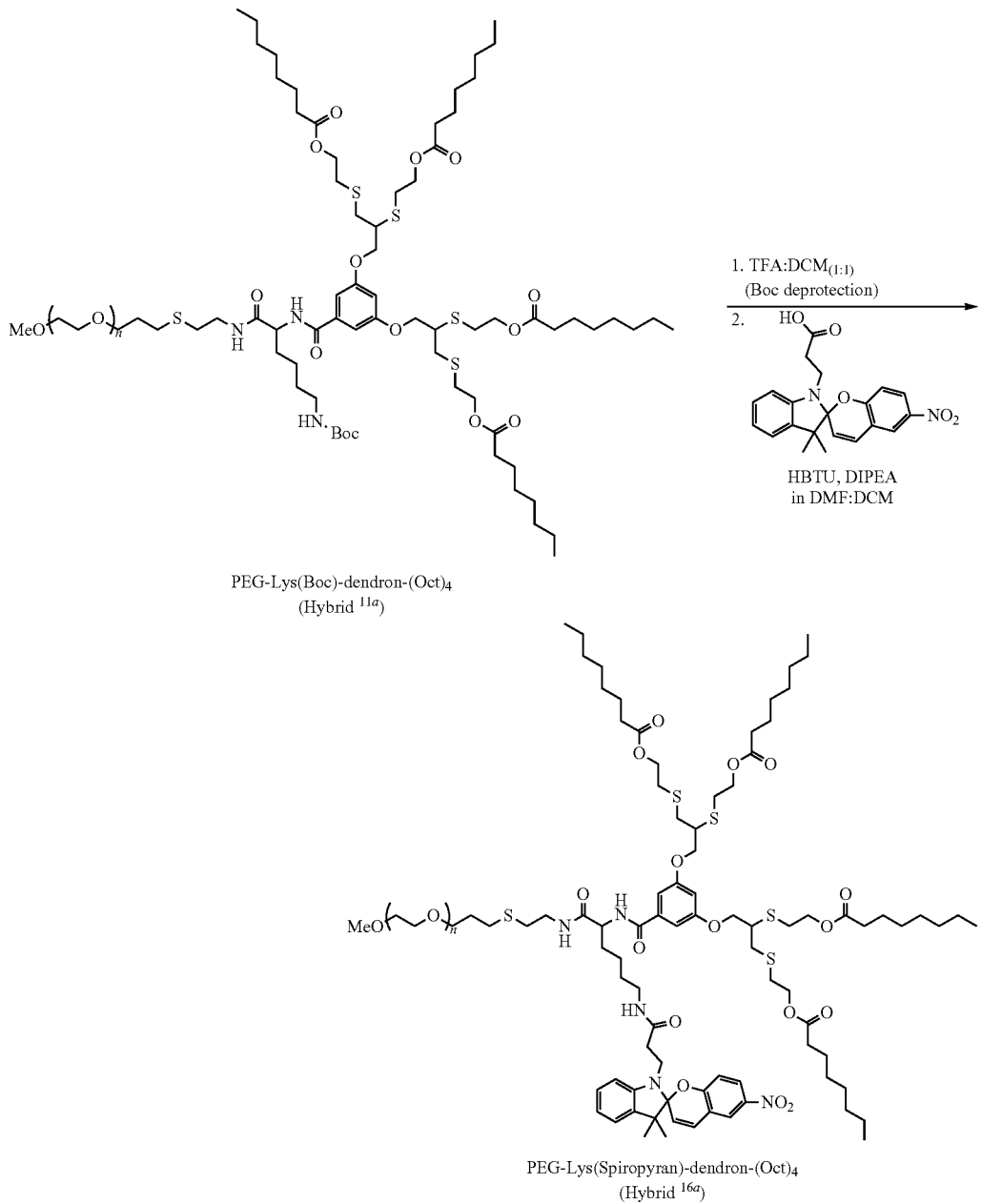

Scheme 12. Procedure for preparation of Spiropyran labeled aliphatic hybrid 16a.

Hybrid 16a MeO-PEG$_{5kDa}$-Lys(Spiropyrin)-dendron-(Oct)$_4$: 130 mg (0.020 mmol) of MeO-PEG$_{5kDa}$-Lys(Boc)-dendron-(Oct)$_4$ (11a) were deprotected to yield MeO-PEG$_{5kDa}$-Lys(NH$_2$)-dendron-(Oct)$_4$ that were reacted with azo acid (0.04 mmol, 2 eq.) according to the general procedure and the product was obtained as an orange solid (131 mg, quantitative yield).

$^1$H NMR (400 MHz, Chloroform-d) δ 8.03-7.86 (m, 2H, Ar—H), 7.20-7.10 (m, 1H, Ar—H), 7.04 (d, J=7.1 Hz, 2H, Ar—H), 6.98 (d, J=2.3 Hz, 2H, Ar—H), 6.94-6.78 (m, 2H, Ar—H+—CH—CH—), 6.69 (d, J=7.9 Hz, 1H, Ar—H), 6.63-6.57 (m, 2H, Ar—H+—CH$_2$—NH—CO—CH—), 5.80 (dd, J=10.5, 2.3 Hz, 1H, —CH—CH—), 4.49 (d, J=7.5 Hz, 1H, —CO—CH—NH—), 4.32-4.11 (m, 14H, —CH₂—O—CO—+—Ar—O—CH₂—), 3.81-3.39 (m, 563H, PEG backbone), 3.35 (s, 5H, CH₃—O-PEG), 3.16 (q, J=6.0 Hz, 8H, —CH—S—+—NH—CH₂—CH₂—CH₂—CH₂—CH—), 3.03-2.71 (m, 18H, —CH—CH₂—S—CH₂—+—CH—S—CH₂—), 2.59 (dt, J=22.6, 7.0 Hz, 5H, —CH₂—S—CH₂—), 2.52-2.42 (m, 2H, —N—CH₂—CH₂—CO—), 2.39-2.16 (m, 19H, —O—CO—CH₂—CH₂—(CH₂)₄—CH₃), 2.04-1.64 (m, 4H, —O—CH₂—CH₂—CH₂—S—+—NH—CH₂—CH₂—CH₂—CH₂—CH—), 1.57 (d, J=6.9 Hz, 8H, —O—CO—CH₂—CH₂—(CH₂)₄—CH₃), 1.44 (d, J=6.7 Hz, 2H, —NH—CH₂—CH₂—CH₂—CH₂—CH—), 1.35-1.14 (m, 40H, —O—CO—CH₂—CH₂—(CH₂)₄—CH₃+—NH—CH₂—CH₂—CH₂—CH₂—CH—+—CH—CH₃), 1.10 (s, 3H, —CH—CH₃), 0.93-0.75 (m, 12H, —O—CO—CH₂—CH₂—(CH₂)₄—CH₃). $^{13}$C NMR (101 MHz, CDCl₃): δ 173.1, 171.0, 166.4, 159.1, 135.5, 127.9, 127.3, 125.3, 122.3, 121.3, 119.2, 114.9, 106.3, 105.8, 71.5, 70.4, 70.1, 69.7, 69.3, 68.9, 62.9, 62.6, 58.5, 52.4, 45.1, 39.5, 38.5, 38.2, 35.2, 34.4, 33.7, 31.2, 31.1, 29.9, 29.2, 28.6, 28.4, 27.8, 25.3, 24.4, 22.1, 19.3, 13.6.

A corresponding compound of formula 16b comprising an ester based on undecanoic acid was prepared following the procedure for compound 16a.

Example 9—Preparation of MeO-PEG$_{5kDa}$-Lys(3,5-dihydroxybenz)-dendron-(Ph)₄ Aromatic Hybrid 18

Scheme 13. Procedure for preparation of labeled aromatic hybrids - 18.

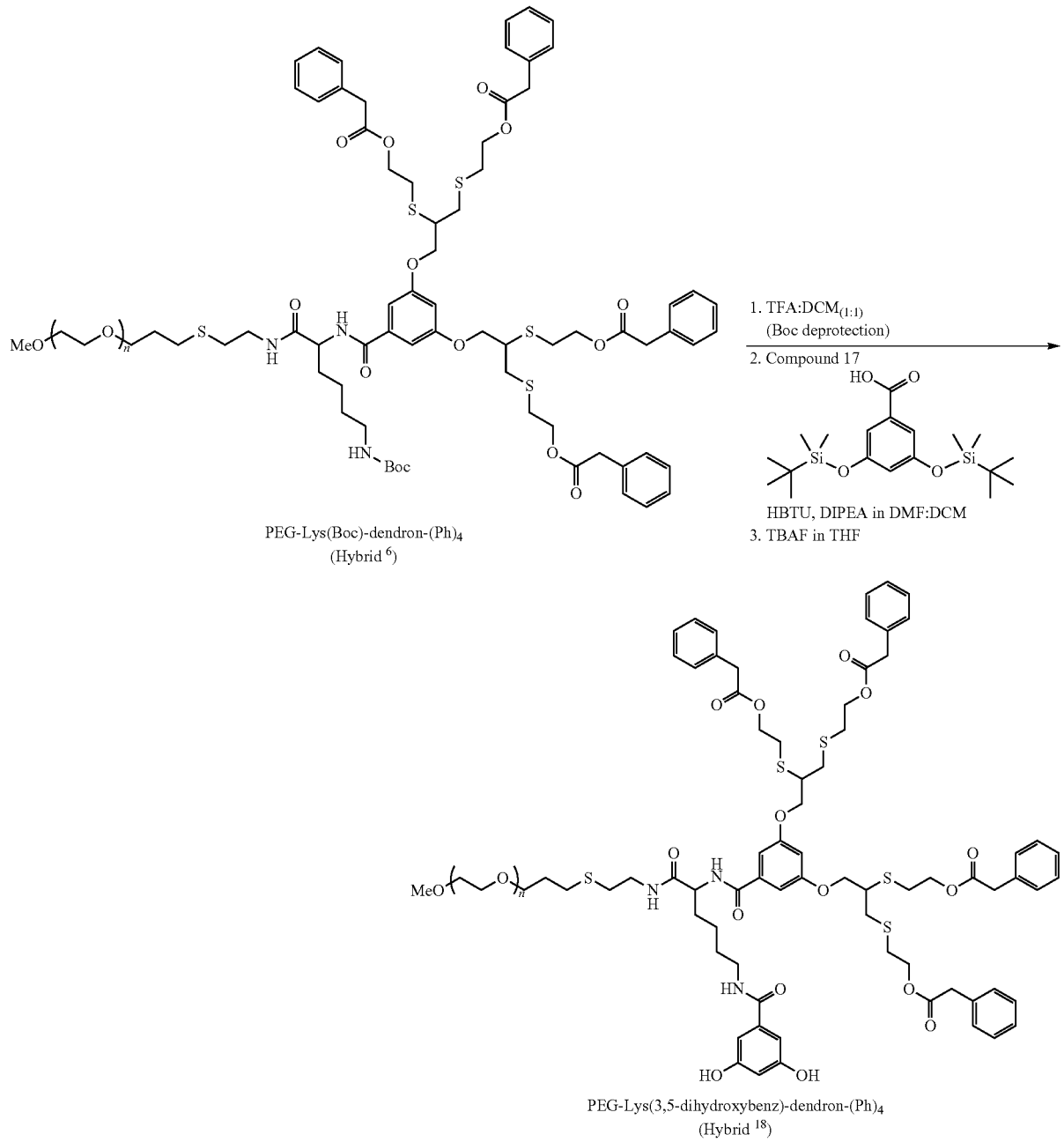

130 mg (0.020 mmol) of MeO-PEG$_{5kDa}$-Lys(Boc)-dendron-(Ph)$_4$[1,3†] (6) were dissolved in DCM (1 mL) and TFA was added (1 mL). After 30 minutes the solution was evaporated to dryness and dried in vacuum. Compound 17 (0.100 mmol, 5 eq.) and HBTU (0.100 mmol, 5 eq.) were dissolved in DCM:DMF 1:1 (1 mL) followed by addition of DIPEA (20 eq.). The solution was added to the deprotected hybrid (MeO-PEG$_{5kDa}$-Lys(NH)$_2$)-dendron-(Ph)$_4$) dissolved in DCM (1 mL, per 0.1 g). The reaction was stirred for 1 hour in room temperature. The crude mixture was concentrated under vacuum and loaded on a MeOH based LH20 SEC column. The fractions that contained the product were unified and the DCM and MeOH were evaporated in vacuum to yield an oily residue. The oily product was re-dissolved in THF (1 mL, per 0.1 g) and tetra-n-butylammonium fluoride (TBAF) was added (0.06 mmol, 3 eq.). After 30 minutes the solution was concentrated under vacuum and loaded on a MeOH based LH20 SEC column. The fractions that contained the product were unified and the DCM and MeOH were evaporated in vacuum to yield an oily residue. In order to facilitate the removal of residual MeOH and solidification of the product, the oily residue was re-dissolved in DCM (1 mL) followed by addition of Hexane (3 mL). DCM and Hexane were evaporated to dryness and the obtained off-white solid (compound 18) was dried under high vacuum (110 mg, 86% yield).

$^1$H NMR (400 MHz, Chloroform-d) δ 8.05 (s, 1H, OH), 7.34-7.17 (m, 25H, Ar—H), 7.14 (d, J=5.4 Hz, 1H, —CH—NH—CO—Ar—), 7.00 (m, 3H, Ar—H+—NH—CO—Ar), 6.89 (m, 1H, —CH$_2$—NH—CO—CH—), 6.77 (d, J=2.2 Hz, 2H, Ar—H), 6.60-6.43 (m, 2H, Ar—H), 4.57 (d, J=6.4 Hz, 1H, —CO—CH—NH—), 4.33-3.99 (m, 13H, —CH$_2$—O—CO—+—Ar—O—CH$_2$—), 3.87-3.42 (m, 597H, PEG backbone), 3.35 (s, 6H, CH$_3$—O-PEG), 3.10 (t, J=5.7 Hz, 2H, —CH—S—), 2.99-2.65 (m, 14H, —CH—CH$_2$—S—CH$_2$—+—CH—S—CH$_2$—), 2.55 (dt, J=22.2, 7.0 Hz, 8H, —CH$_2$—S—CH$_2$—), 2.04-1.68 (m, 4H, —O—CH$_2$—CH$_2$—CH$_2$—S—+—NH—CH$_2$—CH$_2$—CH$_2$—CH$_2$—CH—), 1.62-1.39 (m, 4H, —NH—CH$_2$—CH$_2$—CH$_2$—CH$_2$—CH—).

Example 10—Fluorinated Hybrids as $^{19}$F-magnetic Resonance Probes

Hybrid 20 (Scheme 14) was chosen as model compounds that can be activated by Porcine Liver Esterase (PLE).[16] 4-(Trifluoromethyl)phenylacetic acid was chosen as labeling group as it contains three equivalent fluorine atoms and a carboxylic acid that could be easily used for both esterification or amidation based labeling steps, as desired. The hybrid was synthesized directly on the PEG through accelerated dendritic growth approach[17] using amidation and thiol-yne[18,19] chemistries to build the dendrons. The synthesized hybrid and its fully hydrolyzed derivative 20a was obtained in high yields and characterized by $^1$H-NMR, $^{13}$C-NMR, $^{19}$F-NMR, IR, GPC, HPLC and MALDI-MS) and the experimental data was found to be in good agreement with the theoretical one (see Example 17).

Scheme 14. Structure of amphiphilic hybrid 20 and its hydrolyzed derivative.

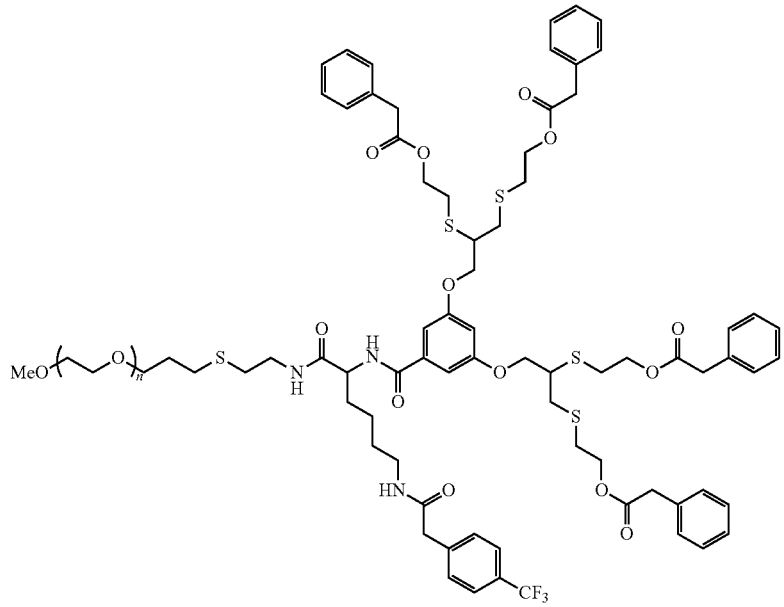

Hybrid 20

PLE

-continued

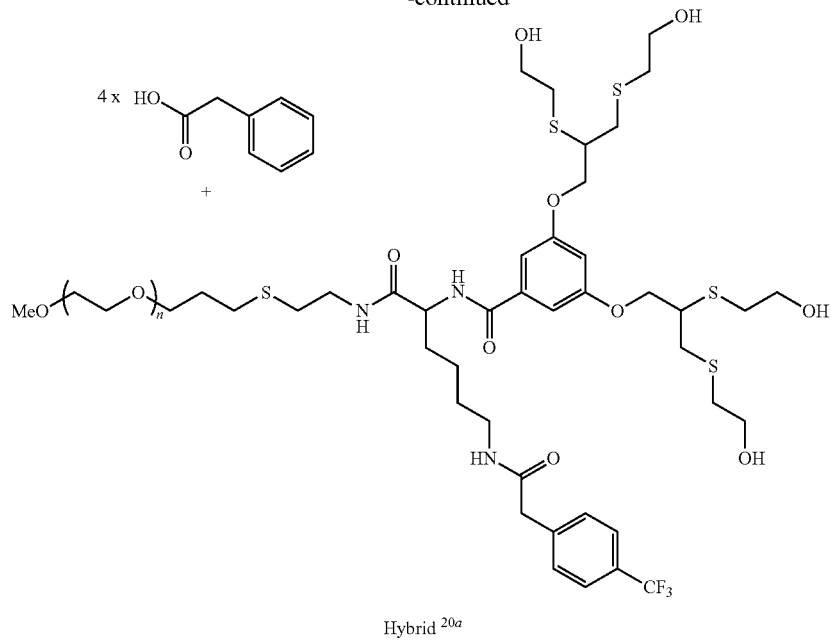

Hybrid 20a

Characterization of the Self-assembled Micelles

The critical micelle concentrations (CMC) were determined using Nile red[23] and hybrid 20 was found to have CMC values at the low micro-molar range (4+/−1 µM). Dynamic light scattering (DLS) measurements showed a diameters of 16+/−3 nm (FIG. 23), which fit micellar assemblies. The translation of the supramolecular structural changes into MR spectral responses depend on the differences in the spin-spin $T_2$ relaxation times of the labeled polymers at the assembled and disassembled state, after their enzymatic activation. Hence, once the self-assembly of both hybrids into micelles was confirmed, their $T_1$ and $T_2$ relaxation times were measured and compared them to the values of synthetically obtained hydrophilic hybrid 20a (Table 1). The hybrid showed significant increase in both $T_1$ and $T_2$ values going from the amphiphilic hybrid to the hydrophilic one.

TABLE 1

$^{19}$F-NMR relaxation times $T_1$ and $T_2$ of hybrid 20 before and after enzymatic activation. Hybrids 20a in the presence of the enzyme were used as control. (9.4 T, 376 MHz, TE = 80 ms

| Hybrid | 20 | 20 + PLE | 20a + PLE |
|---|---|---|---|
| $T_1$ (ms) | 860 +/− 90 | 1090 +/− 50 | 1090 +/− 30 |
| $T_2$ (ms) | 16 +/− 3 | 320 +/− 40 | 450 +/− 15 |

Structural and Spectral Responses

Figure 20:
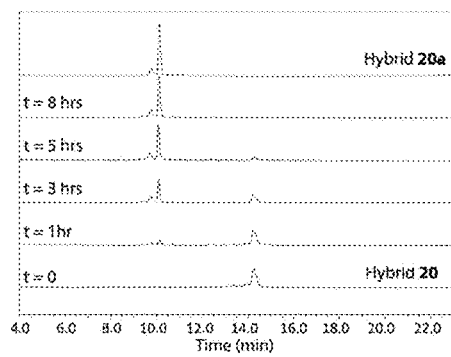
FIG. 20: Overlay of (a) HPLC chromatograms, (b) $^{19}$F-NMR spectra; and (c) kinetic data (HPLC, $^{19}$F-NMR and fluorescence) for the enzymatic-induced activation of hybrid 20.
Figure 20:
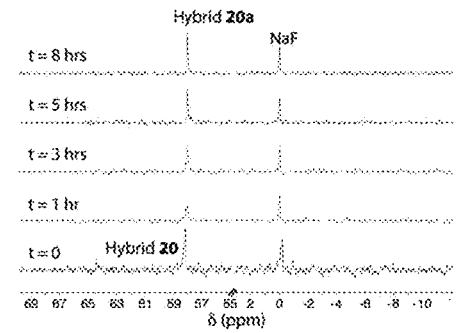
Figure 20:
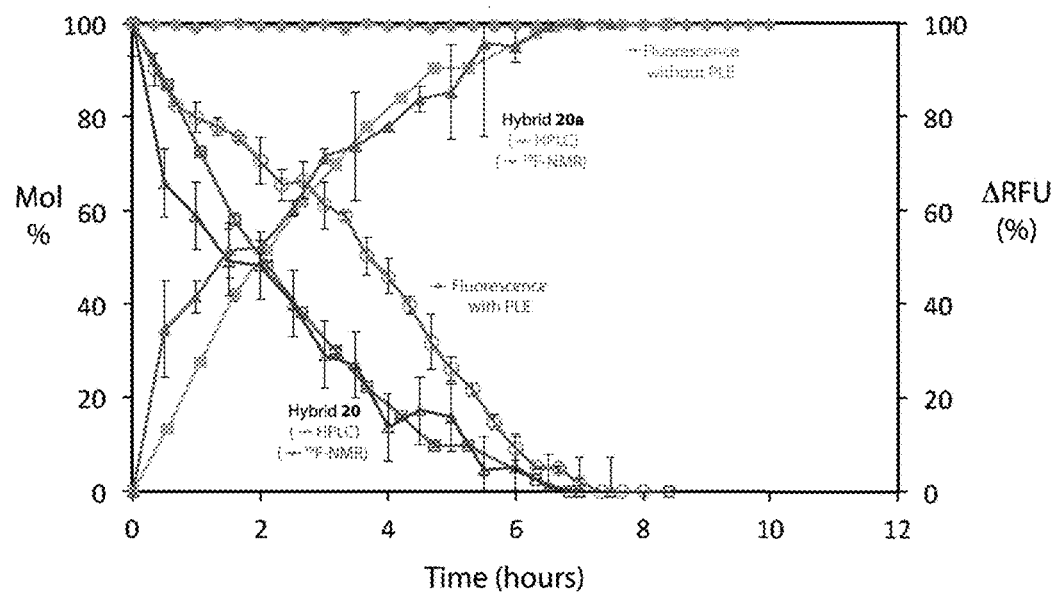

To study the structural and spectral responses of the micelles, their disassembly by DLS measurements were initially studied. The results show a clear disappearance of the larger micellar structures and formation of smaller spices with diameters of around 4-7 nm (FIG. 23), which fit well with the disassembly of the micelles into soluble hydrophilic hybrids. To get kinetic information on the disassembly process, fluorescence spectroscopy, HPLC and $^{19}$F-NMR tools were combined, using fluorine atoms at a concentration of 640 µM. The concentration of the enzyme was set to 1.1 µM. Fluorescence spectroscopy was used to study the release of encapsulated Nile red upon enzymatic activation as upon its release from the disassembling micelles into the aqueous environment its fluorescence decreases. The obtained spectra for hybrid 20 showed a decrease in the fluorescence of the released Nile red molecules in the presence of the enzyme (FIG. 23) while no change was observed in the absence of the enzyme (FIG. 24), further supporting the enzymatic-induced disassembly. Both the DLS and the fluorescence spectra gave clear indication that the micelles break down upon enzymatic activation to release their molecular cargo. However these techniques do not reveal the exact degree of activation. In order to obtain direct analysis of the polymeric components during the disassembly process, HPLC was used to follow the enzymatic degradation. The HPLC data of hybrid 20 showed direct enzymatic transformation into the corresponding hydrophilic hybrid 20a (FIG. 20a).

Next, the enzymatic activation was studied using $^{19}$F-NMR, and the results were correlated with the fluorescence and HPLC data. The acquisition parameters were set so ensure that the peaks of the labeled hydrophilic hybrid 20a were visible and could be integrated (sodium fluoride was used as internal reference and its chemical shift was set to zero). Kinetic $^{19}$F-NMR measurements clearly showed the formation of labeled hydrophilic hybrid 20a (FIGS. 20b). Excellent correlations were observed when plotting the HPLC and $^{19}$F-NMR peaks areas for both hybrids as a function of time and these results correlated well with the fluorescence data for Nile red, which is indicative of the presence of micelles (FIG. 20c).

Figure 21:
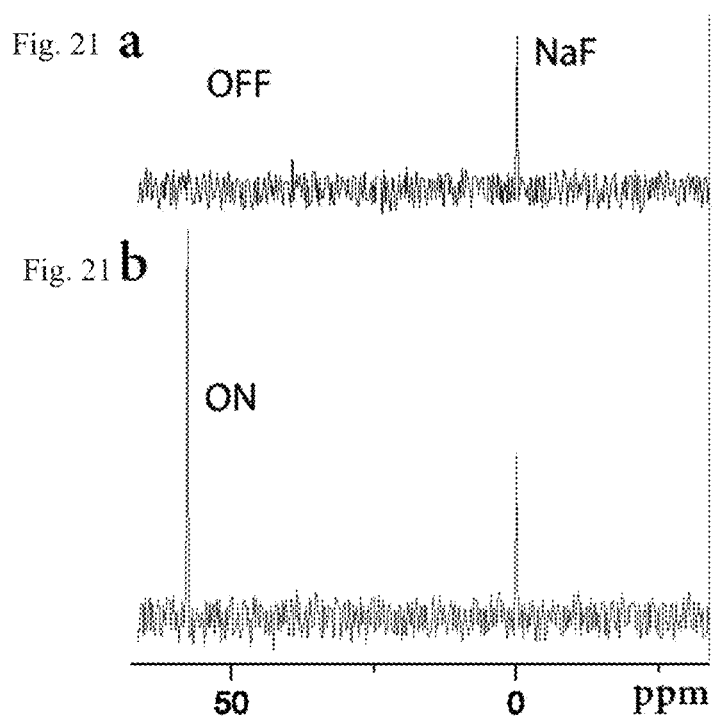
FIG. 21: $^{19}$F-NMR spectra obtained by spin-echo sequence (9.4T, 376 MHz, TE=80 ms) showing the micellar OFF states and ON states after the disassembly of hybrid 20 (a—OFF; b—ON).

After the disassembly of both types of micelles upon enzymatic activation was confirmed, their ability to show clear OFF/ON states was investigated. To do so, a spin-echo $^{19}$F-NMR sequence was used (see Example XX) to measure the spectra before the addition of the enzyme and after the disassembly was completed (FIG. 21). This sequence allows one to utilize the significant differences in $T_2$ relaxation times between the assembled and disassembled states. The obtained spectra didn't show any signal for the assembled state of hybrid 20, while the reference peak of NaF was clearly observed, indicating the OFF state of the assembled micelles (FIG. 21a). The spectra of the disassembled hybrids clearly showed the peaks correlating hydrophilic hybrid 20a, demonstrating the enzymatic-turn ON of the $^{19}$F-MR signals (FIGS. 21b).

Conclusions

In summary, demonstrated herein is the rational design of highly modular enzyme-responsive MR probes for turn-on of $^{19}$F-MR signal based on smart fluorinated amphiphilic hybrids. A molecular approach using non-cleavable labeling of the polymeric backbone was used. This design was studied by combination of DLS, Fluorescence spectroscopy, HPLC and NMR and were shown to be OFF at the assembled micellar state. Upon enzymatic activation and cleavage of the hydrophobic end-groups, the micelles disassembled and the MR signals were turned ON. The obtained results clearly prove the great potential of enzyme-responsive smart polymers to serve as an innovative and modular platform for the rational design of responsive MR probes.

Example 11—Synthesis of Fluorinated Hybrids as $^{19}$F-Magnetic Resonance Probes Hybrid 20 (MeO-PEG$_{5kDa}$-Lys(Ph-CF$_2$)-dendron-(Ph)$_4$: 160 mg (0.03 mmol) of

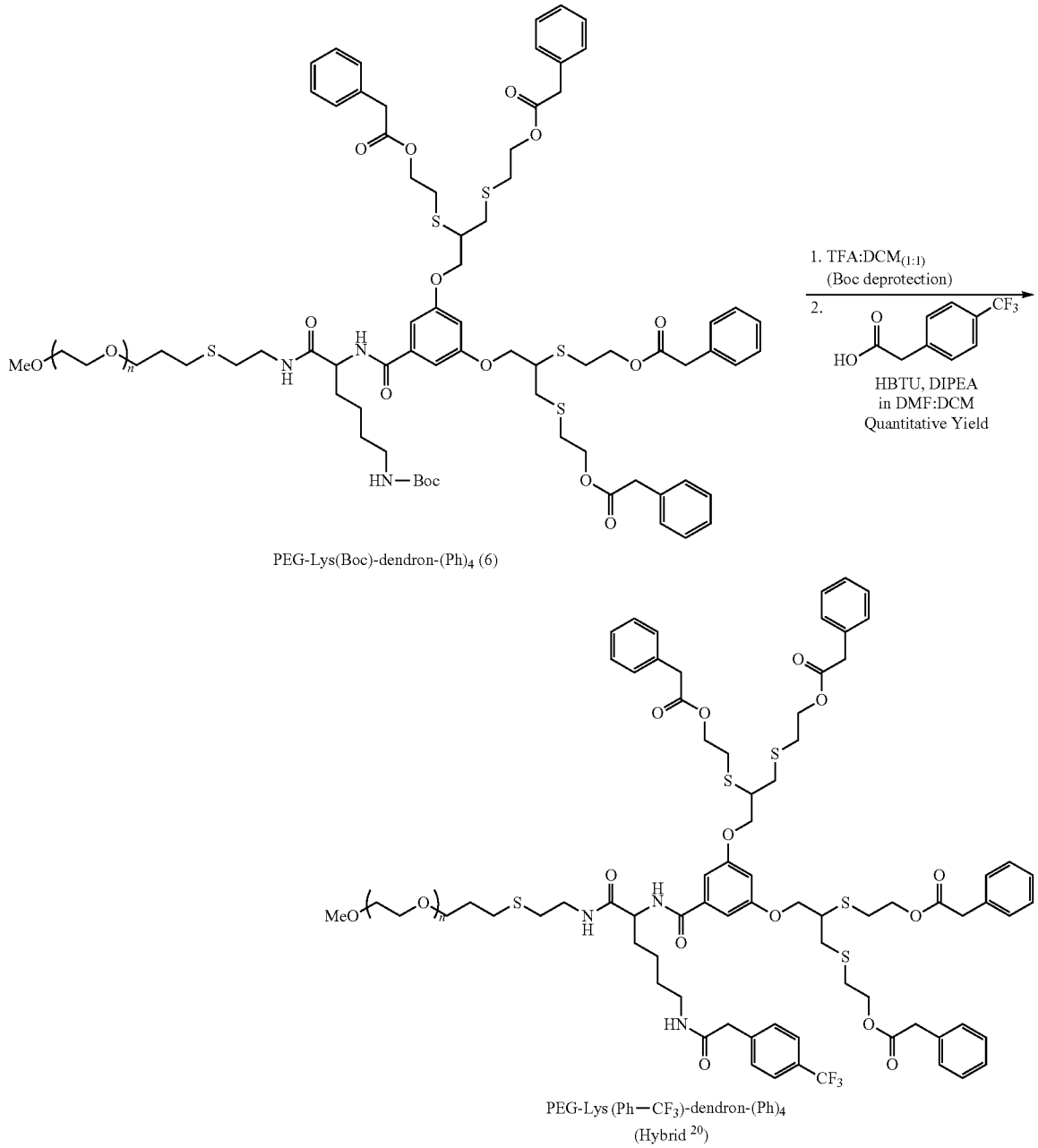

Scheme 15. Preparation of hybrid 20 from hybrid 6.

MeO-PEG$_{5kDa}$-Lys(Boc)-dendron-(Ph)$_4$ (hybrid 6, prepared in accordance with Example 2), were dissolved in DCM (1.5 mL) and TFA was added (1.5 mL). After 30 minutes the solution was evaporated to dryness and dried in vacuum. 2-(4-(trifluoromethyl)phenyl) acetic acid (5 eq.) and HBTU (5 eq.) were dissolved in DCM:DMF 1:1 (2 mL) followed by addition of DIPEA (20 eq.) and allowed to stir for 0.5 hour. The solution was added to 160 mg (0.03 mmol) of the deprotected hybrid (MeO-PEG$_{5kDa}$-Lys(NH$_2$)-dendron-(Ph)$_4$) dissolved in DCM (1 mL). The reaction was stirred for 1 hour. The crude mixture was purified by a silica column using 1% Acetic Acid in EtOAc followed by 20% MeOH in DCM. The fractions that contained the product were unified and the solvents were evaporated in vacuum to yield an oily residue. In order to facilitate the removal of residual solvents and solidification of the product, the oily residue was re-dissolved in DCM (2 mL) followed by addition of Hexane (6 mL). The white precipitate was filtered and washed twice with Ether and dried under high vacuum. The product was obtained as a white solid (160 mg, quantitative yield).

$^1$H NMR (CDCl$_3$): δ 7.50 (d, J=8.1 Hz, 2H, CF$_3$—Ar—H), 7.31 (d, J=8.0 Hz, 2H, CF$_3$—Ar—H), 7.28 (m, 22H, Ar—H), 7.14 (d, J=7.6 Hz, 1H, —CH—NH—CO—Ar), 6.98 (d, J=2 Hz, 2H, Ar—H), 6.82 (t, J=5.7 Hz, 1H, —CH$_2$—NH—CO—CH—), 6.55 (s, 1H, Ar—H), 6.01 (m, 1H, CF$_3$—Ar—CO—NH—), 4.51 (q, J=7.3 Hz, 1H, —CO—CH—NH—), 4.29-4.17 (m, 8H, —CH$_2$—O—CO—), 4.14-3.97 (m, 4H, —Ar—O—CH$_2$—), 3.80-3.43 (m, PEG backbone), 3.33 (s, 3H, CH$_3$—O-PEG), 3.17 (m, 2H, CF$_3$—Ar—CO—NH—CH$_2$—), 3.13-3.01 (m, 2H, —CH—S—), 2.92-2.75 (m, 8H, —CH—S—CH$_2$—+—CH—CH$_2$—S—CH$_2$—), 2.71 (t J=6.8 Hz, 8H, —CH—CH$_2$—S—CH$_2$—), 2.62-2.51 (m, 4H, —CH$_2$—CH$_2$—S—CH$_2$—), 1.98-1.65 (m, 4H, —NH—CH$_2$—CH$_2$—CH$_2$—CH$_2$—CH—+—O—CH$_2$—CH$_2$—CH$_2$—S—), 1.53-1.41 (m, 2H, —NH—CH$_2$—CH$_2$—CH$_2$—CH$_2$—CH—), 1.35 (m, 2H, —NH—CH$_2$—CH$_2$—CH$_2$—CH$_2$—CH—); $^{13}$C-NMR (CDCl$_3$) δ 171.8, 171.5, 170.3, 167.0, 159.7, 136.2, 133.8, 129.8, 129.4, 128.7, 127.3, 125.7, 125.3, 106.5, 105.0, 72.0, 70.7, 69.9, 69.5, 64.2, 63.9, 59.1, 53.6, 45.6, 44.9, 43.4, 43.3, 41.3, 39.0, 38.8, 34.9, 31.8, 31.6, 30.4, 29.8, 29.7, 28.7, 28.4, 22.7; $^{19}$F-NMR (NaF as internal reference, CDCl$_3$): 58.2 (—Ar—CF$_3$); FT-IR, ν (cm$^{-1}$): 2883, 1738, 1728, 1591, 1467, 1453, 1359, 1341, 1327, 1279, 1240, 1147, 1100, 1060, 960, 948, 842; GPC: Mn=6.4 kDa, PDI=1.04. Expected Mn=6.4 kDa. MALDI-TOF MS: molecular ion centered at 6.4 kDa.

Hybrid 20a (MeO-PEG$_{5kDa}$-Lys(Ph-CF$_3$)-dendron-(OH)$_4$):

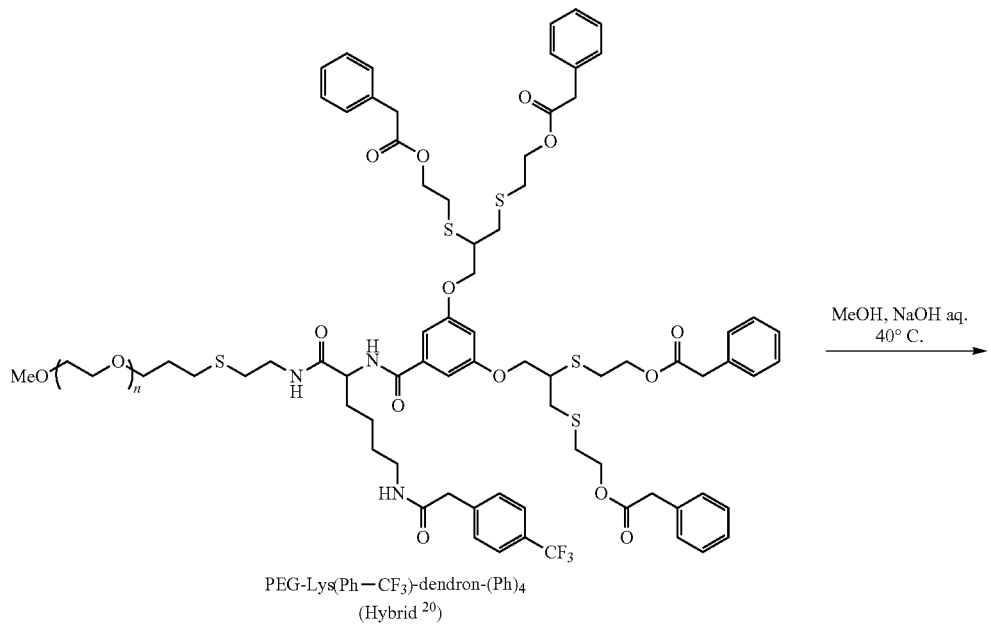

Scheme 16. Preparation of hybrid 20a.

PEG-Lys(Ph—CF$_3$)-dendron-(Ph)$_4$
(Hybrid 20)

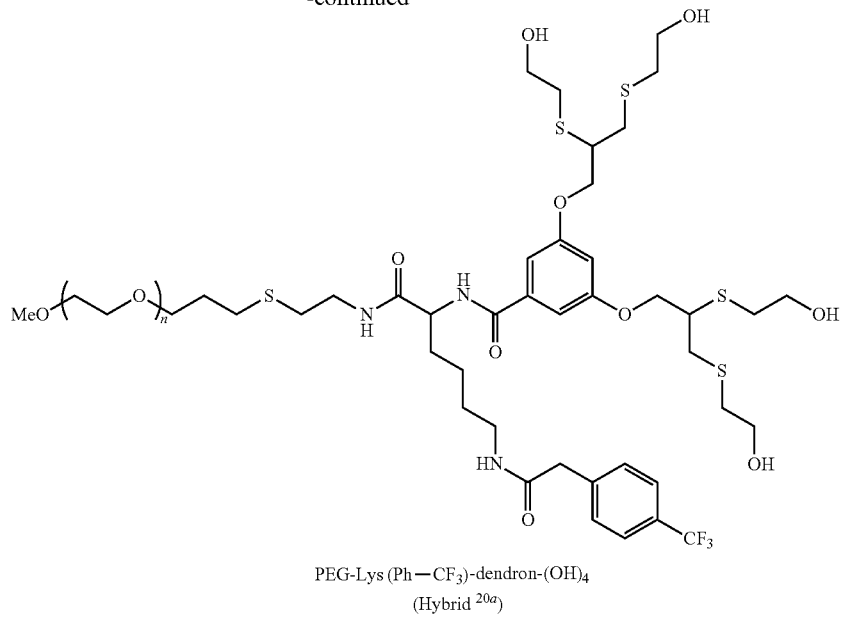

PEG-Lys(Ph—CF₃)-dendron-(OH)₄
(Hybrid 20a)

145 mg (0.02 mmol) of MeO-PEG$_{5kDa}$-Lys(Ph-CF₃)-dendron-(Ph)₄ (20) were dissolved in MeOH (1 mL) followed by the addition of a drop of water and about 40 µL of NaOH 1N (2 eq.) was added. The mixture was allowed to stir over night at 40° C. Complete hydrolysis was confirmed by HPLC. The pH of the mixture was neutralized (pH 7). The crude mixture was loaded on a DCM:MeOH 1:1v/v based LH20 SEC column. The fractions that contained the product were unified and the DCM and MeOH were evaporated in vacuum. In order to facilitate the removal of residual MeOH and solidification of the product, the oily residue was re-dissolved in DCM (1 mL) followed by addition of Hexane (3 mL). DCM and Hexane were evaporated to dryness and the obtained orange solid was dried under high vacuum. The product was obtained as an orange solid (130 mg, quantitative yield).

$^1$H NMR (CDCl₃): δ 7.80 (s, 1H, —CH—NH—CO—Ar), 7.49 (d, J=8.2 Hz, 2H, CF₃—Ar—H), 7.34 (d, J=8.3 Hz, 2H, CF₃—Ar—H), 7.16-7.04 (m, 2H, —CH—NH—CO—Ar+Ar—H), 6.63-6.49 (m, 1H, —CH₂—NH—CO—CH—+Ar—H), 4.55 (s, 1H, —CO—CH—NH—), 4.32-4.10 (m, 4H, —Ar—O—CH₂—), 3.83-3.40 (m, PEG backbone), 3.34 (s, 3H, CH₃—O-PEG), 3.30-3.11 (m, 5H, CF₃—Ar—CO—NH—CH₂—+—CH—S—), 2.92-2.88 (m, 2H, —CH—CH₂—S—CH₂—), 2.87-2.74 (m, 6H, —CH—S—CH₂—+—CH—CH₂—S—CH₂—), 2.70 (t, J=6.1 Hz, 4H, —CH—CH₂—S—CH₂—) 2.64-2.50 (m, 4H, —CH₂—CH₂—S—CH₂—), 1.78 (m, 4H, —NH—CH₂—CH₂—CH₂—CH₂—CH—+—O—CH₂—CH₂—CH₂—S—), 1.53-1.32 (m, 4H, —NH—CH₂—CH₂—CH₂—CH₂—CH—); $^{13}$C-NMR (CDCl₃) δ 171.9, 170.0, 166.7, 159.0, 139.0, 135.6, 129.2, 125.1, 125.0, 125.0, 106.0, 105.5, 98.9, 72.0, 70.7, 69.9, 63.2, 61.5, 61.4, 60.7, 58.5, 53.4, 44.8, 44.7, 42.6, 38.5, 38.4, 35.6, 34.5, 34.3, 34.3, 31.2, 31.1, 30.9, 29.1, 28.2, 27.9, 22.3; $^{19}$F-NMR (NaF as internal reference, CDCl₃): 57.7 (—Ar—CF₃); FT-IR, v (cm$^{-1}$): 2882, 1588, 1467, 1451, 1444, 1359, 1342, 1327, 1279, 1240, 1147, 1100, 1060, 960, 948, 842; GPC: Mn=6.4 kDa, PDI=1.16. Expected Mn=6.0 kDa. MALDI-TOF MS: molecular ion centered at 5.9 kDa.

Example 12—Critical Micelle Concentration (CMC) Measurements

For instrumentation and sample preparation, see Example 3.

CMC measurement for compound 1F, 1C and 8C: A 800 µM solution was prepared in diluent and sonicated for 15 minutes. This solution was repeatedly diluted by a factor of 1.5 with diluent. 150 µL of each solution were loaded onto a 96 wells plate. The fluorescence emission intensity was scanned for each well. Maximum emission intensity was plotted vs. hybrid concentration in order to determine the CMC. All measurements were repeated 3 times. The CMC for hybrid 20 was 4±1 µM.

Example 13—Dynamic Light Scattering (DLS)

General Sample Preparation:
Hybrid 20 was dissolved in phosphate buffer (pH 7.4) to give a final concentration of 640 µM. The solution was sonicated for 15 minutes and filtered through a 0.22 µm nylon syringe filter. Measurements were performed (t=o before addition al f PLE enzyme). All measurements were repeated 3 times.

Figure 22:
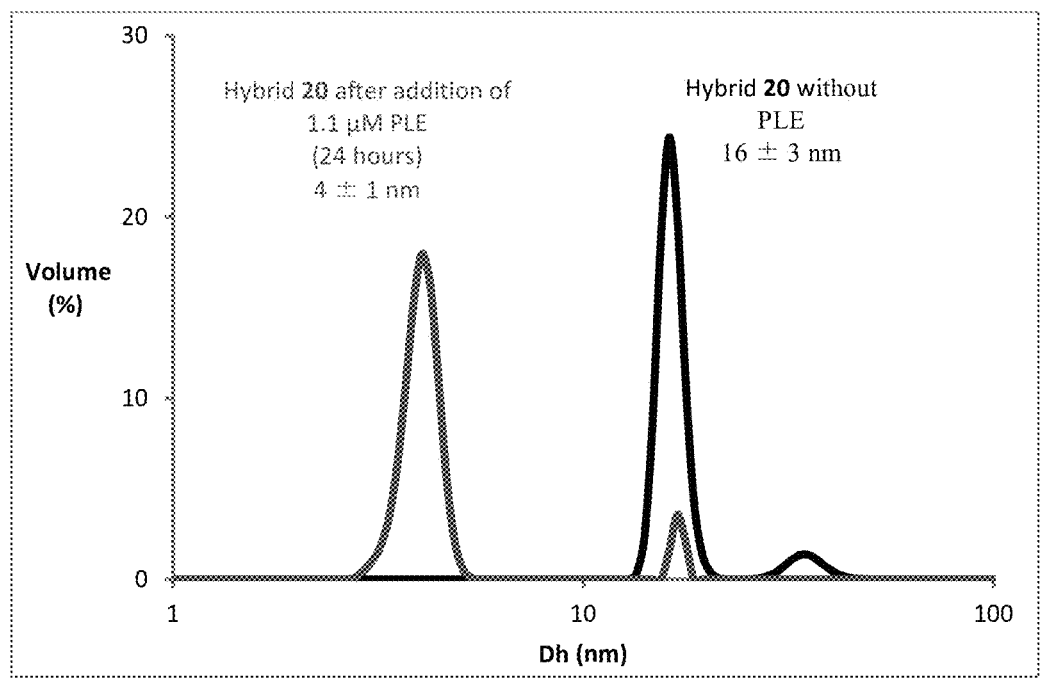
FIG. 22: Micelle degradation of hybrid 20 (640 µM) in presence of 1.1 µM PLE enzyme.

For Micelle Degradation in the Presence of 1.1 µM PLE Enzyme:
20.0 µL of PLE enzyme stock solution (28.4 µM in phosphate buffer pH 7.4) were added 500 µL solution of hybrid 20 (640 µM). Measurements were performed after 24 hours. All measurements were repeated 3 times. FIG. 22 depicts micelle degradation of hybrid 20 (640 µM) in the presence of 1.1 µM PLE enzyme.

Example 14—Monitoring Micelle Disassembly with Nile Red Fluorescence

Instrumentation: Monitoring of micelle disassembly rate by enzymes was performed using an Agilent Technologies Cary Eclipse Fluorescence Spectrophotometer.
Instrument Method:
(a) Excitation: 550 nm
(b) Emission scan: 580-800 nm (c) Excitation and Emission slits width: 10 nm
(d) Scan rate: 620 nm/min
(e) Temperature control: 27° C.
(f) Sample preparation and measurement: Hybrid 20 was separately dissolved in phosphate buffer (pH 7.4) to give a concentration of 640 μM. 4 mL of the solution were accurately measured and 1.8 μL of Nile Red stock solution (0.88 mg/mL in Ethanol) were added to give a final concentration of 1.25 μM. To each solution 40.4 μL of NaF stock solution (64 mM in Phosphate buffer pH 7.4) were added to give final concentration of 640 μM. 700 μL of the hybrid solution containing Nile Red and NaF were accurately transferred to separate quartz cuvettes for reference measurements without PLE enzyme and also for t=0 measurements.

For Micelle Degradation in the Presence of 1.1 μM PLE Enzyme:

128 μL of PLE enzyme stock solution (28.4 μM in phosphate buffer pH 7.4) were added to 3.2 mL of a 640 μM solution of hybrid 20 containing Nile Red and NaF and mixed manually to give final PLE concentration of 1.1 μM. 700 μL of the solution were accurately transferred to separate quartz cuvettes (1.2 mL were accurately transferred to a proper HPLC vail for monitoring enzymatic degradation by HPLC measurements and 500 μL were transferred to NMR tube for $^{19}$F NMR analysis). Repeating fluorescence scans were performed every 20 minutes for 8 hours. All measurements were repeated twice.

Figure 23:
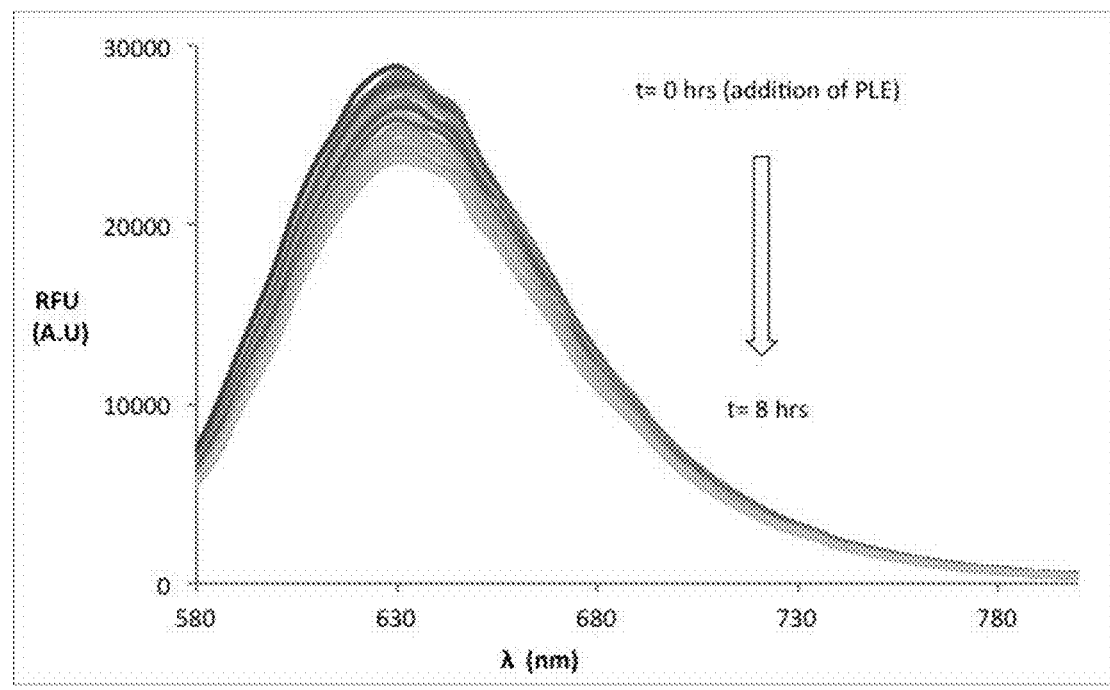
FIG. 23: Fluorescence emission spectra of Nile Red (1.25 µM) in the presence of hybrid 20 (640 µM) as a function of time after the addition of 1.1 µM PLE. A decrease in the intensity was observed as Nile Red was released into solution due to micelles degradation.
Figure 24:
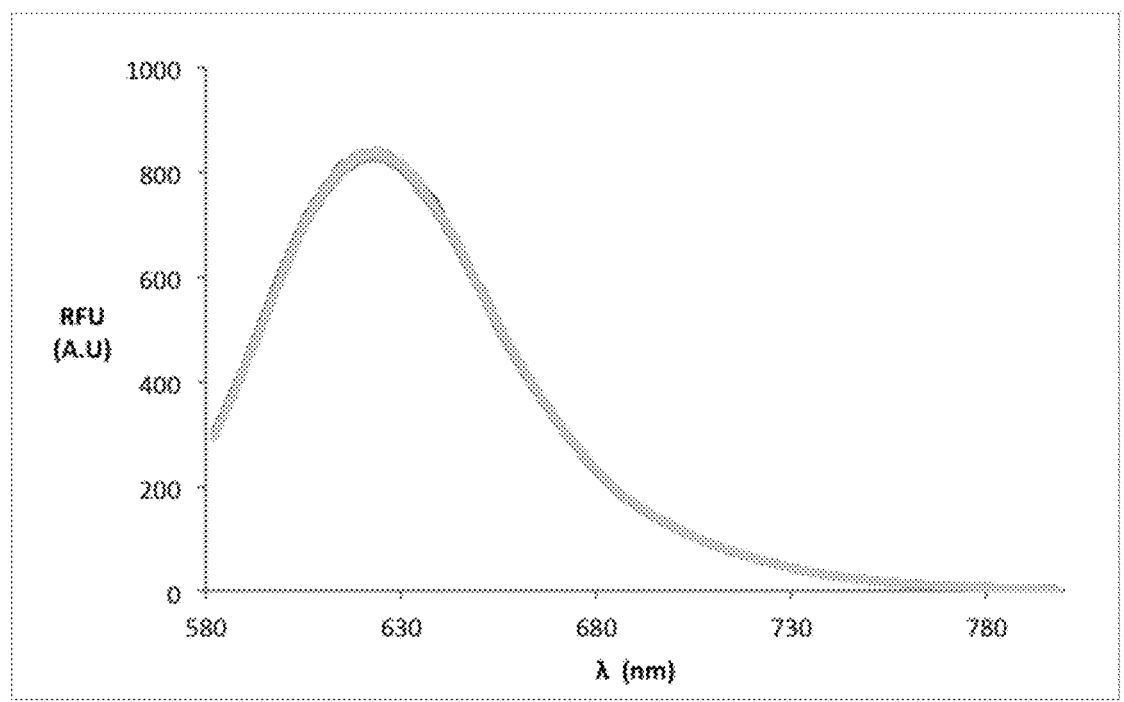
FIG. 24: Fluorescence emission spectra of Nile Red (1.25 µM) in the presence of hybrid 20 (640 µM) in the absence of PLE enzyme over 8 hours.

FIG. 23 depicts fluorescence emission spectra of Nile Red (1.25 μM) in the presence of hybrid 20 (640 μM) as a function of time after the addition of 1.1 μM PLE. A decrease in the intensity was observed as Nile Red was released into solution due to micelles degradation. As control, FIG. 24 depicts fluorescence emission spectra of Nile Red (1.25 μM) in the presence of hybrid 20 (640 μM) in absence of PLE enzyme over 8 hours. No decrease in intensity was observed.

Example 15—HPLC Monitoring of Enzymatic Degradation

For instrumentation, solutions and general reaction conditions, see Example 7.

Injection volume: 10 μL.

Sample preparation: Hybrid 20 was dissolved in phosphate buffer (pH 7.4) to give concentrations of 640 μM. 4 mL of the solution were accurately measured and 1.8 μL of Nile Red stock solution (0.88 mg/mL in Ethanol) were added to give a final concentration of 1.25 μM. To the solution 40.4 μL of NaF stock solution (64 mM in Phosphate buffer pH 7.4) were added to give final concentration of 640 μM. 100 μL of the hybrid solution containing Nile Red and NaF were accurately transferred to separate HPLC vials. 10 μL of the hybrid 20 solution were injected to the HPLC as t=0 injection.

For Micelle Degradation in the Presence of 1.1 μM PLE Enzyme:

128 μL of PLE enzyme stock solution (28.4 μM in phosphate buffer pH 7.4) were added to 3.2 mL of 0 the tested hybrid solution (640 μM) containing Nile Red and NaF and mixed manually to give final PLE concentration of 1.1 μM. 1.2 mL of each solution were accurately transferred to separate HPLC vials (700 μL were accurately transferred to a quartz cuvette for monitoring enzymatic degradation by fluorescence measurements and 500 μL were transferred to NMR tube for $^{19}$F NMR analysis). Enzymatic degradation was monitored by repeating 10 μL injections from the same vial over 8 hours by 10 μL injections from the same vail over 8 hours. All measurements were repeated twice.

FIG. 20a depicts the HPLC monitoring of micelle degradation in presence of 1.1 μM PLE enzyme over time. The HPLC data showed the direct enzymatic transformation of hybrid 20 into the corresponding hydrophilic hybrid 20a.

Example 16—$^{19}$F NMR Spectroscopy

Instrumentation: $^{19}$F NMR experiments were conducted at 376 MHz using a Bruker Avance III instrument equipped with a BBFO probe. NaF (640 μM) was used as an internal reference added directly to the solution and its chemical shift was set to zero.

Samples preparation: Hybrid 20 was dissolved in phosphate buffer (pH 7.4) and 10% D$_2$O (v/v) to give a concentration of 640 μM. 4 mL of the solution were accurately measured and 1.8 μL of Nile Red stock solution (0.88 mg/mL in Ethanol) were added to give a final concentration of 1.25 μM. To the solution 40.4 μL of NaF stock solution (64 mM in Phosphate buffer pH 7.4) were added to give final concentration of 640 μM. 500 μL of each hybrid solution containing Nile Red and NaF were accurately transferred to separate NMR tubes.

For Micelle Degradation in the Presence of 1.1 μM PLE Enzyme:

128 μL of PLE enzyme stock solution (28.4 μM in phosphate buffer pH 7.4) were added to 3.2 mL of the tested hybrid solution (640 μM) containing Nile Red and NaF and mixed manually to give final PLE concentration of 1.1 μM. 500 μL of each solution were accurately transferred to separate NMR tubes for $^{19}$F NMR analysis (1.2 mL were transferred to a proper HPLC vial for monitoring enzymatic degradation by HPLC measurements and 700 μL were accurately transferred to a quartz cuvette for monitoring enzymatic degradation by fluorescence measurements).

Sample Preparation of Hybrid 20a as a Reference Product of Enzymatic Degradation:

Hybrid 20a was dissolved in phosphate buffer (pH 7.4) and 10% D$_2$O (v/v) to give a concentration of 640 μM. 1.0 mL of the solution were accurately measured. To the solution of hybrid 20a (640 μM) 40.4 μL of phenyl acetic acid stock solution (64 mM in phosphate buffer pH 7.4) were added to give final concentration of 2.56 mM. To the solution 10.1 μL of NaF stock solution (64 mM in Phosphate buffer pH 7.4) were added to give final concentration of 640 μM. 20 μL of PLE enzyme stock solution (28.4 μM in phosphate buffer pH 7.4) were added to 500 μL of each solution of the tested hybrid (in order to imitate the same conditions as in the micelle degradation solution). 500 μL of the hybrid solution containing the degradation products, Nile Red, NaF and PLE were accurately transferred to separate NMR tubes.

$^{19}$F NMR Monitoring of Enzymatic Degradation:

Monitoring of micelles disassembly rate by PLE enzyme was performed by 1D $^{19}$F NMR spectra with repetition of 8 seconds of samples containing solution of hybrid 20 separately without addition of PLE enzyme (samples were prepared as described earlier) (t=0). With addition of PLE enzyme to each of the tested solution of hybrid 20 (samples were prepared as described earlier) repeating 1D $^{19}$F NMR experiments in which a delay of 1608 sec was embedded were performed every 30 min for 8 hours. Chemical shift of NaF was set to zero and its integration was set to 1. The kinetic rates were achieved by plotting the normalized integral intensities rations of the two signals in the spectra over time. All measurements were repeated twice T$_1$ and T$_2$ Measurements:

T$_1$ of each sample was determined using an inversion recovery pulse sequence with repetition time of 8 seconds. T$_1$ values were obtained by fitting the $^{19}$F signal intensities vs τ according to equation Mz=Mo [1-2 exp(-τ/T1)]. The analyzed samples were separate solutions of hybrid 20 without PLE enzyme, hybrid 20 24 hours after addition of PLE and hybrid 20a (all samples were prepared as described earlier). All measurements were repeated 3 times.

$T_2$ of each sample was analyzed using a Carr Purcell Meiboom Gill (CPMG) sequence with repetition of 8 seconds. $T_2$ values were obtained by fitting the $^{19}F$ signal integral intensities vs τ to a single exponential decay. The analyzed samples were separate solutions of hybrid 20 without PLE enzyme, hybrid 20 24 hours after addition of PLE and hybrid 20a (all samples were prepared as described earlier). All measurements were repeated 3 times.

ON/OFF Spectra:

The measurements were acquired using CPMG 1D sequence with repetition of 8 seconds and echo time TE=80 ms. The analyzed samples were separate solutions of hybrid 20 without PLE enzyme and 24 hours after addition of PLE enzyme (all samples were prepared as described earlier).

Example 17—Materials and Methods

HPLC: All measurements were recorded on a Waters Alliance e2695 separations module equipped with a Waters 2998 photodiode array detector. All solvents were purchased from Bio-Lab Chemicals and were used as received. All solvents are HPLC grade.

$^1H$ and $^{13}C$ NMR: spectra were recorded on Bruker Avance I and Avance III 400 MHz and 100 MHz ($^{13}C$) spectrometers. Chemical shifts are reported in ppm and referenced to the solvent. The molecular weights of the PEG-dendron hybrids were determined by comparison of the areas of the peaks corresponding to the PEG block (3.63 ppm) and the protons peaks of the dendrons.

$^{19}F$ NMR: spectra were collected on a Bruker Avance III 376 MHz spectrometer by using sodium fluoride as the internal reference.

$^{19}F$ MRI experiments: all measurements were conducted on an Avance-III 14.1T wide-bore NMR/MRI scanner (Bruker, Germany), equipped with a micro2.5 gradient system, capable of producing gradient pulses of 300 gauss/cm in the x, y, z-directions.

GPC: All measurements were recorded on Viscotek GPC-max by Malvern using refractive index detector and PEG standards (purchased from Sigma-Aldrich) were used for calibration. DMF+25 mM $NH_4Ac$ was used as mobile phase.

Infrared spectra: All measurements were recorded on a Bruker Tensor 27 equipped with a platinum ATR diamond.

Absorbance and fluorescence spectra (including CMC measurements): Spectra were recorded on an Agilent Technologies Cary Eclipse Fluorescence Spectrometer using quartz cuvettes or on TECAN Infinite M200Pro plate reader device.

MALDI-TOF MS: Analysis was conducted on a Bruker AutoFlex MALDI-TOF MS (Germany) and also on a Waters MALDI synapt (USA). DHB matrix was used.

TEM: Images were taken by a Philips Tecnai F20 TEM at 200 kV.

DLS: All measurements were recorded on a Malvern Zetasizer NanoZS (for fluorescence experiments) or VASCO-3 Particle Side Analyzer (Cordouan) for $^{19}F$-MR experiments.

Materials: Poly (Ethylene Glycol) methyl ether 5 kDa, 2-(Boc-amino)-ethanethiol (97%), 2,2-dimethoxy-2-phenylacetophenone (DMPA, 99%), Penicillin G Amidase from *Escherichia coli* (PGA), Esterase from porcine liver (PLE), Allyl bromide (99%), 4-Nitrophenol (99.5%), N,N'-dicyclohexylcarbodiimide (DCC, 99%), Fmoc-Lys(Boc)-OH (98%), Fluorescein 5-isothiocyanate (FITC, 90%), Sephadex® LH20 and 4-(Trifluoromethyl)Phenylacetic Acid (97%) were purchased from Sigma-Aldrich. Cystamine hydrochloride (98%), potassium hydroxide and DIPEA were purchased from Merck. O-(Benzotriazol-1-yl)-N,N,N',N'-tetramethyluronium hexafluorophosphate (HBTU, 99.9%) was purchased from Chem-Impex. Trifluoroacetic acid (TFA) and 2-Mercaptoethanol (99%) was purchased from Alfa Aesar and phenyl acetic acid was purchased from Fluka. Sodium hydroxide and all solvents were purchased from Bio-Lab and were used as received. Deuterated solvents for NMR were purchased from Cambridge Isotope Laboratories, Inc.

Gel permeation chromatography (GPC) was performed according to the following conditions:
  (a) Columns. 2×PSS GRAM 1000 Å+PSS GRAM 30 Å
  (b) Columns Temperature: 50° C.
  (c) Flow rate: 0.5 ml/min
  (d) Mobile phase: DMF+25 mM $NH_4Ac$
  (e) Detector: Refractive index detector at 50° C.
  (f) Injection Volume: 50 µL
  (g) General sample preparation: Hybrids were dissolved in mobile phase to give final concentrations of 10 mg/ml. Solution was filtered through a 0.22 µm PTFE syringe filter.

Transmission Electron Microscopy (TEM):

General Sample Preparation:

5 µL sample solution were dropped cast onto carbon coated copper grids and inspected in a transmission electron microscope (TEM), operated at 200 kV (Philips Tecnai F20). The excessive solvent of the droplet was wiped away using a solvent-absorbing filter paper after 1 min and the sample grids were ft to dry in air at room temperature for 5 minutes. This procedure was repeated 3 times. After the third cycle the sample grids were left to dry in air at room temperature overnight.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

REFERENCES (1) Raghupathi, K. R.; Azagarsamy, M. a.; Thayumanavan, S. *Chem.-A Eur. J.* 2011, 17, 11752.
(2) Guo, J.; Zhuang, J.; Wang, F.; Raghupathi, K. R.; Thayumanavan, S. *J. Am. Chem. Soc.* 2014, 136, 2220.
(3) Rosenbaum, I.; Harnoy, A. J.; Tirosh, E.; Buzhor, M.; Segal, M.; Frid, L.; Shaharabani, R.; Avinery, R.; Beck, R.; Amir, R. J. *J. Am. Chem. Soc.* 2015, 137, 2276.
(4) Harnoy, A. J.; Rosenbaum, I.; Tirosh, E.; Ebenstein, Y.; Shaharabani, R.; Beck, R.; Amir, R. J. *J. Am. Chem. Soc.* 2014, 136, 7531.
(5) A. Y. Louie, M. M. Huber, E. T. Ahrens, U. Rothbacher, R. Moats, R. E. Jacobs, S. E. Fraser and T. J. Meade, *Nat. Biotechnol.*, 2000, 18, 321-5.
(6) R. Napolitano, G. Pariani, F. Fedeli, Z. Baranyai, M. Aswendt, S. Aime and E. Gianolio, *J. Med. Chem.*, 2013, 56, 2466-77.
(7) J. Hu, G. Zhang and S. Liu, *Chem. Soc. Rev.*, 2012, 41, 5933.
(8) D. Roy, J. N. Cambre and B. S. Sumerlin, *Prog. Polym. Sci.*, 2010, 35, 278-301.
(9) A. P. Blum, J. K. Kammeyer, A. M. Rush, C. E. Callmann, M. E. Hahn and N. C. Gianneschi, *J. Am. Chem. Soc.*, 2015, 137, 2140-2154.
(10) K. Zhou, H. Liu, S. Zhang, X. Huang, Y. Wang, G. Huang, B. D. Sumer and J. Gao, *J. Am. Chem. Soc.*, 2012, 134, 7803-11.
(11) J. Qiao, L. Qi, Y. Shen, L. Zhao, C. Qi, D. Shangguan, L. Mao and Y. Chen, *J. Mater. Chem.*, 2012, 22, 11543-11549.

(12) Y. Jiang, X. Hu, J. Hu, H. Liu, H. Zhong and S. Liu, *Macromolecules*, 2011, 44, 8780-8790.
(13) C. Li and S. Liu, *Chem. Commun. (Camb).*, 2012, 48, 3262-78.
(14) X. Huang, G. Huang, S. Zhang, K. Sagiyama, O. Togao, X. Ma, Y. Wang, Y. Li, T. C. Soesbe, B. D. Sumer, M. Takahashi, a. D. Sherry and J. Gao, *Angew. Chemie-Int. Ed.*, 2013, 52, 8074-8078.
(15) H. Wang, K. R. Raghupathi, J. Zhuang and S. Thayumanavan, *ACS Macro Lett.*, 2015, 4, 422-425.
(16) F. Wang, A. Klaikherd and S. Thayumanavan, *J. Am. Chem. Soc.*, 2011, 133, 13496-13503.
(17) M. V. Walter and M. Malkoch, *Chem. Soc. Rev.*, 2012, 41, 4593.
(18) R. Hoogenboom, *Angew. Chemie-Int. Ed.*, 2010, 49, 3415-3417.
(19) A. B. Lowe, *Polymer (Guildfi).*, 2014, 55, 5517-5549.

What is claimed is:
1. A hybrid polymer comprising:
a hydrophilic polyethylene glycol (PEG) polymer;
a hydrophobic dendron, the dendron comprising at least one enzymatically cleavable hydrophobic end group that is covalently attached to the dendron; and
at least one labeling moiety selected from a fluorescent dye, a dark quencher, and a fluorinated labeling moiety, wherein the PEG polymer, hydrophobic dendron and labeling moiety are covalently attached through a trifunctional moiety that is capable of attaching to the hydrophobic dendron, the PEG polymer, and the labeling moiety, and wherein the trifunctional moiety is present at a focal point between the PEG polymer and the hydrophobic dendron.
2. The hybrid polymer according to claim 1, wherein the labeling moiety is a fluorescent dye or a dark quencher.
3. The hybrid polymer according to claim 2, wherein the fluorescent dye or dark quencher is selected from the group consisting of a coumarin, a cyanine dye, an azo dye, an acridine, a fluorone, an oxazine, a phenanthridine, a naphthalimide, a rhodamine, a benzopyrone, a perylene, a benzanthrone, and a benzoxanthrone.
4. The hybrid polymer according to claim 3, wherein the fluorescent dye or dark quencher is or is the residue of a compound selected from the group consisting of Coumarin, Fluorescein, Cyanine 3 (Cy3), Cyanine 5 (Cy5), Cyanine 7 (Cy7), Alexa dyes, bodipy derivatives, (E)-2-(4-(phenyldiazenyl)phenoxy)acetic acid, 3-(3',3'-dimethyl-6-nitrospiro[chromene-2,2'-indolin]-1'-yl)propanoate (Spiropyran), 3,5-dihydroxybenzoate, (E)-2-(4-(phenyldiazenyl)phenoxy)acetic acid, and combinations thereof.
5. The hybrid polymer according to claim 1, wherein the labeling moiety is a fluorinated labeling moiety, the fluorinated labeling moiety being a magnetic resonance (MR) probe capable of turning on a $^{19}$F-MR signal.
6. The hybrid polymer according to claim 1, wherein the trifunctional moiety is selected from the group consisting of an amino acid, a C1-C20 alkylene, a C2-C20 alkenylene, a C2-C20 alkynylene and an arylene, each comprising at least three functional groups selected from the group consisting of —C(=O)—O—, —NH—, —O—, —S—, —C(=O)—, —O—C(=O)—O—, —C(=O)—NH—, —NH—C(=O)—NH—, —NH—C(=O)—O—, —S(=O)—, —S(=O)—O—, —PO(=O)—O—, and any combination thereof.
7. The hybrid polymer according to claim 6, wherein the trifunctional moiety is an amino acid capable of attaching to the hydrophobic dendron, the PEG polymer, and the fluorescent dye through its carboxyl group, amino group, and side chain.
8. The hybrid polymer according to claim 7, wherein the trifunctional moiety is an alpha-amino acid selected from the group consisting of lysine, aspartic acid, glutamic acid, tyrosine, asparagine, serine, homoserine, cysteine, homocysteine, glutamine, threonine, ornithine, citrulline and arginine, preferably wherein the alpha-amino acid is lysine.
9. The hybrid polymer according to claim 1, wherein the enzymatically cleavable hydrophobic end group is conjugated to the dendron through an enzymatically cleavable functional group selected from the group consisting of an ester, an amide, a carbamate, a carbonate, a urea, a sulfate, an amidine, an ether, a phosphate, a phosphoamide, sulfamates, and a trithionate.
10. The hybrid polymer according to claim 9, wherein the enzymatically cleavable hydrophobic end group is conjugated to the dendron through an ester which is cleavable by an esterase.
11. The hybrid polymer according to claim 10, wherein the esterase is selected from the group consisting of carboxylesterase, arylesterase, and acetylesterase.
12. The hybrid polymer according to claim 9, wherein the enzymatically cleavable hydrophobic end group is conjugated to the dendron through an amide which is cleavable by an amidase.
13. The hybrid polymer according to claim 12, wherein the amidase is selected from the group consisting of arylacylamidase, aminoacylase, alkylamidase, and phthalyl amidase.
14. The hybrid polymer according to claim 1, wherein the enzymatically cleavable hydrophobic end group is represented by the structure —O—C(O)—R', —C(O)—OR'—NH—C(O)—R' or —C(O)—NHR' wherein R' is C1-C12 alkyl or an aryl.
15. The hybrid polymer according to claim 1, wherein the dendron comprises a plurality of enzymatically cleavable hydrophobic end groups, and wherein the enzymatically cleavable hydrophobic end groups are present at one or more terminal repeating units (terminal generation) of the hydrophobic dendron.
16. The hybrid polymer system according to claim 1, wherein the PEG has an average molecular weight between 0.5 and 70 kDa; or wherein the PEG has at least 10 repeating units of ethylene glycol monomers.
17. The hybrid polymer according to claim 1, wherein the PEG is linked to the dendron or the trifunctional moiety through a PEG terminal group selected from the group consisting of —(CH$_2$)$_t$—X—(CH$_2$)$_t$—X—, —X—(CH$_2$)$_t$—X—, —(CH$_2$)$_t$— wherein X is independently at each occurrence selected from O, S and NH, and t is independently at each occurrence 1-10; —O—, —S—, —NH—, —C(=O)—, —C(=O)—O—, —O—C(=O)—O—, —C(=O)—NH—, —NH—C(=O)—NH—, —NH—C(=O)—O—, —S(=O)—, —S(=O)—O—, —PO(=O)—O—, —C≡C—, triazolyl, and any combination thereof, preferably, wherein the PEG terminal functional group is —(CH$_2$)$_3$—S—(CH$_2$)$_2$—NH—.
18. The hybrid polymer according to claim 1, comprising:
a trifunctional moiety having a first bond to a PEG polymer, a second bond to a labeling moiety selected from a fluorescent dye, a dark quencher and a fluorinated labeling moiety, and a third bond, directly or through a linker or branching unit, to a first generation dendron which comprises at least one functional group capable of binding to a further generation or to said enzymatically cleavable hydrophobic end group; and
optionally, at least one additional generation which is covalently bound to said first generation or preceding generation, and optionally to a further generation, wherein each of said optional generations comprises at least one functional group capable of binding to said first generation, to a preceding generation, to a further generation, and/or to said enzymatically cleavable hydrophobic end group, each of said bonds being formed directly or through a linker or branching unit.

19. The hybrid polymer according to claim 1, wherein each generation of the hydrophobic dendron comprises a linear or branched C1-C20 alkylene, C2-C20 alkenylene, C2-C20 alkynylene or arylene moiety which is substituted at each end with a group selected from the group consisting of —O—, —S—, —NH—, —C(=O)—, —C(=O)—O—, —O—C(=O)—O—, —C(=O)—NH—, —NH—C(=O)—NH—, —NH—C(=O)—O—, —S(=O)—, —S(=O)—O—, —PO(=O)—O—, and any combination thereof.

20. The hybrid polymer according to claim 19, wherein each generation of the dendron is derived from a compound selected from the group consisting of HX—CH$_2$—CH$_2$—XH, HX—(CH$_2$)$_{1-3}$—CO$_2$H and HX—CH$_2$—CH(XH)—CH$_2$—XH wherein X is independently at each occurrence NH, S or O.

21. The hybrid polymer according to claim 20, wherein each generation of the dendron is derived from a compound selected from the group consisting of HS—CH$_2$—CH$_2$—OH, HS—(CH$_2$)$_{1-3}$—CO$_2$H and HS—CH$_2$—CH(OH)—CH$_2$—OH.

22. The hybrid polymer according to claim 1, further comprising a linker or branching unit which connects the trifunctional moiety to the first generation dendron and/or which forms a part of the first generation dendron, and/or which connects between dendron generations.

23. The hybrid polymer according to claim 22, wherein the linker/branching unit moiety is selected from a group consisting of a substituted or unsubstituted acyclic, cyclic or aromatic hydrocarbon moiety, heterocyclic moiety, a heteroaromatic moiety or any combination thereof, preferably wherein the linker moiety/branching unit is a substituted arylene, a C1-C20 alkylene, a C2-C20 alkenylene, or a C2-C20 alkynylene each comprising at least one functional group selected from the group consisting of —O—, —S—, —NH—, —C(=O)—, —O—C(=O)—O—, —C(=O)—O—, —C(=O)—NH—, —NH—C(=O)—NH—, —NH—C(=O)—O—, —S(=O)—, —S(=O)—O—, —PO(=O)—O—, —C≡C—, —(CH$_2$)$_t$— wherein t is an integer of 1-10, and any combination thereof.

24. The hybrid polymer according to claim 1, which is represented by the structure of formula (I):

(I)

wherein Q is selected from the group consisting of OR wherein is H or a C1-C4 alkyl;
NH$_2$, SH and COOH;

T is absent or is a functional group selected from the group consisting of —(CH$_2$)$_t$—X—(CH$_2$)$_t$—X—, —X—(CH$_2$)$_t$—X—, —(CH$_2$)$_t$— wherein X is independently at each occurrence selected from O, S and NH, and t is independently at each occurrence 1-10; —O—, —S—, —NH—, —C(=O)—, —C(=O)—O—, —O—C(=O)—O—, —C(=O)—NH—, —NH—C(=O)—NH—, —NH—C(=O)—O—, —S(=O)—, —S(=O)—O—, —PO(=O)—O—, —C=C—S≡C—, any combination thereof;

B is a trifunctional moiety comprising a labeling moiety covalently attached thereto;

Y is independently at each occurrence absent or is a linker moiety/branching unit;

Z is independently at each occurrence a dendron repeating unit selected from the group consisting of:

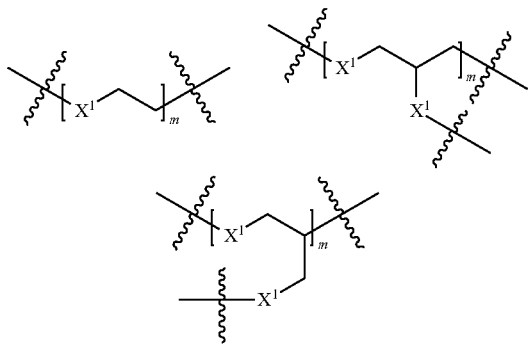

and any combination of the foregoing;
wherein X$^1$ is independently, at each occurrence, selected from the group consisting of O, S and NH;
A represents a multiplicity of hydrophobic end groups conjugated to terminal units of the dendron through at least one enzymatically cleavable functional group selected from the group consisting of an ester, an amide, a carbamate, a carbonate, a urea, a sulfate, an amidine, an ether, a phosphate, a phosphoamide, sulfamates, and a trithionate;
n is an integer in the range of 1 to 1,500; and
m and z are each an integer of 1 to 15.

25. The hybrid polymer according to claim 24, wherein the trifunctional moiety B is lysine, which is linked to a labeling moiety through its side chain amino group:

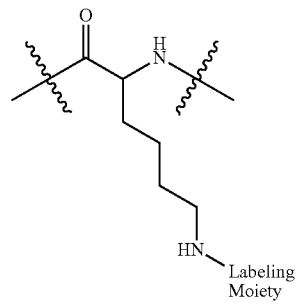

26. The hybrid polymer according to claim 24, wherein the terminal unit of said dendron is represented by any of the following structures:

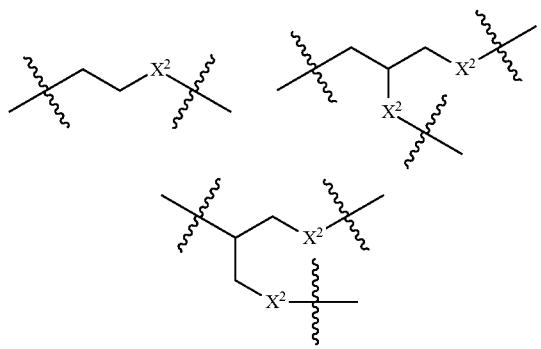

wherein X$^2$ has the same meaning as X$^1$.

27. The hybrid polymer according to claim 24, wherein each hydrophobic end group A is conjugated to the dendron through an enzymatically cleavable functional group represented by the structure:

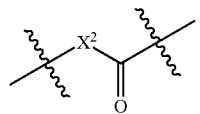

wherein $X^2$ is a part of the terminal unit of said dendron and C(=O) is part of hydrophobic end group; or wherein $X^2$ is part of the hydrophobic end group and C(=O) is a part of the terminal repeating unit of said dendron, or wherein $X^2$—C(=O) are part of the hydrophobic end group, or wherein $X^2$—C(=O) is part of the terminal unit of said dendron; and wherein $X^2$ has the same meaning as $X^1$.

28. The hybrid polymer according to claim 24, which is represented by the structure of formula (II):

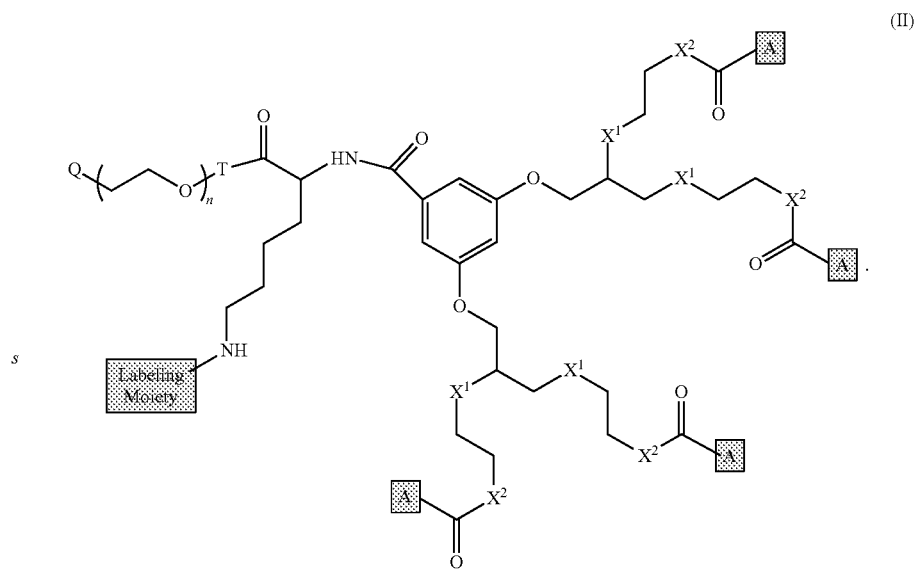

29. The hybrid polymer according to claim 28, which is represented by the structure of formula (IIa):

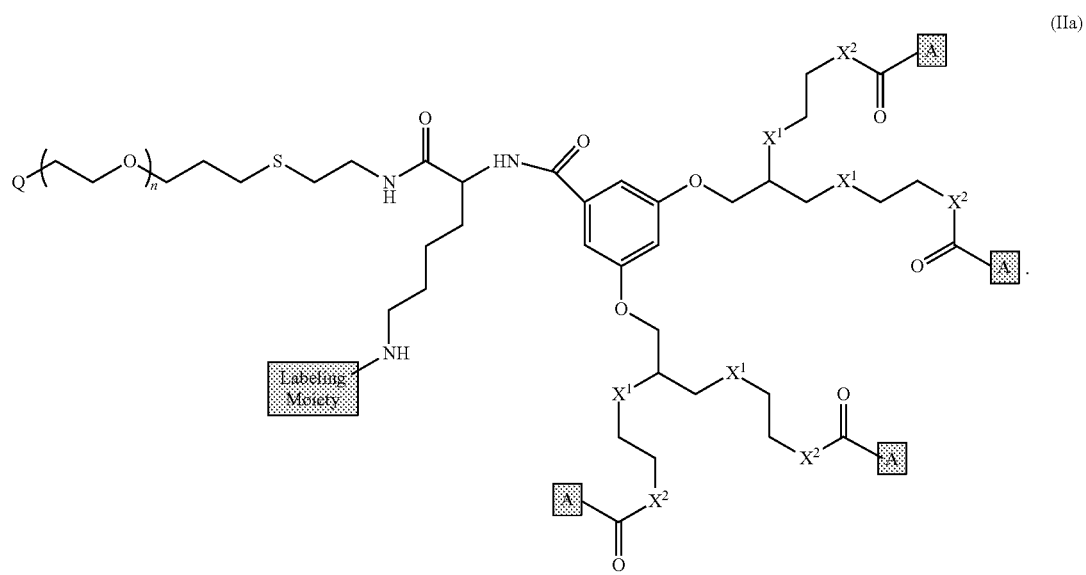

30. The hybrid polymer according to claim 1, which is represented by the structure of any of formulae 1C, 1F, 8C, 8F, 12a, 12b, 13a, 13b, 14a, 14b, 15a, 15b, 16a, 16b, 18 or 20.

31. A self-assembled amphiphilic delivery system in micellar form, comprising at least one hybrid polymer according to claim 1, wherein the micelle disassembles upon enzymatic cleavage of the hydrophobic end group; and wherein the labeling moiety provides a different signal in the assembled vs. unassembled state of the micelle.

32. The delivery system according to claim 31, wherein the labeling moiety in the hybrid polymer is a fluorescent dye, wherein the fluorescent dye is a self-quenching dye or an excimer forming dye, and wherein the fluorescence of the dye, when used alone or in combination with another dye or a dark quencher, is wholly or partially quenched or is shifted upon micelle assembly, and said dye regains its intrinsic fluorescence upon micelle disassembly.

33. The delivery system according to claim 31, comprising a multiplicity of hybrid polymers containing the same labeling moiety, or mixture of hybrid polymers containing different labeling groups.

34. The delivery system according to claim 31 comprising:
(a) a hybrid polymer comprising a self-quenching fluorescent dye (FRET), wherein the fluorescence of the dye is wholly or partially quenched upon micelle assembly (TURN OFF);
(b) a mixture of a hybrid polymer comprising a fluorescent dye and a hybrid polymer comprising dark quencher, wherein the fluorescence of the dye is wholly or partially quenched upon micelle assembly (TURN OFF);
(c) a mixture of hybrid polymers comprising two or more different fluorescent dyes, wherein the fluorescence of the dyes is shifted upon micelle assembly (FRET) and disassembly (spectral shift); or
(d) a hybrid polymer comprising an excimer forming fluorescent dye, wherein the fluorescence of the dye is shifted upon micelle assembly and disassembly (spectral shift).

35. The delivery system according to claim 31, wherein the labeling moiety is a fluorinated labeling moiety, the fluorinated labeling moiety being a magnetic resonance (MR) probe capable of turning on a $^{19}$F-MR signal, and wherein the $^{19}$F-MR signal is turned OFF upon micelle assembly, and turned ON upon enzymatic activation and micelle disassembly.

36. The delivery system according to claim 31, wherein the micelle has an average particle size of less than about 100 nm, preferably, between about 10 nm and 50 nm, more preferably about 10 nm or 20 nm.

37. A method of delivering the delivery system according to claim 31, comprising the step of contacting the delivery system with an enzyme to induce cleavage of the enzymatically cleavable hydrophobic end group, thereby disassembling said micelle.

38. A kit for delivering the delivery system according to claim 31, comprising in one compartment the delivery system, and in a second compartment an enzyme capable of cleaving the enzymatically cleavable hydrophobic end group so as to disassemble said micelle.

39. A method of monitoring enzymatic activity in a biological system, the method comprising the step of contacting the biological system with a delivery system according to claim 1, and monitoring said enzymatic activity by fluorescence or $^{19}$F-magnetic resonance (MR).

40. The hybrid polymer according to claim 1, in the form of a self-assembled micelle, wherein the micelle disassembles upon enzymatic cleavage of the hydrophobic end group; and wherein the labeling moiety provides a different signal in the assembled vs. unassembled state of the micelle.

41. The hybrid polymer according to claim 40, wherein the labeling moiety in the hybrid polymer is a fluorescent dye, wherein the fluorescent dye is a self-quenching dye or an excimer forming dye, and wherein the fluorescence of the dye, when used alone or in combination with another dye or a dark quencher, is wholly or partially quenched or is shifted upon micelle assembly, and said dye regains its intrinsic fluorescence upon micelle disassembly.

42. A mixture comprising a multiplicity of hybrid polymers according to claim 1, in the form of a self-assembled micelle, wherein the multiplicity of hybrid polymers contain the same labeling moiety or different labeling moiety.

43. The mixture according to claim 42 comprising:
(a) a hybrid polymer comprising a self-quenching fluorescent dye (FRET), wherein the fluorescence of the dye is wholly or partially quenched upon micelle assembly (TURN OFF);
(b) a mixture of a hybrid polymer comprising a fluorescent dye and a hybrid polymer comprising dark quencher, wherein the fluorescence of the dye is wholly or partially quenched upon micelle assembly (TURN OFF);
(c) a mixture of hybrid polymers comprising two or more different fluorescent dyes, wherein the fluorescence of the dyes is shifted upon micelle assembly (FRET) and disassembly (spectral shift); or
(d) a hybrid polymer comprising an excimer forming fluorescent dye, wherein the fluorescence of the dye is shifted upon micelle assembly and disassembly (spectral shift).

44. The hybrid polymer according to claim 40, wherein the labeling moiety is a fluorinated labeling moiety, the fluorinated labeling moiety being a magnetic resonance (MR) probe capable of turning on a $^{19}$F-MR signal, and wherein the $^{19}$F-MR signal is turned OFF upon micelle assembly, and turned ON upon enzymatic activation and micelle disassembly.

45. The hybrid polymer according to claim 40, wherein the micelle has an average particle size of less than about 100 nm, preferably, between about 10 nm and 50 nm, more preferably about 10 nm or 20 nm.

46. The hybrid delivery polymer according to claim 40, which self-assembles into a therapeutic drug delivery platform in micellar form that self-reports its location and degree of activation.

\* \* \* \* \*